(12) United States Patent
Shoichet et al.

(10) Patent No.: US 10,780,078 B2
(45) Date of Patent: Sep. 22, 2020

(54) MU OPIOID RECEPTOR MODULATORS

(71) Applicants: THE REGENTS OF THE UNIVERSITY OF CALIFORNIA, Oakland, CA (US); THE BOARD OF TRUSTEES OF THE LELAND STANFORD JUNIOR UNIVERSITY, Palo Alto, CA (US); FRIEDRICH-ALEXANDER-UNIVERSITÄT ERLANGEN-NÜRNBERG, Erlangen (DE)

(72) Inventors: Brian K. Shoichet, Kentfield, CA (US); Anat Levit, San Francisco, CA (US); Aashish Manglik, Menlo Park, CA (US); Brian Kobilka, Palo Alto, CA (US); Peter Gmeiner, Erlangen (DE); Harald Hübner, Heroldsbach (DE); Daniela Gisela Dengler, Erlangen (DE)

(73) Assignees: THE REGENTS OF THE UNIVERSITY OF CALIFORNIA, Oakland, CA (US); FRIEDRICH-ALEXANDER-UNIVERSITÄT, Erlangen (DE); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 16/104,803

(22) Filed: Aug. 17, 2018

(65) Prior Publication Data

US 2019/0055208 A1 Feb. 21, 2019

Related U.S. Application Data

(60) Provisional application No. 62/546,947, filed on Aug. 17, 2017.

(51) Int. Cl.
*A61K 31/381* (2006.01)
*C07D 333/24* (2006.01)
(Continued)

(52) U.S. Cl.
CPC ............ *A61K 31/381* (2013.01); *A61P 25/04* (2018.01); *A61P 25/22* (2018.01); *A61P 25/24* (2018.01);
(Continued)

(58) Field of Classification Search
CPC ........................ A61K 31/381; C07D 333/24
(Continued)

(56) References Cited

FOREIGN PATENT DOCUMENTS

| WO | WO-2010/013037 A1 | 2/2010 |
| WO | WO-2017/007695 A1 | 1/2017 |

(Continued)

OTHER PUBLICATIONS

Anderson, Chemistry & Biology (2003), vol. 10, pp. 787-797. (Year: 2003).*

(Continued)

*Primary Examiner* — Craig D Ricci
*Assistant Examiner* — Janet L. Coppins
(74) *Attorney, Agent, or Firm* — Mintz, Levin, Cohn, Ferris, Glovsky and Popeo, P.C.; Irina E. Britva

(57) ABSTRACT

Described herein, inter alia, are compositions and methods for modulating mu opioid receptor activity.

19 Claims, 1 Drawing Sheet

(51) Int. Cl.

| | |
|---|---|
| *C07C 275/24* | (2006.01) |
| *C07D 333/20* | (2006.01) |
| *C07C 225/20* | (2006.01) |
| *A61P 25/36* | (2006.01) |
| *A61P 25/22* | (2006.01) |
| *A61P 25/04* | (2006.01) |
| *A61P 25/24* | (2006.01) |

(52) U.S. Cl.
CPC ............ *A61P 25/36* (2018.01); *C07C 225/20* (2013.01); *C07C 275/24* (2013.01); *C07D 333/20* (2013.01); *C07D 333/24* (2013.01); *C07C 2601/04* (2017.05); *C07C 2602/08* (2017.05); *C07C 2602/12* (2017.05)

(58) Field of Classification Search
USPC .......................................................... 514/438
See application file for complete search history.

(56) References Cited

FOREIGN PATENT DOCUMENTS

| | | | |
|---|---|---|---|
| WO | WO-2017007695 A1 * | 1/2017 | ........... C07D 498/18 |
| WO | WO-2017/035366 A1 | 3/2017 | |
| WO | WO-2019/036678 A1 | 2/2019 | |

OTHER PUBLICATIONS

Shi et al, Organic Letters (2003), vol. 5(5), pp. 633-636. (Year: 2003).*
Thiel, Nature Biotechnology (2004), vol. 22 (5), pp. 513-319. (Year: 2004).*
International Search Report dated Oct. 31, 2018, for PCT Application No. PCT/US2018/046983, filed Aug. 17, 2018, 5 pages.
Deekonda, S. et al. (Jan. 15, 2016, e-published Nov. 23, 2015). "Design synthesis and structure-activity relationship of 5-substituted (tetrahydronaphthalen-2yl)methyl with N-phenyl-N-(piperidin-2-yl)propionamide derivatives as opioid ligands," *Bioorg Med Chem* 24(2):85-91.
Written Opinion dated Oct. 31, 2018, for PCT Application No. PCT/US2018/046983, filed Aug. 17, 2018, 6 pages.

* cited by examiner

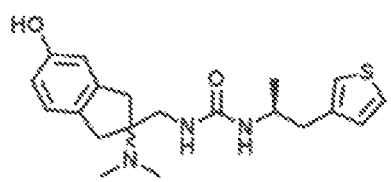
DD 297A/B
For diastereomer A:
$K_i$ MOR: 5.9 nM (5)
$K_i$ KOR: 6.5 nM (3)
$K_i$ DOR: 68 nM (3)
For diastereomer B:
$K_i$ MOR: 190 nM (5)
$K_i$ KOR: 260 nM (2)
$K_i$ DOR: 2000 nM (3)

MU OPIOID RECEPTOR MODULATORS

CROSS-REFERENCE TO RELATED APPLICATIONS

This application claims the benefit of U.S. Provisional Application No. 62/546,947, filed Aug. 17, 2017, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant nos. GM059957, GM106990, and DA036246, awarded by the National Institutes of Health. The government has certain rights in the invention.

BACKGROUND

The use of opioids in therapy dates to the Neolithic, and their effectiveness for pain treatment, as euphoragens, and their addictiveness has made them central to medicine, commerce, and conflict ever since. Their addictiveness and potentially lethal side effects, such as respiratory depression, have driven campaigns to improve them since the 19$^{th}$ century, with the purification of morphine and codeine and the synthesis of heroin. Recently, molecular studies have in fact suggested that the CNS-based analgesia relates to μ opioid receptor signaling through the $G_i$-protein pathway, while many of the pathophysiologies of the opioid drugs, including respiratory depression and constipation, is conferred via arrestin pathway signaling. Identifying agonists specific to μ opioid receptors (MOR) and biased toward the $G_i$-protein pathway have thus far remained elusive. Disclosed herein, inter alia, are solutions to these and other problems in the art.

BRIEF SUMMARY OF THE INVENTION

In an aspect is provided herein, a compound having the formula:

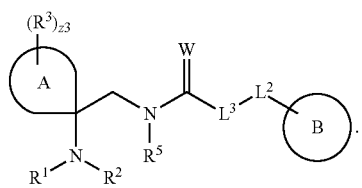

W is O or S. Ring A is a monocyclic cycloalkyl, monocyclic heterocycloalkyl, fused ring aryl, or fused ring heteroaryl. Ring B is independently substituted or unsubstituted cycloalkyl, substituted or unsubstituted heterocycloalkyl, substituted or unsubstituted aryl, or substituted or unsubstituted heteroaryl. $L^2$ is a bond, substituted or unsubstituted ($C_1$-$C_5$) alkylene, or substituted or unsubstituted 2 to 5 membered heteroalkylene. $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$N_3$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. $R^3$ is independently hydrogen, halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$N_3$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —$N_3$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ and $R^8$ substituents bonded to the same nitrogen atom may optionally be joined to form a substituted or unsubstituted heterocycloalkyl or substituted or unsubstituted heteroaryl. $R^1$ and $R^2$ may optionally be joined to form a substituted or unsubstituted 3 to 6 membered heterocycloalkyl or substituted or unsubstituted 5 to 6 membered heteroaryl. $R^1$ and $R^3$ may optionally be joined to form a substituted or unsubstituted 3 to 6 membered heterocycloalkyl or substituted or unsubstituted 5 to 6 membered heteroaryl. $R^2$ and $R^3$ may optionally be joined to form a substituted or unsubstituted 3 to 6 membered heterocycloalkyl or substituted or unsubstituted 5 to 6 membered heteroaryl. $L^3$ is a bond, —O—, —N($R^6$)—, or —$CH_2$—. $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. The symbol z3 is an integer from to 1 to 10. The symbols m and v are independently 1 or 2. The symbol n is independently an integer from 0 to 4. The symbol X is independently —Cl, —Br, —I, or —F.

In an aspect is provided herein, a compound having the formula:

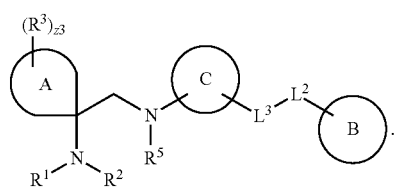

Ring A is a monocyclic cycloalkyl, monocyclic heterocycloalkyl, fused ring aryl, or fused ring heteroaryl. Ring B is independently substituted or unsubstituted cycloalkyl, substituted or unsubstituted heterocycloalkyl, substituted or unsubstituted aryl, or substituted or unsubstituted heteroaryl. Ring C is substituted or unsubstituted cycloalkylene, substituted or unsubstituted heterocycloalkylene, substituted or unsubstituted arylene, or substituted or unsubstituted heteroarylene. $L^2$ is a bond, substituted or unsubstituted ($C_1$-$C_5$) alkylene, or substituted or unsubstituted 2 to 5 membered heteroalkylene. $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$N_3$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. $R^3$ is independently hydrogen, —$N_3$, halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —$N(O)_m$, —$NR^7R^8$, —$C(O)R^9$, —C(O)—$OR^9$, —$C(O)NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ and $R^8$ substituents bonded to the same nitrogen atom may optionally be joined to form a substituted or unsubstituted heterocycloalkyl or substituted or unsubstituted heteroaryl. $R^1$ and $R^2$ may optionally be joined to form a substituted or unsubstituted 3 to 6 membered heterocycloalkyl or substituted or unsubstituted 5 to 6 membered heteroaryl. $R^1$ and $R^3$ may optionally be joined to form a substituted or unsubstituted 3 to 6 membered heterocycloalkyl or substituted or unsubstituted 5 to 6 membered heteroaryl. $R^2$ and $R^3$ may optionally be joined to form a substituted or unsubstituted 3 to 6 membered heterocycloalkyl or substituted or unsubstituted 5 to 6 membered heteroaryl. $L^3$ is a bond, —O—, —$N(R^6)$—, or —$CH_2$—. $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. The symbol z3 is an integer from to 1 to 10. The symbols m and v are independently 1 or 2. The symbol n is independently an integer from 0 to 4. The symbol X is independently —Cl, —Br, —I, or —F.

In embodiments, the compound has the formula:

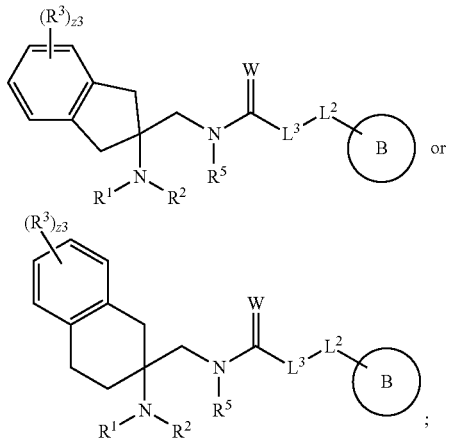

wherein, Ring B is independently substituted or unsubstituted cycloalkyl, substituted or unsubstituted heterocycloalkyl, substituted or unsubstituted aryl, or substituted or unsubstituted heteroaryl; $L^2$ is substituted or unsubstituted ($C_2$-$C_5$) alkylene, or substituted or unsubstituted 2 to 5 membered heteroalkylene; $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —$N(O)_m$, —$NR^7R^8$, —$C(O)R^9$, —C(O)—$OR^9$, —$C(O)NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^1$ and $R^2$ may optionally be joined to form a substituted or unsubstituted 3 to 6 membered heterocycloalkyl or substituted or unsubstituted 5 to 6 membered heteroaryl; $R^1$ and $R^3$ may optionally be joined to form a substituted or unsubstituted 3 to 6 membered heterocycloalkyl or substituted or unsubstituted 5 to 6 membered heteroaryl; $R^2$ and $R^3$ may optionally be joined to form a substituted or unsubstituted 3 to 6 membered heterocycloalkyl or substituted or unsubstituted 5 to 6 membered heteroaryl; $L^3$ is —O— or —N($R^6$)—; $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, the compound has the formula:

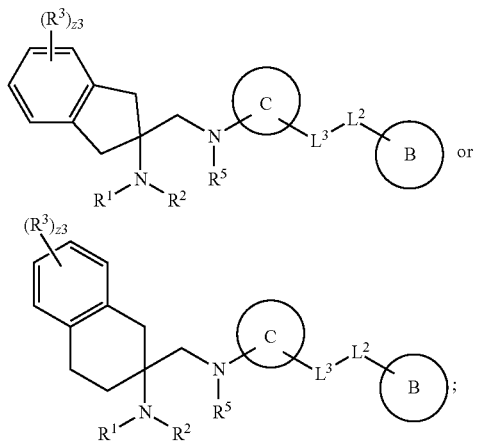

wherein, Ring B is independently substituted or unsubstituted cycloalkyl, substituted or unsubstituted heterocycloalkyl, substituted or unsubstituted aryl, or substituted or unsubstituted heteroaryl; Ring C is substituted or unsubstituted cycloalkylene, substituted or unsubstituted heterocycloalkylene, substituted or unsubstituted arylene, or substituted or unsubstituted heteroarylene; $L^2$ is substituted or unsubstituted ($C_2$-$C_5$) alkylene, or substituted or unsubstituted 2 to 5 membered heteroalkylene; $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC (O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^1$ and $R^2$ may optionally be joined to form a substituted or unsubstituted 3 to 6 membered heterocycloalkyl or substituted or unsubstituted 5 to 6 membered heteroaryl; $R^1$ and $R^3$ may optionally be joined to form a substituted or unsubstituted 3 to 6 membered heterocycloalkyl or substituted or unsubstituted 5 to 6 membered heteroaryl; $R^2$ and $R^3$ may optionally be joined to form a substituted or unsubstituted 3 to 6 membered heterocycloalkyl or substituted or unsubstituted 5 to 6 membered heteroaryl; $L^3$ is —O— or —N($R^6$)—; $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In another aspect is provided a pharmaceutical composition including a pharmaceutically acceptable excipient and a compound, as described herein.

In an aspect is provided a method of treating pain in a subject in need of the treatment, the method including administering an effective amount of a compound as described herein, to the subject. In embodiments, the method does not include an increased risk of respiratory depression or constipation.

In an aspect is provided a method of treating opioid overdose in a subject in need of the treatment, the method including administering an effective amount of a compound as described herein, to the subject.

In another aspect is provided a method of treating addiction in a subject in need of the treatment, the method including administering an effective amount compound as described herein, to the subject.

In an aspect is provided a method of treating a psychiatric disorder in a subject in need of the treatment, the method including administering an effective amount of a compound as described herein, to the subject.

In another aspect is provided a method of modulating the activity of an opioid receptor protein, the method including contacting the opioid receptor protein with an effective amount of a compound as described herein.

BRIEF DESCRIPTION OF THE DRAWINGS

FIG. 1. Activity data for compounds DD 297A and DD 297B.

DETAILED DESCRIPTION

Structure-based optimization to determine potent agonists for µOR activity with improved selectivity as compared to the three other opioid receptors (δ, κ, and nociceptin). Unlike the respiratory depression observed with morphine, an equi-analgesic dose of compounds described herein has little effect on respiration.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbon atoms (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene," by itself or as part of another substituent, means, unless otherwise stated, a divalent radical derived from an alkyne.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from heteroalkenyl. The term "heteroalkynylene," by itself or as part of another substituent, means, unless otherwise stated, a divalent radical derived from heteroalkynyl The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. The terms "cycloalkenyl" and "cycloalkynyl," by themselves or in combination with other terms, mean, unless otherwise stated, cyclic versions of "alkenyl" and "alkynyl," respectively. The terms "heterocycloalkenyl" and "heterocycloalkynyl," by themselves or in combination with other terms, mean, unless otherwise stated, cyclic versions of "heteroalkenyl" and "heteroalkynyl," respectively. The term "monocyclic cycloalkyl" refers to a cycloalkyl containing one cyclic group (e.g., cyclohexyl). The term "monocyclic heterocycloalkyl" refers to a heterocycloalkyl containing one cyclic group (e.g., piperidinyl).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. A fused ring aryl may be referred to as an aryl fused cycloalkyl. In embodiments, a fused ring aryl has the formula:

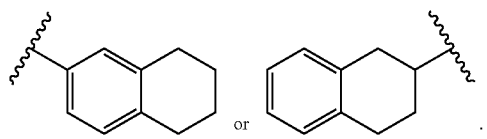

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A fused ring heteroaryl refers to multiple rings fused together wherein at least one of the fused rings is a heteroaryl ring. A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~~~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

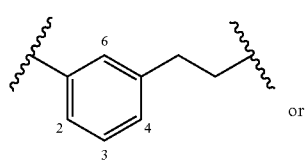

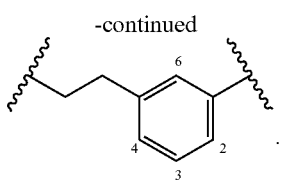

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —$NO_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)N"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'N"R", —ONR'R", —NR'C(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:
(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —N$_3$, CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCHCl$_2$, —OCH Br$_2$, —OCHF$_2$, —OCHI$_2$, —OCH$_2$Cl, —OCH$_2$Br, —OCH$_2$F, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(B) alkyl, heteroalkyl, cycloalkyl, heterocycloalkyl, aryl, heteroaryl, substituted with at least one substituent selected from:
  (i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCHCl$_2$, —OCHBr$_2$, —OCHF$_2$, —OCHI$_2$, —OCH$_2$Cl, —OCH$_2$Br, —OCH$_2$F, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
  (ii) alkyl, heteroalkyl, cycloalkyl, heterocycloalkyl, aryl, heteroaryl, substituted with at least one substituent selected from:
    (a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCHCl$_2$, —OCHBr$_2$, —OCHF$_2$, —OCHI$_2$, —OCH$_2$Cl, —OCH$_2$Br, —OCH$_2$F, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
    (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —N$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCHCl$_2$, —OCHBr$_2$, —OCHF$_2$, —OCHI$_2$, —OCH$_2$Cl, —OCH$_2$Br, —OCH$_2$F, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, claims, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally differently.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol or number may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc. (or $R^{13.1}$, $R^{13.2}$, $R^{13.3}$, $R^{13.4}$, etc.), wherein each of $R^{13A}$, $R^{13B}$, $R^{13C}$, $R^{13D}$, etc. (or $R^{13.1}$, $R^{13.2}$, $R^{13.3}$, $R^{13.4}$, etc.) is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the compounds described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients are useful in combination with the compounds described herein.

Pharmaceutical compositions may include compositions wherein the active ingredient (e.g. compounds described herein) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "mu opioid receptor modulator" or "mu opioid receptor compound" or "μ opioid receptor modulator" or "MOR" refers to a compound (e.g. compounds described herein) that reduce the activity of μ opioid receptor when compared to a control, such as absence of the compound or a compound with known inactivity.

A "specific," "specifically", "specificity", or the like of a compound refers to the compound's ability to discriminate between particular molecular targets to a significantly greater extent than other proteins in the cell (e.g. a compound having specificity towards opioid receptor ("μ opioid receptor-specific compound" or a compound including a "μ opioid receptor-specific moiety") binds to μ opioid receptor whereas the same compound displays little-to-no binding to other opioid receptors such as kappa opioid receptor or delta opioid receptor, or nociceptin receptor). A "μ opioid receptor-specific compound" refers to a compound (e.g. compounds described herein) having specificity towards μ opioid receptor (e.g., over one or more other opioid receptors).

The terms "selective," or "selectivity" or the like of a compound refers to the compound's ability to cause a particular action in a particular molecular target (e.g. a compound having selectivity toward opioid receptor would inhibit only opioid receptor). A "μ opioid receptor-selective compound" or a compound including a "μ opioid receptor-selective moiety" refers to a compound (e.g. compounds described herein) having selectivity towards opioid receptor.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein-activator interaction means positively affecting (e.g. increasing) the activity or function of the protein relative to the activity or function of the protein in the absence of the activator. In embodiments inhibition refers means positively affecting (e.g. increasing) the concentration or levels of the protein relative to the concentration or level of the protein in the absence of the activator. In embodiments, activation refers to an increase in the activity of a particular protein target (mu opioid receptor). Thus, activation includes, at least in part, partially or totally increasing stimulation or activation, or activating, sensitizing, or up-regulating signal transduction or enzymatic activity or the amount of a protein. In embodiments, activation refers to an increase of activity of a target protein resulting from a direct interaction (e.g. an activator binds to the target protein). In embodiments, activation refers to an increase of activity of a target protein from an indirect interaction (e.g. an activator binds to a protein that inhibits the target protein, thereby causing target protein activation).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition refers means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

Opioid receptors are a group of inhibitory G-protein coupled receptors that bind opioids (e.g., endogenous opioids are dynorphins, enkephalins, endorphins, endomorphins, and nociception).

The terms "μ opioid receptor" and "mu opioid receptor" or "MOR" refer to a subtype of opioid receptor and is used according to its common, ordinary meaning. "μ opioid receptor" refers to proteins of the same or similar names, homologs, isoforms, and functional fragments thereof, so long as such fragments retain μ opioid receptor activity. The term includes any recombinant or naturally-occurring form of μ opioid receptor, or variants thereof that maintain μ opioid receptor activity (e.g. within at least 30%, 40%, 50%, 60%, 70%, 80%, 90%, 95%, or 100% activity compared to wildtype opioid receptor). In embodiments, the opioid receptor protein encoded by the OPRM1 gene has the amino acid sequence set forth in RefSeq (mRNA) NM_000914, NM_001008503, NM_001008504, NM_001008505, NM_001145279, NM_001145280, NM_001145281, NM_001145282, NM_001145283, NM_001145284, NM_001145285, NM_001145286, NM_001145287, NM_001285522, NM_001285523, NM_001285524, NM_001285526, NM_001285527, or NM_001285528. In embodiments, the μ opioid receptor protein encoded by the OPRM1 gene has the amino acid sequence set forth in RefSeq (protein) NP_000905.3, NP_001008503.2, NP_001008504.2, NP_001008505.2, NP_001138751.1, NP_001138752.1, NP_001138753.1, NP_001138754.1, NP_001138755.1, NP_001138756.1, NP_001138757.1, NP_001138758.1, NP_001138759.1, NP_001272452.1, NP_001272453.1, NP_001272455.1, NP_001272456.1, or NP_001272457.1.

In embodiments, the μ opioid receptor protein encoded by the OPRM1 gene has the amino acid sequence set forth in Entrez 4988, UniProt P35372, RefSeq (mRNA) NM_000914, or RefSeq (protein) NP_000905. In embodiments, the μ opioid receptor protein is a human protein. In embodiments, the μ opioid receptor protein is a wildtype protein. In embodiments, the μ opioid receptor protein mutant protein. In embodiments, the μ opioid receptor protein corresponds to GI: 117940060. In embodiments, the μ opioid receptor protein corresponds to NP_000905.3. In embodiments, the μ opioid receptor protein corresponds to GI:550822366. In embodiments, the μ opioid receptor protein corresponds to NM_000914.4.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be pain, such as for example, nociceptive pain, inflammatory pain which is associated with tissue damage and/or the infiltration of immune cells, or pathological pain, for example a disease state caused by damage to the nervous system (neuropathic pain) or by its abnormal function (dysfunctional pain (e.g., fibromyalgia, irritable bowel syndrome, tension type headache)). In embodiments, the pain may be acute pain. In embodiments, the pain may be chronic pain. In embodiments, the nociceptive pain may be associated with ischemia. In embodiments, the nociceptive pain may be associated with inflammation. In embodiments, the nociceptive pain may be deep somatic pain (e.g., due to damage to ligaments, tendons, bonds, blood vessels, fasciae, or muscles). In embodiments, the nociceptive pain may be associated with skin. In embodiments, the nociceptive pain may be associated with a burn. In embodiments, the pain may be psychogenic (e.g., associated with headache, back pain, stomach pain). In embodiments, the pain may be breakthrough pain. In embodiments, the pain may be breakthrough pain not treated by standard pain management. In embodiments, the pain may be breakthrough pain associated with cancer. In embodiments, the pain may be a pain capable of being treated with an opioid. The disease may be a drug addiction (e.g., addiction to an opioid, tobacco, narcotic, heroin, morphine, opiate, alcohol, cocaine, amphetamine, methamphetamine, MDMA, GHB, LSD, PCP, hydrocodone, oxycodone, fentanyl, or marijuana, methadone, hydromorphone, or a derivative thereof). The disease may be opioid poisoning (e.g., overdose), for example poisoning with heroin, fentanyl, or morphine.

The terms "treating", or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment of symptoms can be based on objective or subjective parameters; including the results of a physical examination, neuropsychiatric exams, and/or a psychiatric evaluation. The terms treatment, therapy and the like include, but are not limited to, methods and manipulations to produce beneficial changes in a recipient's health status. The changes can be either subjective or objective and can relate to features such as symptoms or signs of the disease, disorder or condition being treated. For example, if the patient notes decreased pain, then successful treatment of pain has occurred. The term "treating" and conjugations thereof, include prevention of an injury, pathology, condition, or disease.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of*

*Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule relative to the absence of the modulator. In some embodiments, a μ opioid receptor disease modulator is a compound that reduces the severity of one or more symptoms of a disease associated with μ opioid receptor (e.g. pain or drug addiction). A μ opioid receptor modulator is a compound that increases or decreases the activity or function or level of activity or level of function of μ opioid receptor or level of μ opioid receptor in a particular physical state.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a pain associated with μ opioid receptor activity, μ opioid receptor associated pain, μ opioid receptor associated disease, μ opioid receptor associated drug addiction. For example, a pain associated with μ opioid receptor activity or function may be a pain that results (entirely or partially) from aberrant μ opioid receptor function (e.g. enzyme activity, protein-protein interaction, signaling pathway) or a pain wherein a particular symptom of the disease is caused (entirely or partially) by aberrant μ opioid receptor activity or function. As used herein, what is described as being associated with a disease, if a causative agent, could be a target for treatment of the disease. For example, a pain associated with μ opioid receptor activity or function or a μ opioid receptor associated pain, may be treated with a μ opioid receptor modulator or μ opioid receptor activator, in the instance where decreased μ opioid receptor activity or function (e.g. signaling pathway activity) causes the pain. For example, a drug addiction associated with increased μ opioid receptor activity or function or a μ opioid receptor associated addiction, may be treated with a opioid receptor modulator or opioid receptor inhibitor, in the instance where increased (e.g., due to the addictive drug) opioid receptor activity or function (e.g. signaling pathway activity) causes the drug addiction.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propogated to other signaling pathway components. For example, binding of a opioid receptor with a compound as described herein may result in a change in one or more protein-protein interactions of the μ opioid receptor or interactions between the μ opioid receptor and downstream effectors or signaling pathway components, resulting in changes in cell function.

II. Compounds

In an aspect is provided herein, a compound having the formula:

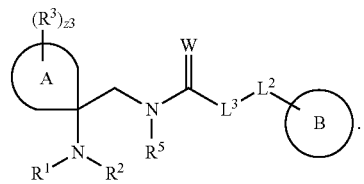

W is O or S. Ring A is a monocyclic cycloalkyl, monocyclic heterocycloalkyl, fused ring aryl, or fused ring heteroaryl. Ring B is independently substituted or unsubstituted cycloalkyl, substituted or unsubstituted heterocycloalkyl, substituted or unsubstituted aryl, or substituted or unsubstituted heteroaryl. $L^2$ is a bond, substituted or unsubstituted $(C_1-C_5)$ alkylene, or substituted or unsubstituted 2 to 5 membered heteroalkylene. $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$N_3$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. $R^3$ is independently hydrogen, halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ and $R^8$ substituents bonded to the same nitrogen atom may optionally be joined to form a substituted or unsubstituted heterocycloalkyl or substituted or unsubstituted heteroaryl. $R^1$ and $R^2$ may optionally be joined to form a substituted or unsubstituted 3 to 6 membered heterocycloalkyl or substituted or unsubstituted 5 to 6 membered heteroaryl. $R^1$ and $R^3$ may optionally be joined to form a substituted or unsubstituted 3 to 6 membered heterocycloalkyl or substituted or unsubstituted 5 to 6 membered heteroaryl. $R^2$ and $R^3$ may optionally be joined to form a substituted or unsubstituted 3 to 6 membered heterocycloalkyl or substituted or unsubstituted 5 to 6 membered heteroaryl. $L^3$ is a bond, —O—, —N($R^6$)—, or —$CH_2$—. $R^5$ is hydrogen, —$CF_3$, —CN, —COOH, —$CONH_2$, —$CHF_2$, —$CH_2F$, substituted or unsubstituted $(C_1-C_5)$ alkyl, or substituted or unsubstituted 2 to 5 membered heteroalkyl. $R^6$ is hydrogen, —$CF_3$, —CN, —COOH, —$CONH_2$, —$CHF_2$, —$CH_2F$, substituted or unsubstituted $(C_1-C_5)$ alkyl, or substituted or unsubstituted 2 to 5 membered heteroalkyl. The symbol z3 is an integer from to 1 to 10. The symbols m and v are independently 1 or 2. The symbol n is independently an integer from 0 to 4. The symbol X is independently —Cl, —Br, —I, or —F.

In an aspect is provided herein, a compound having the formula:

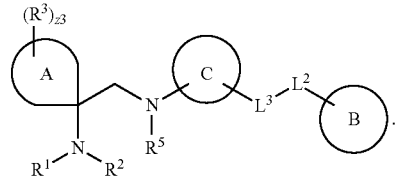

Ring A is a monocyclic cycloalkyl, monocyclic heterocycloalkyl, fused ring aryl, or fused ring heteroaryl. Ring B is independently substituted or unsubstituted cycloalkyl, substituted or unsubstituted heterocycloalkyl, substituted or unsubstituted aryl, or substituted or unsubstituted heteroaryl. Ring C is substituted or unsubstituted cycloalkylene, substituted or unsubstituted heterocycloalkylene, substituted or unsubstituted arylene, or substituted or unsubstituted heteroarylene. $L^2$ is a bond, substituted or unsubstituted $(C_1-C_5)$ alkylene, or substituted or unsubstituted 2 to 5 membered heteroalkylene. $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$N_3$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —$NHC\!=\!(O)NHNR^7R^8$, —$NHC\!=\!(O)NR^7R^8$, —$N(O)_m$, —$NR^7R^8$, —$C(O)R^9$, —C(O)—$OR^9$, —$C(O)NR^7R^8$, —$OR^{10}$, —$NR^7SO_2R^1$, —$NR^7C\!=\!(O)R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC\!=\!(O)NHNH_2$, —$NHC\!=\!(O)NH_2$, —$NHSO_2H$, —$NHC\!=\!(O)H$, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ and $R^8$ substituents bonded to the same nitrogen atom may optionally be joined to form a substituted or unsubstituted heterocycloalkyl or substituted or unsubstituted heteroaryl. $R^1$ and $R^2$ may optionally be joined to form a substituted or unsubstituted 3 to 6 membered heterocycloalkyl or substituted or unsubstituted 5 to 6 membered heteroaryl. $R^1$ and $R^3$ may optionally be joined to form a substituted or unsubstituted 3 to 6 membered heterocycloalkyl or substituted or unsubstituted 5 to 6 membered heteroaryl. $R^2$ and $R^3$ may optionally be joined to form a substituted or unsubstituted 3 to 6 membered heterocycloalkyl or substituted or unsubstituted 5 to 6 membered heteroaryl. $L^3$ is a bond, —O—, —$N(R^6)$—, or —$CH_2$—. $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. The symbol z3 is an integer from to 1 to 10. The symbols m and v are independently 1 or 2. The symbol n is independently an integer from 0 to 4. The symbol X is independently —Cl, —Br, —I, or —F.

In aspects and embodiments of the compounds provided herein, where Ring A is a fused ring aryl, the fused ring aryl includes a non-aryl ring fused to an aryl ring, wherein Ring A is attached to the remainder of the compound through the non-aryl ring in keeping with the normal rules of valency. The non-aryl ring may be a heterocycloalkyl thereby forming a fused ring aryl-heterocycloalkyl. The non aryl ring may also be a cycloalkyl thereby forming a fused ring aryl-cycloalkyl.

In aspects and embodiments of the compounds provided herein, where Ring A is a fused ring heteroaryl, the fused ring heteroaryl includes a non-aryl ring fused to a heteroaryl ring, wherein Ring A is attached to the remainder of the compound through the non-aryl ring in keeping with the normal rules of valency. The non-aryl ring may be a heterocycloalkyl thereby forming a fused ring heteroaryl-heterocycloalkyl. The non aryl ring may also be a cycloalkyl thereby forming a fused ring heteroaryl-cycloalkyl.

In embodiments, the compound has the formula:

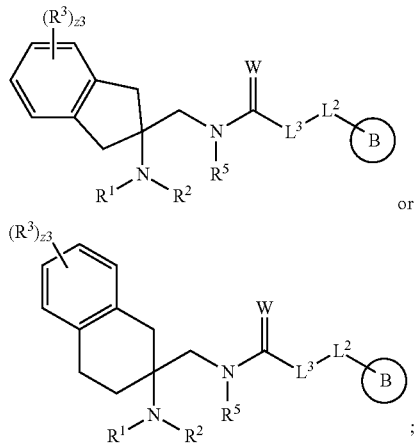

wherein, Ring B is independently substituted or unsubstituted cycloalkyl, substituted or unsubstituted heterocycloalkyl, substituted or unsubstituted aryl, or substituted or unsubstituted heteroaryl; $L^2$ is substituted or unsubstituted ($C_2$-$C_5$) alkylene, or substituted or unsubstituted 2 to 5 membered heteroalkylene; $R^1$ and $R^2$ are independently hydrogen, halogen, —$CF_3$, —CN, —OH, —$NH_2$, —COOH, —$CONH_2$, —$NO_2$, —SH, —$SO_3H$, —$SO_4H$, —$SO_2NH_2$, —$N^3$, —$NHNH_2$, —$ONH_2$, —$NHC\!=\!(O)NHNH_2$, —$NHC\!=\!(O)NH_2$, —$NHSO_2H$, —$NHC\!=\!(O)H$, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —$NHC\!=\!(O)NHNR^7R^8$, —$NHC\!=\!(O)NR^7R^8$, —$N(O)_m$, —$NR^7R^8$, —$C(O)R^9$, —C(O)—$OR^9$, —$C(O)NR^7R^8$, —$OR^{10}$, —$NR^7SO_2R^{10}$, —$NR^7C\!=\!(O)R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$N^3$, —$NHNH_2$, —$ONH_2$, —$NHC\!=\!(O)NHNH_2$, —$NHC\!=\!(O)NH_2$, —$NHSO_2H$, —$NHC\!=\!(O)H$, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^1$ and $R^2$ may optionally be joined to form a substituted or unsubstituted 3 to 6 membered heterocycloalkyl or substituted or unsubstituted 5 to 6 membered heteroaryl; $R^1$ and $R^3$ may optionally be joined to form a substituted or unsubstituted 3 to 6 membered heterocycloalkyl or substituted or unsubstituted 5 to 6 membered heteroaryl; $R^2$ and $R^3$ may optionally be joined to form a substituted or unsubstituted 3 to 6 membered heterocycloalkyl or substituted or unsubstituted 5 to 6 membered heteroaryl; $L^3$ is —O— or —N($R^6$)—; $R^5$ is hydrogen, —CF$_3$, —CN, —COOH, —CONH$_2$, —CHF$_2$, —CH$_2$F, substituted or unsubstituted ($C_1$-$C_5$) alkyl, or substituted or unsubstituted 2 to 5 membered heteroalkyl; $R^6$ is hydrogen, —CF$_3$, —CN, —COOH, —CONH$_2$, —CHF$_2$, —CH$_2$F, substituted or unsubstituted ($C_1$-$C_5$) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, the compound has the formula:

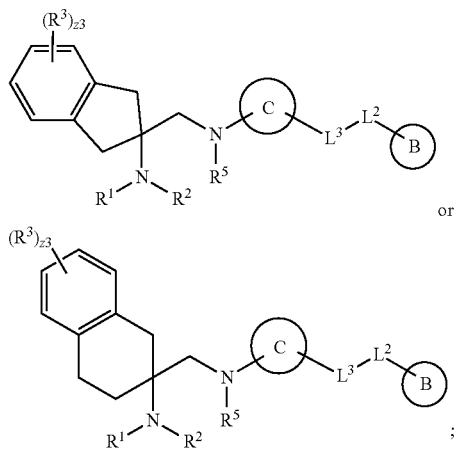

or wherein, Ring B is independently substituted or unsubstituted cycloalkyl, substituted or unsubstituted heterocycloalkyl, substituted or unsubstituted aryl, or substituted or unsubstituted heteroaryl; Ring C is substituted or unsubstituted cycloalkylene, substituted or unsubstituted heterocycloalkylene, substituted or unsubstituted arylene, or substituted or unsubstituted heteroarylene; $L^2$ is substituted or unsubstituted ($C_2$-$C_5$) alkylene, or substituted or unsubstituted 2 to 5 membered heteroalkylene; $R^1$ and $R^2$ are independently hydrogen, halogen, —CF$_3$, —CN, —OH, —NH$_2$, —COOH, —CONH$_2$, —NO$_2$, —SH, —SO$_3$H, —SO$_4$H, —SO$_2$NH$_2$, —N$^3$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —CX$_3$, —CN, —N$_3$, —SO$_n$R$^{10}$, —SO$_v$NR$^7$R$^8$, —N$_3$, —NHNR$^7$R$^8$, —ONR$^7$R$^8$, —NHC=(O)NHNR$^7$R$^8$, —NHC=(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C=(O)R$^9$, —NR$^7$C(O)OR$^9$, —NR$^7$OR$^9$, —CHX$_2$, —CH$_2$X, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^1$ and $R^2$ may optionally be joined to form a substituted or unsubstituted 3 to 6 membered heterocycloalkyl or substituted or unsubstituted 5 to 6 membered heteroaryl; $R^1$ and $R^3$ may optionally be joined to form a substituted or unsubstituted 3 to 6 membered heterocycloalkyl or substituted or unsubstituted 5 to 6 membered heteroaryl; $R^2$ and $R^3$ may optionally be joined to form a substituted or unsubstituted 3 to 6 membered heterocycloalkyl or substituted or unsubstituted 5 to 6 membered heteroaryl; $L^3$ is —O— or —N($R^6$)—; $R^5$ is hydrogen, —CF$_3$, —CN, —COOH, —CONH$_2$, —CHF$_2$, —CH$_2$F, substituted or unsubstituted ($C_1$-$C_5$) alkyl, or substituted or unsubstituted 2 to 5 membered heteroalkyl; $R^6$ is hydrogen, —CF$_3$, —CN, —COOH, —CONH$_2$, —CHF$_2$, —CH$_2$F, substituted or unsubstituted ($C_1$-$C_5$) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, the compound has the formula:

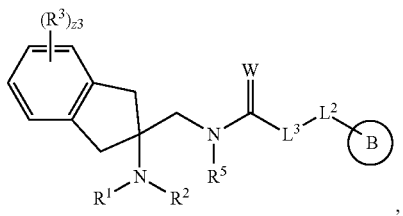

wherein $R^3$, z3, $R^1$, $R^2$, $R^5$, $L^3$, $L^2$, W, and Ring B is as described herein, including embodiments.

In embodiments, the compound has the formula:

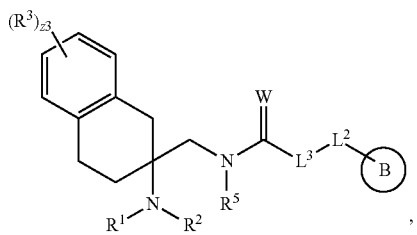

wherein $R^3$, z3, $R^1$, $R^2$, $R^5$, $L^3$, $L^2$, W, and Ring B is as described herein, including embodiments.

In embodiments, the compound has the formula:

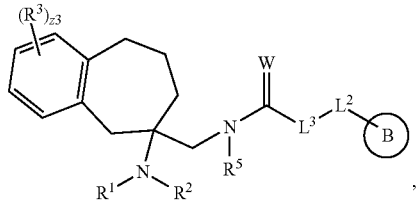

wherein $R^3$, z3, $R^1$, $R^2$, $R^5$, $L^3$, $L^2$, W, and Ring B is as described herein, including embodiments.

In embodiments, the compound has the formula:

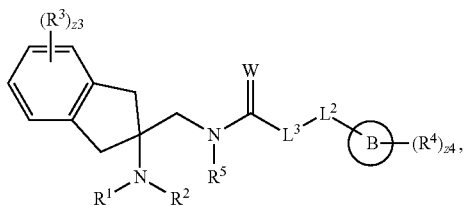

wherein $R^4$, z4, $R^3$, z3, $R^1$, $R^2$, $R^5$, $L^3$, $L^2$, W, and Ring B is as described herein, including embodiments. In embodiments, z4 is an integer from 0 to 10.

In embodiments, the compound has the formula:

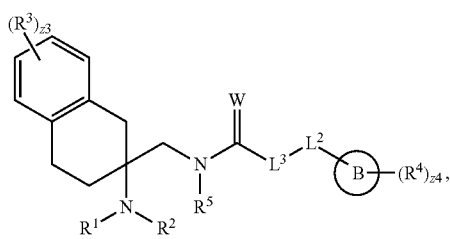

wherein $R^4$, z4, $R^3$, z3, $R^1$, $R^2$, $R^5$, $L^3$, $L^2$, W, and Ring B is as described herein, including embodiments. In embodiments, z4 is an integer from 0 to 10.

In embodiments, the compound has the formula:

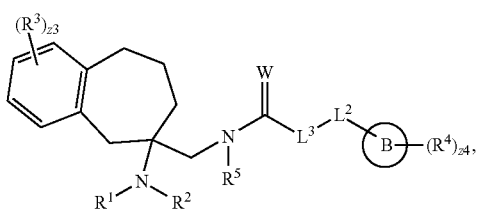

wherein $R^4$, z4, $R^3$, z3, $R^1$, $R^2$, $R^5$, $L^3$, $L^2$, W, and Ring B is as described herein, including embodiments. In embodiments, z4 is an integer from 0 to 10.

In embodiments, the compound has the formula:

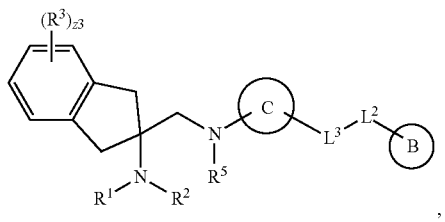

wherein $R^3$, z3, $R^1$, $R^2$, $R^5$, $L^3$, $L^2$, Ring C, and Ring B is as described herein, including embodiments.

In embodiments, the compound has the formula:

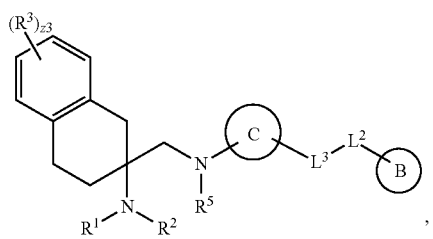

wherein $R^3$, z3, $R^1$, $R^2$, $R^5$, $L^3$, $L^2$, Ring C, and Ring B is as described herein, including embodiments.

In embodiments, the compound has the formula:

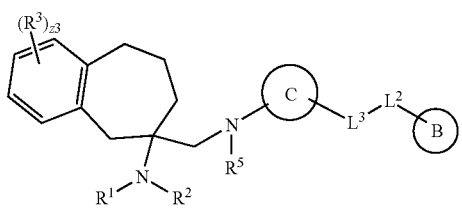

wherein $R^3$, z3, $R^1$, $R^2$, $R^5$, $L^3$, $L^2$, Ring C, and Ring B is as described herein, including embodiments.

In embodiments, the compound has the formula:

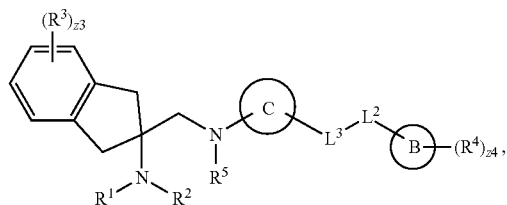

wherein $R^4$, z4, $R^3$, z3, $R^1$, $R^2$, $R^5$, $L^3$, $L^2$, Ring C, and Ring B is as described herein, including embodiments.

In embodiments, the compound has the formula:

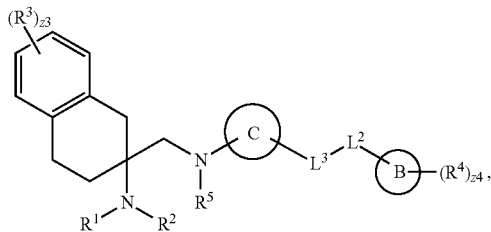

wherein R⁴, z4, R³, z3, R¹, R², R⁵, L³, L², Ring C, and Ring B is as described herein, including embodiments.

In embodiments, the compound has the formula:

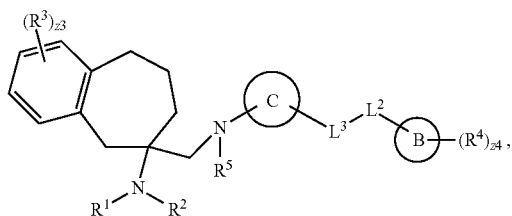

wherein R⁴, z4, R³, z3, R¹, R², R⁵, L³, L², Ring C, and Ring B is as described herein, including embodiments.

In embodiments, the compound has the formula:

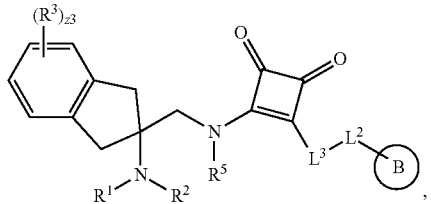

wherein R³, z3, R¹, R², R⁵, L³, L², and Ring B is as described herein, including embodiments.

In embodiments, the compound has the formula:

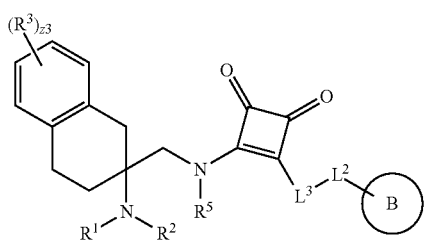

wherein R³, z3, R¹, R², R⁵, L³, L², and Ring B is as described herein, including embodiments.

In embodiments, the compound has the formula:

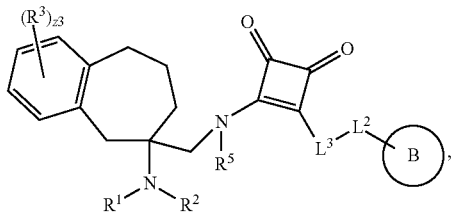

wherein R³, z3, R¹, R², R⁵, L³, L², and Ring B is as described herein, including embodiments.

In embodiments, the compound has the formula:

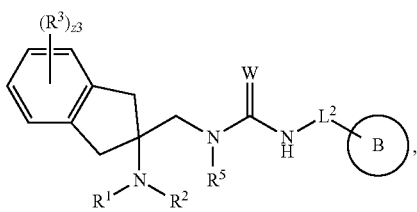

wherein R³, z3, R¹, R², R⁵, L², W, and Ring B is as described herein, including embodiments.

In embodiments, the compound has the formula:

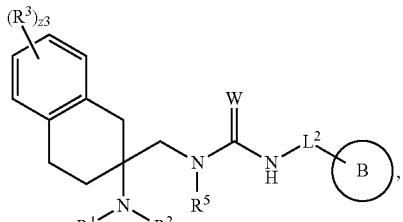

wherein R³, z3, R¹, R², R⁵, L², W, and Ring B is as described herein, including embodiments.

In embodiments, the compound has the formula:

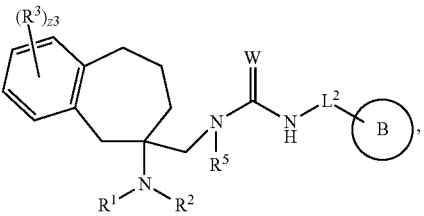

wherein R³, z3, R¹, R², R⁵, L², W, and Ring B is as described herein, including embodiments.

In embodiments, the compound has the formula:

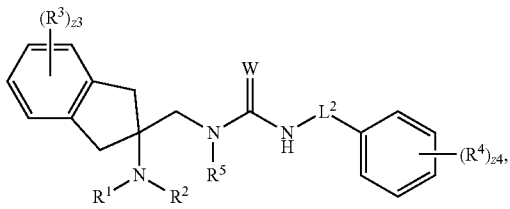

wherein R³, z3, z4, R¹, R², R⁵, L², W and R⁴ is as described herein, including embodiments.

In embodiments, the compound has the formula:

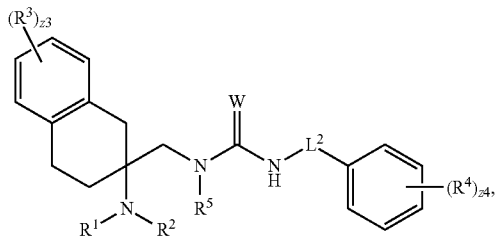

wherein R³, z3, z4, R¹, R², R⁵, L², W, and R⁴ is as described herein, including embodiments.

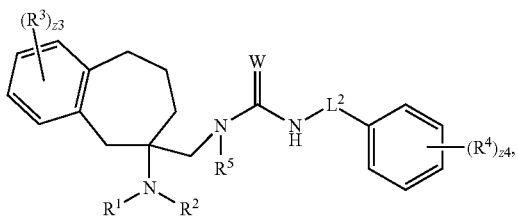

wherein R³, z3, z4, R¹, R², R⁵, L², W, and R⁴ is as described herein, including embodiments.

In embodiments, the compound has the formula:

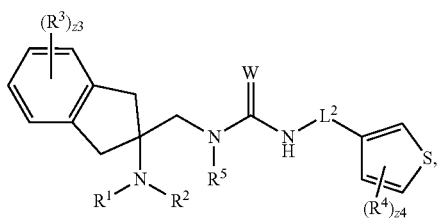

wherein R³, z3, z4, R¹, R², R⁵, L², W, and R⁴ is as described herein, including embodiments.

In embodiments, the compound has the formula:

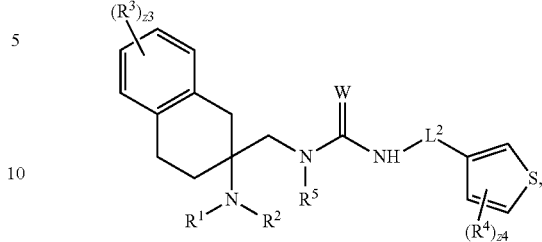

wherein R³, z3, z4, R¹, R², R⁵, L², W, and R⁴ is as described herein, including embodiments.

In embodiments, the compound has the formula:

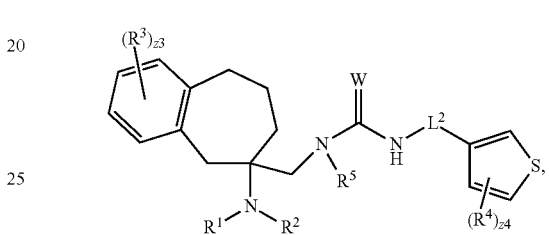

wherein R³, z3, z4, R¹, R², R⁵, L², W, and R⁴ is as described herein, including embodiments.

In embodiments, W is O. In embodiments, W is S.

In embodiments, R¹ is hydrogen, halogen, —CF₃, —CN, —N₃, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, —OCF₃, —OCHF₂, —OCH₂F. In embodiments, R¹ is substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. In embodiments, R¹ is hydrogen. In embodiments, R¹ is —CH₃.

In embodiments, R¹ is independently hydrogen, halogen, —CF₃, —CN, —N₃, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, —OCF₃, —OCHF₂, —OCH₂F, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl.

In embodiments, R¹ is substituted or unsubstituted ($C_1$-$C_{12}$) alkyl. In embodiments, R¹ is unsubstituted ($C_1$-$C_2$) alkyl. In embodiments, R¹ is substituted ($C_1$-$C_{12}$) alkyl, substituted with a substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

In embodiments, R¹ and R² may optionally be joined to form a substituted or unsubstituted 3 to 6 membered heterocycloalkyl or substituted or unsubstituted 3 to 6 membered heteroaryl. In embodiments, $R^1$ and $R^2$ may optionally be joined to form a substituted or unsubstituted 4 to 6 membered heterocycloalkyl or substituted or unsubstituted 4 to 6 membered heteroaryl. In embodiments, $R^1$ and $R^2$ may optionally be joined to form a substituted or unsubstituted 5 to 6 membered heterocycloalkyl or substituted or unsubstituted 5 to 6 membered heteroaryl. In embodiments, $R^1$ and $R^2$ may optionally be joined to form a substituted or unsubstituted 5 membered heterocycloalkyl or substituted or unsubstituted 5 membered heteroaryl. In embodiments, $R^1$ and $R^2$ may optionally be joined to form a substituted or unsubstituted 6 membered heterocycloalkyl or substituted or unsubstituted 6 membered heteroaryl. In embodiments, $R^1$ and $R^2$ are unsubstituted methyl. In embodiments, $R^1$ and $R^2$ are joined to form a substituted or unsubstituted 3 to 6 membered heterocycloalkyl or substituted or unsubstituted 5 to 6 membered heteroaryl.

In embodiments, $R^1$ and $R^3$ may optionally be joined to form a substituted or unsubstituted 3 to 6 membered heterocycloalkyl or substituted or unsubstituted 3 to 6 membered heteroaryl. In embodiments, $R^1$ and $R^3$ may optionally be joined to form a substituted or unsubstituted 4 to 6 membered heterocycloalkyl or substituted or unsubstituted 4 to 6 membered heteroaryl. In embodiments, $R^1$ and $R^3$ may optionally be joined to form a substituted or unsubstituted 5 to 6 membered heterocycloalkyl or substituted or unsubstituted 5 to 6 membered heteroaryl. In embodiments, $R^1$ and $R^3$ may optionally be joined to form a substituted or unsubstituted 5 membered heterocycloalkyl or substituted or unsubstituted 5 membered heteroaryl. In embodiments, $R^1$ and $R^3$ may optionally be joined to form a substituted or unsubstituted 6 membered heterocycloalkyl or substituted or unsubstituted 6 membered heteroaryl.

In embodiments, $R^1$ and $R^2$ are joined to form a substituted or unsubstituted 3 to 6 membered heterocycloalkyl or substituted or unsubstituted 5 to 6 membered heteroaryl. In embodiments, $R^1$ and $R^2$ are joined to form a substituted or unsubstituted 3 to 6 membered heterocycloalkyl. In embodiments, $R^1$ and $R^2$ are joined to form a $R^{30}$-substituted or unsubstituted 3 to 6 membered heterocycloalkyl. In embodiments, $R^1$ and $R^2$ are joined to form a $R^{30}$-substituted or unsubstituted 5 membered heterocycloalkyl.

In embodiments, $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl. In embodiments, $R^1$ and $R^2$ may optionally be joined to form a substituted or unsubstituted 3 to 6 membered heterocycloalkyl or substituted or unsubstituted 5 to 6 membered heteroaryl.

In embodiments, $R^1$ is independently hydrogen, oxo, halogen, —$CX^1_3$, —$CHX^1_2$, —$CH_2X^1$, —$OCX^1_3$, —$OCHX^1_2$, —$OCH_2X^1$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. In embodiments, $R^1$ is independently oxo, halogen, —$CX^1_3$, —$CHX^1_2$, —$CH_2X^1$, —$OCX^1_3$, —$OCHX^1_2$, —$OCH_2X^1$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. In embodiments, $R^1$ is independently oxo, halogen, —$CX^1_3$, —$CHX^1_2$, —$CH_2X^1$, —$OCX^1_3$, —$OCHX^1_2$, —$OCH_2X^1$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^1$ is independently halogen. In embodiments, $X^1$ is independently —F or —Cl.

$R^{30}$ is independently oxo, halogen, —$CX^{30}_3$, —$CHX^{30}_2$, —$CH_2X^{30}$, —$OCH_2X^{30}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{30}_3$, —$OCHX^{30}_2$, $R^{31}$-substituted or unsubstituted alkyl, $R^{31}$-substituted or unsubstituted heteroalkyl, $R^{31}$-substituted or unsubstituted cycloalkyl, $R^3$-substituted or unsubstituted heterocycloalkyl, $R^3$-substituted or unsubstituted aryl, or $R^3$-substituted or unsubstituted heteroaryl. In embodiments, $R^{30}$ is independently oxo, halogen, —$CX^{30}_3$, —$CHX^{30}_2$, —$CH_2X^{30}$, —$OCH_2X^{30}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{30}_3$, —$OCHX^{30}_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $X^{30}$ is independently halogen. In embodiments, $X^{30}$ is independently —F or —Cl. In embodiments, $R^{30}$ is substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

$R^{31}$ is independently oxo, halogen, —$CX^{31}_3$, —$CHX^{31}_2$, —$CH_2X^{31}$, —$OCH_2X^{31}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{31}_3$, —$OCHX^{31}_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^{31}$ is independently oxo, halogen, —$CX^{31}_3$, —$CHX^{31}_2$, —$CH_2X^{31}$, —$OCH_2X^{31}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)

NHNH$_2$, —NHC=(O)NH$_2$, —NHSO$_2$H, —NHC=(O)H, —NHC(O)—OH, —NHOH, —OCX$^{31}$$_3$, —OCHX$^{31}$$_2$, unsubstituted alkyl, unsubstituted heteroalkyl, unsubstituted cycloalkyl, unsubstituted heterocycloalkyl, unsubstituted aryl, or unsubstituted heteroaryl. X$^{31}$ is independently halogen. In embodiments, X$^{31}$ is independently —F or —Cl.

In embodiments, R$^1$ is independently hydrogen, halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl. In embodiments, R$^1$ is independently halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

In embodiments, R$^1$ is independently halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, R$^{30}$-substituted or unsubstituted (C$_1$-C$_5$) alkyl, R$^{30}$-substituted or unsubstituted 2 to 5 membered heteroalkyl, R$^{30}$-substituted or unsubstituted (C$_3$-C$_6$) cycloalkyl, or R$^{30}$-substituted or unsubstituted 3 to 6 membered heterocycloalkyl. In embodiments, R$^1$ is unsubstituted (C$_1$-C$_3$) alkyl. In embodiments, R$^1$ is unsubstituted (C$_1$-C$_2$) alkyl. In embodiments, R$^1$ is R$^{30}$-substituted or unsubstituted (C$_1$-C$_2$) alkyl; R$^{30}$ is independently halogen, —OH, —NH$_2$, —SH, substituted or unsubstituted (C$_1$-C$_3$) alkyl, substituted or unsubstituted 2 to 3 membered heteroalkyl, or substituted or unsubstituted cyclopropyl; and X$^{30}$ is independently halogen. In embodiments, R$^1$ is unsubstituted methyl. In embodiments, R$^1$ is R$^{30}$-substituted or unsubstituted (C$_1$-C$_3$) alkyl or R$^{30}$-substituted or unsubstituted 2 to 3 membered heteroalkyl. In embodiments, R$^1$ is independently hydrogen. In embodiments, R$^1$ is a R$^{30}$-substituted methyl. In embodiments, R$^1$ is a R$^{30}$-substituted ethyl. In embodiments, R$^1$ is R$^{30}$-substituted or unsubstituted 2 to 5 membered heteroalkyl. In embodiments, R$^1$ is R$^{30}$-substituted or unsubstituted 3 membered heteroalkyl. In embodiments, R$^1$ is R$^{30}$-substituted or unsubstituted 2 to 5 membered heteroalkyl. In embodiments, R$^1$ is 9-ethyl-9H-fluorene. In embodiments, R$^1$ is 9-fluoromethoxycarbonyl. In embodiments, R$^1$ is

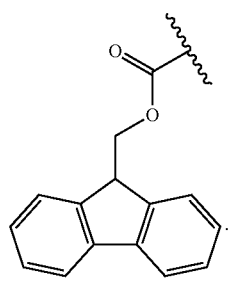 [SMILES: *C(=O)OCC1c2ccccc2-c2ccccc21]

In embodiments, R$^{30}$ is independently oxo, halogen, —CX$^{30}$$_3$, —CHX$^{30}$$_2$, —CH$_2$X$^{30}$, —OCHX$^{30}$$_2$, —OCX$^{30}$$_3$, —OCH$_2$X$^{30}$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted (C$_1$-C$_5$) alkyl, substituted or unsubstituted 2 to 5 membered heteroalkyl, substituted or unsubstituted (C$_3$-C$_5$) cycloalkyl, substituted or unsubstituted 3 to 5 membered heterocycloalkyl, substituted or unsubstituted phenyl, or substituted or unsubstituted 5 to 6 membered heteroaryl. X$^{30}$ is independently halogen. In embodiments, R$^{30}$ is —Cl. In embodiments, R$^{30}$ is —OH.

In embodiments, R$^{30}$ is independently oxo, halogen, —CX$^{30}$$_3$, —CHX$^{30}$$_2$, —CH$_2$X$^{30}$, —OCHX$^{30}$$_2$, —OCX$^{30}$$_3$, —OCH$_2$X$^{30}$, —CN, —N$_3$, —OH, —NH$_2$, —COOH, —CONH$_2$, —NO$_2$, —SH, —SO$_2$NH$_2$, —NHNH$_2$, —ONH$_2$, —NHOH, substituted or unsubstituted (C$_1$-C$_3$) alkyl, substituted or unsubstituted 2 to 3 membered heteroalkyl, or substituted or unsubstituted cyclopropyl. X$^{30}$ is independently halogen. In embodiments, R$^{30}$ is unsubstituted cyclopropyl. In embodiments, R$^{30}$ is unsubstituted cyclobutyl. In embodiments, R$^{30}$ is unsubstituted cyclopentyl. In embodiments, R$^{30}$ is unsubstituted cyclohexyl. In embodiments, R$^{30}$ is substituted or unsubstituted phenyl. In embodiments, R$^{30}$ is unsubstituted phenyl. In embodiments, R$^{30}$ is unsubstituted benzyl.

In embodiments, R$^{30}$ is independently oxo, halogen, —CX$^{30}$$_3$, —CHX$^{30}$$_2$, —CH$_2$X$^{30}$, —OCHX$^{30}$$_2$, —OCX$^{30}$$_3$, —OCH$_2$X$^{30}$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted (C$_1$-C$_3$) alkyl, or substituted or unsubstituted 2 to 3 membered heteroalkyl. In embodiments, r100 is independently oxo, halogen, —OH, —NH$_2$, —COOH, —CONH$_2$, —NO$_2$, —SH, substituted or unsubstituted (C$_1$-C$_3$) alkyl, or substituted or unsubstituted 2 to 3 membered heteroalkyl. X$^{30}$ is independently halogen.

In embodiments, R$^2$ is hydrogen, halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F. In embodiments, R$^2$ is substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl. In embodiments, R$^2$ is hydrogen.

In embodiments, R$^2$ is independently hydrogen, halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted (C$_1$-C$_5$) alkyl, substituted or unsubstituted 2 to 5 membered heteroalkyl, substituted or unsubstituted (C$_3$-C$_6$) cycloalkyl, or substituted or unsubstituted 3 to 6 membered heterocycloalkyl.

In embodiments, R$^2$ is substituted or unsubstituted (C$_1$-C$_{12}$) alkyl. In embodiments, R$^2$ is unsubstituted (C$_1$-C$_2$) alkyl. In embodiments, R$^2$ is substituted (C$_1$-C$_{12}$) alkyl, substituted with a substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

In embodiments, $R^2$ and $R^3$ may optionally be joined to form a substituted or unsubstituted 3 to 6 membered heterocycloalkyl or substituted or unsubstituted 3 to 6 membered heteroaryl. In embodiments, $R^2$ and $R^3$ may optionally be joined to form a substituted or unsubstituted 4 to 6 membered heterocycloalkyl or substituted or unsubstituted 4 to 6 membered heteroaryl. In embodiments, $R^2$ and $R^3$ may optionally be joined to form a substituted or unsubstituted 5 to 6 membered heterocycloalkyl or substituted or unsubstituted 5 to 6 membered heteroaryl. In embodiments, $R^2$ and $R^3$ may optionally be joined to form a substituted or unsubstituted 5 membered heterocycloalkyl or substituted or unsubstituted 5 membered heteroaryl. In embodiments, $R^2$ and $R^3$ may optionally be joined to form a substituted or unsubstituted 6 membered heterocycloalkyl or substituted or unsubstituted 6 membered heteroaryl. $R^2$ and $R^3$ may optionally be joined to form a substituted or unsubstituted 3 to 6 membered heterocycloalkyl or substituted or unsubstituted 5 to 6 membered heteroaryl.

In embodiments, $R^2$ is independently hydrogen, oxo, halogen, $-CX^2_3$, $-CHX^2_2$, $-CH_2X^2$, $-OCH_2X^2$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. In embodiments, $R^2$ is independently oxo, halogen, $-CX^2_3$, $-CHX^2_2$, $-CH_2X^2$, $-OCH_2X^2$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX^2_3$, $-OCHX^2_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. In embodiments, $R^2$ is independently oxo, halogen, $-CX^2_3$, $-CHX^2_2$, $-CH_2X^2$, $-OCH_2X^2$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^2_3$, $-OCHX^2_2$, unsubstituted alkyl, unsubstituted heteroalkyl, unsubstituted cycloalkyl, unsubstituted heterocycloalkyl, unsubstituted aryl, or unsubstituted heteroaryl. $X^2$ is independently halogen. In embodiments, $X^2$ is independently $-F$ or $-Cl$.

$R^{33}$ is independently oxo, halogen, $-CX^{33}_3$, $-CHX^{33}_2$, $-CH_2X^{33}$, $-OCHX^{33}_2$, $-OCX^{33}_3$, $-OCH_2X^{33}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. In embodiments, $R^{33}$ is independently oxo, halogen, $-CX^{33}_3$, $-CHX^{33}_2$, $-CH_2X^{33}$, $-OCHX^{33}_2$, $-OCX^{33}_3$, $-OCH_2X^{33}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{33}$ is independently halogen. In embodiments, $X^{33}$ is independently $-F$ or $-Cl$. In embodiments, $R^{33}$ is substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

$R^{34}$ is independently oxo, halogen, $-CX^{34}_3$, $-CHX^{34}_2$, $-CH_2X^{34}$, $-OCH_2X^{34}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{34}_3$, $-OCHX^{34}_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^{34}$ is independently oxo, halogen, $-CX^{34}_3$, $-CHX^{34}_2$, $-CH_2X^{34}$, $-OCH_2X^{34}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{34}_3$, $-OCHX^{34}_2$, unsubstituted alkyl, unsubstituted heteroalkyl, unsubstituted cycloalkyl, unsubstituted heterocycloalkyl, unsubstituted aryl, or unsubstituted heteroaryl. $X^{34}$ is independently halogen. In embodiments, $X^{34}$ is independently $-F$ or $-Cl$.

In embodiments, $R^2$ is independently hydrogen, halogen, $-CF_3$, $-CN$, $-N_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $-OCF_3$, $-OCHF_2$, $-OCH_2F$, substituted or unsubstituted $(C_1-C_5)$ alkyl, substituted or unsubstituted 2 to 5 membered heteroalkyl, substituted or unsubstituted $(C_3-C_6)$ cycloalkyl, or substituted or unsubstituted 3 to 6 membered heterocycloalkyl. In embodiments, $R^2$ is independently halogen, $-CF_3$, $-CN$, $-N_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $-OCF_3$, $-OCHF_2$, $-OCH_2F$, substituted or unsubstituted $(C_1-C_5)$ alkyl, substituted or unsubstituted 2 to 5 membered heteroalkyl, substituted or unsubstituted $(C_3-C_6)$ cycloalkyl, or substituted or unsubstituted 3 to 6 membered heterocycloalkyl.

In embodiments, $R^2$ is independently halogen, $-CF_3$, $-CN$, $-N_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $-OCF_3$, $-OCHF_2$, $-OCH_2F$, $R^{33}$-substituted or unsubstituted $(C_1-C_5)$ alkyl, $R^{33}$-substituted or unsubstituted 2 to 5 membered heteroalkyl, $R^{33}$-substituted or unsubstituted $(C_3-C_6)$ cycloalkyl, or $R^{33}$-substituted or unsubstituted 3 to 6 membered heterocycloalkyl. In embodiments, $R^2$ is $R^{33}$-substituted or unsubstituted ($C_1$-$C_3$) alkyl or $R^{33}$-substituted or unsubstituted 2 to 3 membered heteroalkyl. In embodiments, $R^2$ is unsubstituted ($C_1$-$C_3$) alkyl. In embodiments, $R^2$ is unsubstituted ($C_1$-$C_2$) alkyl. In embodiments, $R^2$ is $R^{33}$-substituted or unsubstituted ($C_1$-$C_2$) alkyl; $R^{33}$ is independently halogen, —OH, —$NH_2$, —SH, substituted or unsubstituted ($C_1$-$C_3$) alkyl, substituted or unsubstituted 2 to 3 membered heteroalkyl, or substituted or unsubstituted cyclopropyl. $X^{33}$ is independently halogen. In embodiments, $R^2$ is unsubstituted methyl. In embodiments, $R^2$ is independently hydrogen. In embodiments, $R^2$ is $R^{33}$-substituted or unsubstituted 2 to 5 membered heteroalkyl. In embodiments, $R^2$ is $R^{33}$-substituted or unsubstituted 3 membered heteroalkyl. In embodiments, $R^1$ is $R^{33}$-substituted or unsubstituted 2 to 5 membered heteroalkyl. In embodiments, $R^2$ is 9-ethyl-9H-fluorene. In embodiments, $R^2$ is 9-fluoromethoxycarbonyl. In embodiments, $R^2$ is

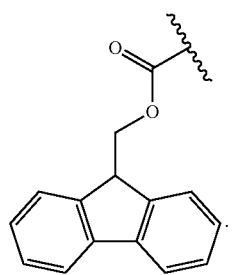 [SMILES: *C(=O)OCC1c2ccccc2-c2ccccc21]

In embodiments, $R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl. $X^{33}$ is independently halogen. In embodiments, $R^{33}$ is —Cl. In embodiments, $R^{33}$ is —OH.

In embodiments, $R^{33}$ is independently oxo, halogen, —$CX^{33}_3$, —$CHX^{33}_2$, —$CH_2X^{33}$, —$OCHX^{33}_2$, —$OCX^{33}_3$, —$OCH_2X^{33}$, —CN, —$N_3$, —OH, —$NH_2$, —COOH, —$CONH_2$, —$NO_2$, —SH, —$SO_2NH_2$, —$NHNH_2$, —$ONH_2$, —NHOH, substituted or unsubstituted ($C_1$-$C_3$) alkyl, substituted or unsubstituted 2 to 3 membered heteroalkyl, or substituted or unsubstituted cyclopropyl; and $X^{33}$ is independently halogen. heterocycloalkyl. In embodiments, $R^{33}$ is independently oxo, halogen, —$CX^{33}_3$, —$CHX^{33}_2$, $CH_2X^{33}$, —$OCX^{33}_3$, —$OCHX^{33}_2$, —$OCH_2X^{33}$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted ($C_1$-$C_5$) alkyl, substituted or unsubstituted 2 to 5 membered heteroalkyl, substituted or unsubstituted ($C_3$-$C_5$) cycloalkyl, substituted or unsubstituted 3 to 5 membered heterocycloalkyl, substituted or unsubstituted phenyl, or substituted or unsubstituted 5 to 6 membered heteroaryl; and $X^{33}$ is independently halogen. In embodiments, $R^{33}$ is unsubstituted cyclopropyl. In embodiments, $R^{33}$ is unsubstituted cyclobutyl. In embodiments, $R^{33}$ is unsubstituted cyclopentyl. In embodiments, $R^{33}$ is unsubstituted cyclohexyl. In embodiments, $R^{33}$ is substituted or unsubstituted phenyl. In embodiments, $R^{33}$ is unsubstituted phenyl. In embodiments, $R^{33}$ is unsubstituted benzyl.

In embodiments, $R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted ($C_1$-$C_3$) alkyl, or substituted or unsubstituted 2 to 3 membered heteroalkyl; and $X^{33}$ is independently halogen. In embodiments, $R^{33}$ is independently oxo, halogen, —OH, —$NH_2$, —COOH, —$CONH_2$, —$NO_2$, —SH, substituted or unsubstituted ($C_1$-$C_3$) alkyl, or substituted or unsubstituted 2 to 3 membered heteroalkyl; and $X^{33}$ is independently halogen.

In embodiments, $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —$N(O)_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_3$, —$CH_2X_3$, —$OCX_3$, —$OCHX_3$, —$OCH_2X^3$. In embodiments, $R^3$ is substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, two adjacent $R^3$ substituents may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^3$ is independently halogen, —$NHNR^7R^8$, —$ONR^7R^8$, —NHC=(O)$NHNR^7R^8$, —NHC=(O)$NR^7R^8$, —$N(O)_m$, —$NR^7R^8$, —C(O)$R^9$, —C(O)—$OR^9$, —C(O)$NR^7R^8$, —$OR^{10}$, —$NR^7C$=(O)$R^9$, —$NR^7C(O)OR^9$, or —$NR^7OR^9$. In embodiments, $R^3$ is independently halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted ($C_1$-$C_5$) alkyl, or substituted or unsubstituted 2 to 5 membered heteroalkyl.

In embodiments, $R^3$ is independently halogen. In embodiments, $R^3$ is independently —$CF_3$. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —NHC=(O)$NHNH_2$. In embodiments, $R^3$ is independently —NHC=(O)$NH_2$. In embodiments, $R^3$ is independently —NHC=(O)H. In embodiments, $R^3$ is independently —NHC(O)OH. In embodiments, $R^3$ is independently —NHOH. In embodiments, $R^3$ is independently halogen, —$CF_3$, —OH, —$NH_2$, —COOH, —$CONH_2$, —NHC=(O)$NHNH_2$, —NHC=(O)$NH_2$, —NHC=(O)H, —NHC(O)OH, or —NHOH. In embodiments, $R^3$ is —OH. In embodiments, $R^3$ is —$OCH_3$. In embodiments, $R^3$ is —$N_3$.

In embodiments, $R^1$ and $R^3$ may optionally be joined to form a substituted or unsubstituted 3 to 6 membered heterocycloalkyl. In embodiments, $R^1$ and $R^3$ may optionally be joined to form a substituted or unsubstituted 3 membered heterocycloalkyl. In embodiments, $R^1$ and $R^3$ may optionally be joined to form a substituted or unsubstituted 4 membered heterocycloalkyl. In embodiments, $R^1$ and $R^3$ may optionally be joined to form a substituted or unsubstituted 5 membered heterocycloalkyl. In embodiments, $R^1$ and $R^3$ may optionally be joined to form a substituted or unsubstituted 6 membered heterocycloalkyl. In embodiments, $R^1$ and $R^3$ may optionally be joined to form a substituted (e.g., substituted with a substituent group, a size-limited substituent group, or lower substituent group) or unsubstituted 3 to 6 membered heterocycloalkyl. In embodiments, $R^1$ and $R^3$ may optionally be joined to form a substituted (e.g., substituted with a substituent group, a size-limited substituent group, or lower substituent group) or unsubstituted 3 membered heterocycloalkyl. In embodiments, $R^1$ and $R^3$ may optionally be joined to form a substituted (e.g., substituted with a substituent group, a size-limited substituent group, or lower substituent group) or unsubstituted 4 membered heterocycloalkyl. In embodiments, $R^1$ and $R^3$ may optionally be joined to form a substituted (e.g., substituted with a substituent group, a size-limited substituent group, or lower substituent group) or unsubstituted 5 membered heterocycloalkyl. In embodiments, $R^1$ and $R^3$ may optionally be joined to form a substituted (e.g., substituted with a substituent group, a size-limited substituent group, or lower substituent group) or unsubstituted 6 membered heterocycloalkyl.

In embodiments, $R^2$ and $R^3$ may optionally be joined to form a substituted or unsubstituted 3 to 6 membered heterocycloalkyl. In embodiments, $R^2$ and $R^3$ may optionally be joined to form a substituted or unsubstituted 3 membered heterocycloalkyl. In embodiments, $R^2$ and $R^3$ may optionally be joined to form a substituted or unsubstituted 4 membered heterocycloalkyl. In embodiments, $R^2$ and $R^3$ may optionally be joined to form a substituted or unsubstituted 5 membered heterocycloalkyl. In embodiments, $R^2$ and $R^3$ may optionally be joined to form a substituted or unsubstituted 6 membered heterocycloalkyl. In embodiments, $R^2$ and $R^3$ may optionally be joined to form a substituted (e.g., substituted with a substituent group, a size-limited substituent group, or lower substituent group) or unsubstituted 3 to 6 membered heterocycloalkyl. In embodiments, $R^2$ and $R^3$ may optionally be joined to form a substituted (e.g., substituted with a substituent group, a size-limited substituent group, or lower substituent group) or unsubstituted 3 membered heterocycloalkyl. In embodiments, $R^2$ and $R^3$ may optionally be joined to form a substituted (e.g., substituted with a substituent group, a size-limited substituent group, or lower substituent group) or unsubstituted 4 membered heterocycloalkyl. In embodiments, $R^2$ and $R^3$ may optionally be joined to form a substituted (e.g., substituted with a substituent group, a size-limited substituent group, or lower substituent group) or unsubstituted 5 membered heterocycloalkyl. In embodiments, $R^2$ and $R^3$ may optionally be joined to form a substituted (e.g., substituted with a substituent group, a size-limited substituent group, or lower substituent group) or unsubstituted 6 membered heterocycloalkyl.

$R^3$ is independently hydrogen, halogen, —$CX_3$, —CN, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —$N(O)_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C$(O)$OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is independently hydrogen, oxo, halogen, —$CX^3_3$, —$CHX^3_2$, —$CH_2X^3$, —$OCH_2X^3$, —$OCX^3_3$, —$OCHX^3_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. In embodiments, $R^3$ is independently oxo, halogen, —$CX^3_3$, —$CHX^3_2$, —$CH_2X^3$, —$OCH_2X^3$, —$OCX^3_3$, —$OCHX^3_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. In embodiments, $R^3$ is independently oxo, halogen, —$CX^3_3$, —$CHX^3_2$, —$CH_2X^3$, —$OCH_2X^3$, —$OCX^3_3$, —$OCHX^3_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^3$ is independently halogen. In embodiments, $X^3$ is independently —F or —Cl.

$R^{36}$ is independently oxo, halogen, —$CX^{36}_3$, —$CHX^{36}_2$, —$CH_2X^{36}$, —$OCHX^{36}_2$, —$OCX^{36}_3$, —$OCH_2X^{36}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl. In embodiments, $R^{36}$ is independently oxo, halogen, —$CX^{36}_3$, —$CHX^{36}_2$, —$CH_2X^{36}$, —$OCHX^{36}_2$, —$OCX^{36}_3$, —$OCH_2X^{36}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{36}$ is independently halogen. In embodiments, $X^{36}$ is independently —F or —Cl.

$R^{37}$ is independently oxo, halogen, —$CX^{37}_3$, —$CHX^{37}_2$, —$CH_2X^{37}$, $OCH_2X^{37}$, —$OCX^{37}_3$, —$OCHX^{37}_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—$OH$, —$NHOH$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl. In embodiments, $R^{37}$ is independently oxo, halogen, —$CX^{37}{}_3$, —$CHX^{37}{}_2$, —$CH_2X^{37}$, $OCH_2X^{37}$, —$OCX^{37}{}_3$, —$OCHX^{37}{}_2$, —$CN$, —$N_3$, —$OH$, —$NH_2$, —$COOH$, —$CONH_2$, —$NO_2$, —$SH$, —$SO_2Cl$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—$OH$, —$NHOH$, unsubstituted alkyl, unsubstituted heteroalkyl, unsubstituted cycloalkyl, unsubstituted heterocycloalkyl, unsubstituted aryl, or unsubstituted heteroaryl. $X^{37}$ is independently halogen. In embodiments, $X^{37}$ is independently —F or —Cl.

$R^3$ may independently be halogen, —$CX_3$, —$CN$, —$N_3$, —$SO_nR^{10}$, —$SO_vNR^7R^8$, —$NHNR^7R^8$, —$ONR^7R^8$, —$NHC$=$(O)NHNR^7R^8$, —$NHC$=$(O)NR^7R^8$, —$N(O)_m$, —$NR^7R^8$, —$C(O)R^9$, —$C(O)$—$OR^9$, —$C(O)NR^7R^8$, —$OR^{10}$, —$NR^7SO_2R^{10}$, —$NR^7C$=$(O)R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen. In embodiments, $R^3$ is independently halogen. In embodiments, $R^3$ is independently —$CX_3$. In embodiments, $R^3$ is independently —$CN$. In embodiments, $R^3$ is independently —$SO_nR^{10}$. In embodiments, $R^3$ is independently —$SO_vNR^7R^8$. In embodiments, $R^3$ is independently —$NHNR^7R^8$. In embodiments, $R^3$ is independently —$ONR^7R^8$. In embodiments, $R^3$ is independently —$NHC$=$(O)NHNR^7R^8$. In embodiments, $R^3$ is independently —$NHC$=$(O)NR^7R^8$. In embodiments, $R^3$ is independently —$N(O)_m$. In embodiments, $R^3$ is independently —$NR^7R^8$. In embodiments, $R^3$ is independently —$C(O)R^9$. In embodiments, $R^3$ is independently —$C(O)$—$OR^9$. In embodiments, $R^3$ is independently —$C(O)NR^7R^8$. In embodiments, $R^3$ is independently —$OR^{10}$. In embodiments, $R^3$ is independently —$NRSO_2R^1$. In embodiments, $R^3$ is independently —$NR^7C$=$(O)R^9$. In embodiments, $R^3$ is independently —$NR^7C(O)OR^9$. In embodiments, $R^3$ is independently —$NR^7OR^9$. In embodiments, $R^3$ is independently —$CHX_2$. In embodiments, $R^3$ is independently —$CH_2X$. In embodiments, $R^3$ is independently —$CX_3$. In embodiments, $R^3$ is independently —$OCX_3$. In embodiments, $R^3$ is independently —$OCHX_2$. In embodiments, $R^3$ is independently —$OCH_2X$. In embodiments, $R^3$ is independently substituted or unsubstituted alkyl. In embodiments, $R^3$ is independently substituted or unsubstituted heteroalkyl. In embodiments, $R^3$ is independently substituted or unsubstituted cycloalkyl. In embodiments, $R^3$ is independently substituted or unsubstituted heterocycloalkyl. In embodiments, $R^3$ is independently substituted or unsubstituted aryl. In embodiments, $R^3$ is independently substituted or unsubstituted heteroaryl. In embodiments, $R^3$ is substituted alkyl. In embodiments, $R^3$ is substituted heteroalkyl. In embodiments, $R^3$ is independently substituted cycloalkyl. In embodiments, $R^3$ is independently substituted heterocycloalkyl. In embodiments, $R^3$ is independently substituted aryl. In embodiments, $R^3$ is independently substituted heteroaryl. In embodiments, $R^3$ is independently unsubstituted alkyl. In embodiments, $R^3$ is independently unsubstituted heteroalkyl. In embodiments, $R^3$ is independently unsubstituted cycloalkyl. In embodiments, $R^3$ is independently unsubstituted heterocycloalkyl. In embodiments, $R^3$ is independently unsubstituted aryl. In embodiments, $R^3$ is independently unsubstituted heteroaryl.

In embodiments, $R^3$ is independently hydrogen, halogen, —$CF_3$, —$CN$, —$N_3$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)OH$, —$NHOH$, —$CHF_2$, —$CH_2F$, —$OCF_3$, —$OCHF_2$, —$OCH_2F$, substituted or unsubstituted ($C_1$-$C_5$) alkyl, or substituted or unsubstituted 2 to 5 membered heteroalkyl. In embodiments, $R^3$ is independently halogen, —$CF_3$, —$CN$, —$N_3$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)OH$, —$NHOH$, —$CHF_2$, —$CH_2F$, —$OCF_3$, —$OCHF_2$, —$OCH_2F$, substituted or unsubstituted ($C_1$-$C_5$) alkyl, or substituted or unsubstituted 2 to 5 membered heteroalkyl.

In embodiments, $R^3$ is independently halogen. In embodiments, $R^3$ is independently —$CF_3$. In embodiments, $R^3$ is independently —$CN$. In embodiments, $R^3$ is independently —$OH$. In embodiments, $R^3$ is independently —$NH_2$. In embodiments, $R^3$ is independently —$COOH$. In embodiments, $R^3$ is independently —$CONH_2$. In embodiments, $R^3$ is independently —$NO_2$. In embodiments, $R^3$ is independently —$SH$. In embodiments, $R^3$ is independently —$SO_3H$. In embodiments, $R^3$ is independently —$SO_4H$. In embodiments, $R^3$ is independently —$SO_2NH_2$. In embodiments, $R^3$ is independently —$NHNH_2$. In embodiments, $R^3$ is independently —$ONH_2$. In embodiments, $R^3$ is independently —$NHC$=$(O)NHNH_2$. In embodiments, $R^3$ is independently —$NHC$=$(O)NH_2$. In embodiments, $R^3$ is independently —$NHSO_2H$. In embodiments, $R^3$ is independently —$NHC$=$(O)H$. In embodiments, $R^3$ is independently —$NHC(O)OH$. In embodiments, $R^3$ is independently —$NHOH$. In embodiments, $R^3$ is independently —$CHF_2$. In embodiments, $R^3$ is independently —$CH_2F$. In embodiments, $R^3$ is independently —$CF_3$. In embodiments, $R^3$ is independently —$OCF_3$. In embodiments, $R^3$ is independently —$OCH_2F$. In embodiments, $R^3$ is independently —$OCHF_2$. In embodiments, $R^3$ is independently substituted or unsubstituted ($C_1$-$C_5$) alkyl. In embodiments, $R^3$ is independently substituted or unsubstituted 2 to 5 membered heteroalkyl. In embodiments, $R^3$ is independently substituted ($C_1$-$C_5$) alkyl. In embodiments, $R^3$ is independently substituted 2 to 5 membered heteroalkyl. In embodiments, $R^3$ is independently unsubstituted ($C_1$-$C_5$) alkyl. In embodiments, $R^3$ is independently unsubstituted 2 to 5 membered heteroalkyl. In embodiments, $R^3$ is independently substituted or unsubstituted butyl. In embodiments, $R^3$ is independently substituted or unsubstituted butoxy. In embodiments, $R^3$ is independently substituted butyl. In embodiments, $R^3$ is independently substituted butoxy. In embodiments, $R^3$ is independently unsubstituted butyl. In embodiments, $R^3$ is independently unsubstituted butoxy. In embodiments, $R^3$ is independently substituted or unsubstituted propyl. In embodiments, $R^3$ is independently substituted or unsubstituted propoxy. In embodiments, $R^3$ is independently substituted propyl. In embodiments, $R^3$ is independently substituted propoxy. In embodiments, $R^3$ is independently unsubstituted propyl. In embodiments, $R^3$ is independently unsubstituted propoxy. In embodiments, $R^3$ is independently substituted or unsubstituted ethyl. In embodiments, $R^3$ is independently substituted or unsubstituted ethoxy. In embodiments, $R^3$ is independently substituted ethyl. In embodiments, $R^3$ is independently substituted ethoxy. In embodiments, $R^3$ is independently unsubstituted ethyl. In embodiments, $R^3$ is independently unsubstituted ethoxy. In embodiments, $R^3$ is independently substituted or unsubstituted methyl. In embodiments, $R^3$ is independently substituted or unsubstituted methoxy. In embodiments, $R^3$ is independently substituted methyl. In embodiments, $R^3$ is independently substituted methoxy. In embodiments, $R^3$ is independently unsubstituted methyl. In embodiments, $R^3$ is independently unsubstituted methoxy. In embodiments, $R^3$ is independently hydrogen.

In embodiments, two adjacent $R^3$ substituents may optionally be joined to form a substituted or unsubstituted ($C_3$-$C_{10}$) cycloalkyl or substituted or unsubstituted 3 to 10 membered heterocycloalkyl, substituted or unsubstituted ($C_6$-$C_{10}$) aryl, or substituted or unsubstituted 5 to 10 membered heteroaryl. In embodiments, two adjacent $R^3$ substituents may optionally be joined to form a substituted or unsubstituted ($C_3$-$C_{10}$) cycloalkyl. In embodiments, two adjacent $R^3$ substituents may optionally be joined to form substituted or unsubstituted 3 to 10 membered heterocycloalkyl. In embodiments, two adjacent $R^3$ substituents may optionally be joined to form substituted or unsubstituted ($C_6$-$C_{10}$) aryl. In embodiments, two adjacent $R^3$ substituents may optionally be joined to form substituted or unsubstituted 5 to 10 membered heteroaryl. In embodiments, two adjacent $R^3$ substituents may optionally be joined to form a substituted (e.g., substituted with a substituent group, a size-limited substituent group, or lower substituent group) or unsubstituted ($C_3$-$C_{10}$) cycloalkyl. In embodiments, two adjacent $R^3$ substituents may optionally be joined to form a substituted (e.g., substituted with a substituent group, a size-limited substituent group, or lower substituent group) or unsubstituted 3 to 10 membered heterocycloalkyl. In embodiments, two adjacent $R^3$ substituents may optionally be joined to form a substituted (e.g., substituted with a substituent group, a size-limited substituent group, or lower substituent group) or unsubstituted ($C_6$-$C_{10}$) aryl. In embodiments, two adjacent $R^3$ substituents may optionally be joined to form a substituted (e.g., substituted with a substituent group, a size-limited substituent group, or lower substituent group) or unsubstituted 5 to 10 membered heteroaryl. In embodiments, two adjacent $R^3$ substituents may optionally be joined to form 2,2-dimethyl-1,3-dioxanyl. In embodiments, two adjacent $R^3$ substituents may optionally be joined to form 1,3-dioxanyl. In embodiments, two adjacent $R^3$ substituents may optionally be joined to form 1,3-dioxolanyl. In embodiments, two adjacent $R^3$ substituents may optionally be joined to form 2,2-dimethyl-1,3-dioxolanyl.

In embodiments, $R^7$ is hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^8$ is hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^9$ is hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10}$ is hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

$R^7$ and $R^8$ substituents bonded to the same nitrogen atom may optionally be joined to form a substituted or unsubstituted heterocycloalkyl or substituted or unsubstituted heteroaryl.

Each $R^7$, $R^8$, $R^9$, and $R^{10}$ is independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^7$ and $R^8$ substituents bonded to the same nitrogen atom may optionally be joined to form a substituted or unsubstituted 4 to 6 membered heterocycloalkyl or substituted or unsubstituted 5 to 6 membered heteroaryl.

Each $R^7$ and $R^8$ substituents bonded to the same nitrogen atom may be joined to form a substituted or unsubstituted heterocycloalkyl or substituted or unsubstituted heteroaryl. Each $R^7$ and $R^8$ substituents bonded to the same nitrogen atom may be joined to form an unsubstituted heterocycloalkyl or unsubstituted heteroaryl. Each $R^7$ and $R^8$ substituents bonded to the same nitrogen atom may be joined to form a substituted or unsubstituted 4 to 6 membered heterocycloalkyl or 5 to 6 membered heteroaryl. Each $R^7$ and $R^8$ substituents bonded to the same nitrogen atom may be joined to form an unsubstituted 4 to 6 membered heterocycloalkyl or unsubstituted 5 to 6 membered heteroaryl. In embodiments, each $R^7$ and $R^8$ substituents bonded to the same nitrogen atom may be joined to form a substituted (e.g., substituted with a substituent group, a size-limited substituent group, or lower substituent group) or unsubstituted 4 to 6 membered heterocycloalkyl or substituted (e.g., substituted with a substituent group, a size-limited substituent group, or lower substituent group) or unsubstituted 5 to 6 membered heteroaryl. In embodiments, each $R^7$ and $R^8$ substituents bonded to the same nitrogen atom may be joined to form a substituted (e.g., substituted with a substituent group, a size-limited substituent group, or lower substituent group) or unsubstituted 4 to 6 membered heterocycloalkyl. In embodiments, each $R^7$ and $R^8$ substituents bonded to the same nitrogen atom may be joined to form a substituted (e.g., substituted with a substituent group, a size-limited substituent group, or lower substituent group) or unsubstituted 5 to 6 membered heteroaryl.

In embodiments, $R^7$ is independently hydrogen, oxo, halogen, —$CX^7_3$, —$CHX^7_2$, —$CH_2X^7$, —$OCX^7_3$, —$OCHX^7_2$, —$OCH_2X^7$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl. In embodiments, $R^7$ is independently oxo, halogen, —$CX^7_3$, —$CHX^7_2$, —$CH_2X^7$, —$OCX^7_3$, —$OCHX^7_2$, —$OCH_2X^7$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl. In embodiments, $R^7$ is independently oxo, halogen, —$CX^7_3$, —$CHX^7_2$, —$CH_2X^7$, —$OCX^7_3$, —$OCHX^7_2$, —$OCH_2X^7$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^7$ is independently halogen. In embodiments, $X^7$ is independently —F or —Cl. In embodiments, $R^7$ is independently —$CH_3$.

$R^{48}$ is independently oxo, halogen, —$CX^{48}_3$, —$CHX^{48}_2$, —$CH_2X^{48}$, —$OCHX^{48}_2$, —$OCX^{48}_3$, —$OCH_2X^{48}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl. In embodiments, $R^{48}$ is independently oxo, halogen, —$CX^{48}_3$, —$CHX^{48}_2$, —$CH_2X^{48}$, —$OCHX^{48}_2$, —$OCX^{48}_3$, —$OCH_2X^{48}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{48}$ is independently halogen. In embodiments, $X^{48}$ is independently —F or —Cl.

$R^{49}$ is independently oxo, halogen, —$CX^{49}_3$, —$CHX^{49}_2$, —$CH_2X^{49}$, —$OCX^{49}_3$, —$OCHX^{49}_2$, —$OCH_2X^{49}$, —CN, —$N_3$, —OH, —$NH_2$, —COOH, $CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl. In embodiments, $R^{49}$ is independently oxo, halogen, —$CX^{49}_3$, —$CHX^{49}_2$, —$CH_2X^{49}$, —$OCX^{49}_3$, —$OCHX^{49}_2$, —$OCH_2X^{49}$, —CN, —$N_3$, —OH, —$NH_2$, —COOH, $CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{49}$ is independently halogen. In embodiments, $X^{49}$ is independently —F or —Cl.

In embodiments, $R^8$ is independently hydrogen, oxo, halogen, —$CX^8_3$, —$CHX^8_2$, —$CH_2X^8$, —$OCX^8_3$, —$OCHX^8_2$, —$OCH_2X^8$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^8_3$, —$OCHX^8_2$, $R^{51}$-substituted or unsubstituted alkyl, $R^{51}$-substituted or unsubstituted heteroalkyl, $R^{51}$-substituted or unsubstituted cycloalkyl, $R^{51}$-substituted or unsubstituted heterocycloalkyl, $R^{51}$-substituted or unsubstituted aryl, or $R^{51}$-substituted or unsubstituted heteroaryl. In embodiments, $R^8$ is independently oxo, halogen, —$CX^8_3$, —$CHX^8_2$, —$CH_2X^8$, —$OCX^8_3$, —$OCHX^8_2$, —$OCH_2X^8$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —OCX$^8_3$, —OCHX$^8_2$, R$^{51}$-substituted or unsubstituted alkyl, R$^{51}$-substituted or unsubstituted heteroalkyl, R$^{51}$-substituted or unsubstituted cycloalkyl, R$^{51}$-substituted or unsubstituted heterocycloalkyl, R$^{51}$-substituted or unsubstituted aryl, or R$^{51}$-substituted or unsubstituted heteroaryl. In embodiments, R$^8$ is independently oxo, halogen, —CX$^8_3$, —CHX$^8_2$, —CH$_2$X$^8$, —OCX$^8_3$, —OCHX$^8_2$, —OCH$_2$X$^8$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^8_3$, —OCHX$^8_2$, unsubstituted alkyl, unsubstituted heteroalkyl, unsubstituted cycloalkyl, unsubstituted heterocycloalkyl, unsubstituted aryl, or unsubstituted heteroaryl. X$^8$ is independently halogen. In embodiments, X$^8$ is independently —F or —Cl. In embodiments, R$^8$ is independently —CH$_3$.

R$^{51}$ is independently oxo, halogen, —CX$^{51}_3$, —CHX$^{51}_2$, —CH$_2$X$^{51}$, —OCHX$^{51}_2$, —OCX$^{51}_3$, —OCH$_2$X$^{51}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{52}$-substituted or unsubstituted alkyl, R$^{52}$-substituted or unsubstituted heteroalkyl, R$^{52}$-substituted or unsubstituted cycloalkyl, R$^{52}$-substituted or unsubstituted heterocycloalkyl, R$^{52}$-substituted or unsubstituted aryl, or R$^{52}$-substituted or unsubstituted heteroaryl. In embodiments, R$^{51}$ is independently oxo, halogen, —CX$^{51}_3$, —CHX$^{51}_2$, —CH$_2$X$^{51}$, —OCHX$^{51}_2$, —OCX$^{51}_3$, —OCH$_2$X$^{51}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^{51}$ is independently halogen. In embodiments, X$^{51}$ is independently —F or —Cl.

R$^{52}$ is independently oxo, halogen, —CX$^{52}_3$, —CHX$^{52}_2$, —CH$_2$X$^{52}$, —OCX$^{52}_3$, —OCHX$^{52}_2$, —OCH$_2$X$^{52}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{53}$-substituted or unsubstituted alkyl, R$^{53}$-substituted or unsubstituted heteroalkyl, R$^{53}$-substituted or unsubstituted cycloalkyl, R$^{53}$-substituted or unsubstituted heterocycloalkyl, R$^{53}$-substituted or unsubstituted aryl, or R$^{53}$-substituted or unsubstituted heteroaryl. In embodiments, R$^{52}$ is independently oxo, halogen, —CX$^{52}_3$, —CHX$^{52}_2$, —CH$_2$X$^{52}$, —OCX$^{52}_3$, —OCHX$^{52}_2$, —OCH$_2$X$^{52}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^{52}$ is independently halogen. In embodiments, X$^{52}$ is independently —F or —Cl.

In embodiments, R$^9$ is independently hydrogen, oxo, halogen, —CX$^9_3$, —CHX$^9_2$, —CH$_2$X$^9$, —OCX$^9_3$, —OCHX$^9_2$, —OCH$_2$X$^9$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{54}$-substituted or unsubstituted alkyl, R$^{54}$-substituted or unsubstituted heteroalkyl, R$^{54}$-substituted or unsubstituted cycloalkyl, R$^{54}$-substituted or unsubstituted heterocycloalkyl, R$^{54}$-substituted or unsubstituted aryl, or R$^{54}$-substituted or unsubstituted heteroaryl. In embodiments, R$^9$ is independently oxo, halogen, —CX$^9_3$, —CHX$^9_2$, —CH$_2$X$^9$, —OCX$^9_3$, —OCHX$^9_2$, —OCH$_2$X$^9$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{54}$-substituted or unsubstituted alkyl, R$^{54}$-substituted or unsubstituted heteroalkyl, R$^{54}$-substituted or unsubstituted cycloalkyl, R$^{54}$-substituted or unsubstituted heterocycloalkyl, R$^{54}$-substituted or unsubstituted aryl, or R$^{54}$-substituted or unsubstituted heteroaryl. In embodiments, R$^9$ is independently —CH$_3$. In embodiments, R$^9$ is independently oxo, halogen, —CX$^9_3$, —CHX$^9_2$, —CH$_2$X$^9$, —OCX$^9_3$, —OCHX$^9_2$, —OCH$_2$X$^9$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^9$ is independently halogen. In embodiments, X$^9$ is independently —F or —Cl.

R$^{54}$ is independently oxo, halogen, —CX$^{54}_3$, —CHX$^{54}_2$, —CH$_2$X$^{54}$, —OCHX$^{54}_2$, —OCX$^{54}_3$, —OCH$_2$X$^{54}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{55}$-substituted or unsubstituted alkyl, R$^{55}$-substituted or unsubstituted heteroalkyl, R$^{55}$-substituted or unsubstituted cycloalkyl, R$^{55}$-substituted or unsubstituted heterocycloalkyl, R$^{55}$-substituted or unsubstituted aryl, or R$^{55}$-substituted or unsubstituted heteroaryl. In embodiments, R$^{54}$ is independently oxo, halogen, —CX$^{54}_3$, —CHX$^{54}_2$, —CH$_2$X$^{54}$, —OCHX$^{54}_2$, —OCX$^{54}_3$, —OCH$_2$X$^{54}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^{54}$ is independently halogen. In embodiments, X$^{54}$ is independently —F or —Cl.

R$^{55}$ is independently oxo, halogen, —CX$^{55}_3$, —CHX$^{55}_2$, —CH$_2$X$^{55}$, —OCX$^{55}_3$, —OCHX$^{55}_2$, —OCH$_2$X$^{55}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{56}$-substituted or unsubstituted alkyl, R$^{56}$-substituted or unsubstituted heteroalkyl, R$^{56}$-substituted or unsubstituted cycloalkyl, R$^{56}$-substituted or unsubstituted heterocycloalkyl, R$^{56}$-substituted or unsubstituted aryl, or R$^{56}$-substituted or unsubstituted heteroaryl. In embodiments, R$^{55}$ is independently oxo, halogen, —CX$^{55}_3$, —CHX$^{55}_2$, —CH$_2$X$^{55}$, —OCX$^{55}_3$, —OCHX$^{55}_2$, —OCH$_2$X$^{55}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{55}$ is independently halogen. In embodiments, $X^{55}$ is independently —F or —Cl.

In embodiments, $R^{10}$ is independently hydrogen, oxo, halogen, —$CX^{10}_3$, —$CHX^{10}_2$, —$CH_2X^{10}$, —$OCX^{10}_3$, —$OCHX^{10}_2$, —$OCH_2X^{10}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl. In embodiments, $R^{10}$ is independently oxo, halogen, —$CX^{10}_3$, —$CHX^{10}_2$, —$CH_2X^{10}$, —$OCX^{10}_3$, —$OCHX^{10}_2$, —$OCH_2X^{10}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{57}$-substituted or unsubstituted alkyl, $R^{57}$-substituted or unsubstituted heteroalkyl, $R^{57}$-substituted or unsubstituted cycloalkyl, $R^{57}$-substituted or unsubstituted heterocycloalkyl, $R^{57}$-substituted or unsubstituted aryl, or $R^{57}$-substituted or unsubstituted heteroaryl. In embodiments, $R^{10}$ is independently oxo, halogen, —$CX^{10}_3$, —$CHX^{10}_2$, —$CH_2X^{10}$, —$OCX^{10}_3$, —$OCHX^{10}_2$, —$OCH_2X^{10}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{10}$ is independently halogen. In embodiments, $X^{10}$ is independently —F or —Cl. In embodiments, $R°$ is independently —$CH_3$.

$R^{57}$ is independently oxo, halogen, —$CX^{57}_3$, —$CHX^{57}_2$, —$CH_2X^{57}$, —$OCX^{57}_3$, —$OCHX^{57}_2$, —$OCH_2X^{57}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl. In embodiments, $R^{57}$ is independently oxo, halogen, —$CX^{57}_3$, —$CHX^{57}_2$, —$CH_2X^{57}$, —$OCX^{57}_3$, —$OCHX^{57}_2$, —$OCH_2X^{57}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{57}$ is independently halogen. In embodiments, $X^{57}$ is independently —F or —Cl.

$R^{58}$ is independently oxo, halogen, —$CX^{58}_3$, —$CHX^{58}_2$, —$CH_2X^{58}$, —$OCX^{58}_3$, —$OCHX^{58}_2$, —$OCH_2X^{58}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl. In embodiments, $R^{58}$ is independently oxo, halogen, —$CX^{58}_3$, —$CHX^{58}_2$, —$CH_2X^{58}$, —$OCX^{58}_3$, —$OCHX^{58}_2$, —$OCH_2X^{58}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{58}$ is independently halogen. In embodiments, $X^{58}$ is independently —F or —Cl.

$R^4$ is independently oxo, halogen, —$CX^a_3$, —CN, —$N_3$, $SO_{n1}R^{14}$, —$SO_{v1}NR^{11}R^{12}$, —$NHNR^{11}R^{12}$, —$ONR^{11}R^{12}$, —NHC=(O)NHNR$^{11}$R$^{12}$, —NHC=(O)NR$^{11}$R$^{12}$, —$N(O)_m$, —$NR^{11}R^{12}$, —$C(O)R^{13}$, —C(O)—$OR^{13}$, —$C(O)NR^{11}R^{12}$, —$OR^{14}$, —$NR^{11}SO_2R^{14}$, —$NR^{11}C$=(O)$R^{13}$, —$NR^{11}C(O)OR^{13}$, —$NR^{11}OR^{13}$, —$CHX^a_2$, —$CH_2X^a$, —$OCX^a_3$, —$OCHX^a_2$, —$OCH_2X^a$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl. $R^{11}$, $R^{12}$, $R^{13}$, and $R^{14}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)OH, —NHOH, —$CHF_2$, —$CH_2F$, —$OCF_3$, —$OCHF_2$, —$OCH_2F$, substituted or unsubstituted alkyl (e.g., $C_1$-$C_5$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). $R^{11}$ and $R^{12}$ substituents bonded to the same nitrogen atom may optionally be joined to form a substituted or unsubstituted heterocycloalkyl or substituted or unsubstituted heteroaryl; m1 and v1 are independently 1 or 2; n1 is independently an integer from 0 to 4; and $X^a$ is independently —Cl, —Br, —I, or —F. In embodiments, $R^4$ is halogen or —$OCH_3$.

$R^4$ is independently hydrogen, oxo, halogen, —$CX^a_3$, —CN, —$N_3$, —$SO_{n1}R^{14}$, —$SO_{v1}NR^{11}R^{12}$, —$NHNR^{11}R^{12}$, —$ONR^{11}R^{12}$, —NHC=(O)NHNR$^{11}$R$^{12}$, —NHC=(O)NR$^{11}$R$^{12}$, —$N(O)_{m1}$, —$NR^{11}R^{12}$, —$C(O)R^{13}$, —C(O)—$OR^{13}$, —$C(O)NR^{11}R^{12}$, —$OR^{14}$, —$NR^{11}SO_2R^{14}$, —$NR^{11}C$=(O)$R^{13}$, —$NR^{11}C(O)OR^{13}$, —$NR^{11}OR^{13}$, —$CHX^a_2$, —$CH_2X^a$, —$OCX^a_3$, —$OCHX^a_2$, —$OCH_2X^a$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl.

In embodiments, $R^4$ is unsubstituted methyl. In embodiments, $R^4$ is unsubstituted ethyl. In embodiments, $R^4$ is unsubstituted propyl. In embodiments, $R^4$ is unsubstituted methoxy. In embodiments, $R^4$ is unsubstituted ethoxy. In embodiments, $R^4$ is unsubstituted propoxy. In embodiments, $R^4$ is oxo. In embodiments, $R^4$ is unsubstituted phenyl. In embodiments, $R^4$ is unsubstituted benzyl.

In embodiments, $R^4$ is independently hydrogen, oxo, halogen, —$CX^{43}$, —$CHX^{42}$, —$CH_2X^4$, —$OCX^{43}$, —$OCHX^{42}$, —$OCH_2X^4$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. In embodiments, $R^4$ is independently oxo, halogen, —$CX^{43}$, —$CHX^{42}$, —$CH_2X^4$, —$OCX^{43}$, —$OCHX^{42}$, —$OCH_2X^4$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. In embodiments, $R^4$ is independently oxo, halogen, —$CX^{43}$, —$CHX^{42}$, —$CH_2X^4$, —$OCX^{43}$, —$OCHX^{42}$, —$OCH_2X^4$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^4$ is independently halogen. In embodiments, $X^4$ is independently —F or —Cl.

In embodiments, $R^4$ is $R^{39}$-substituted methyl. In embodiments, $R^4$ is $R^{39}$-substituted ethyl. In embodiments, $R^4$ is substituted or unsubstituted 2 to 20 membered heteroalkyl. In embodiments, $R^4$ is substituted or unsubstituted 2 to 20 membered heteroalkyl. In embodiments, $R^4$ is substituted or unsubstituted 2 to 15 membered heteroalkyl. In embodiments, $R^4$ is

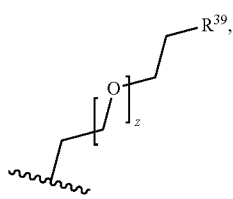

wherein z is an integer from 1 to 10. In embodiments, $R^4$ is

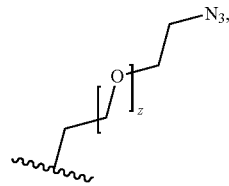

wherein z is an integer from 1 to 10. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9. In embodiments, z is 10. In embodiments, $R^4$ is

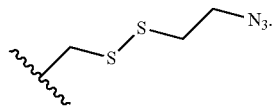 [SMILES: *CSSCCN=[N+]=[N-]]

$R^{39}$ is independently oxo, halogen, —$CX^{39}_3$, —$CHX^{39}_2$, —$CH_2X^{39}$, —$OCHX^{39}_2$, —$OCH_2X^{39}$, —$OCX^{39}_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, —$OCX^{39}_3$, —$OCHX^{39}_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. In embodiments, $R^{39}$ is independently oxo, halogen, —$CX^{39}_3$, —$CHX^{39}_2$, —$CH_2X^{39}$, —$OCHX^{39}_2$, —$OCH_2X^{39}$, —$OCX^{39}_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, —$OCX^{39}_3$, —$OCHX^{39}_2$, unsubstituted alkyl, unsubstituted heteroalkyl, unsubstituted cycloalkyl, unsubstituted heterocycloalkyl, unsubstituted aryl, or unsubstituted heteroaryl. $X^{39}$ is independently halogen. In embodiments, $X^{39}$ is independently —F or —Cl.

In embodiments, $R^{39}$ is substituted or unsubstituted ($C_1$-$C_5$) alkyl, substituted or unsubstituted 2 to 5 membered heteroalkyl, substituted or unsubstituted ($C_3$-$C_6$) cycloalkyl, or substituted or unsubstituted 3 to 6 membered heterocycloalkyl substituted or unsubstituted 3 to 6 membered heterocycloalkyl or substituted or unsubstituted 5 to 6 membered heteroaryl. In embodiments, $R^{39}$ is $N_3$. In embodiments, $R^{39}$ is unsubstituted phenyl. In embodiments, $R^{39}$ is unsubstituted benzyl.

$R^{40}$ is independently oxo, halogen, —$CX^{40}_3$, —$CHX^{40}_2$, —$CH_2X^{40}$, —$OCX^{40}_3$, —$OCHX^{40}_2$, —$OCH_2X^{40}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$N_3$, —NHC=(O)$NHNH_2$, —NHC=(O)$NH_2$, —$NHSO_2H$, —NHC=(O)H, —NHC(O)—OH, —NHOH, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl. In embodiments, $R^{40}$ is independently oxo, halogen, $-CX^{40}{}_3$, $-CHX^{40}{}_2$, $-CH_2X^{40}$, $-OCX^{40}{}_3$, $-OCHX^{40}{}_2$, $-OCH_2X^{40}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-N_3$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{40}$ is independently halogen. In embodiments, $X^{40}$ is independently $-F$ or $-Cl$. In embodiments, $R^{40}$ is $N_3$.

In embodiments, $R^4$ is independently oxo, halogen, $-CX^a{}_3$, $-CN$, $-N_3$, $-SO_{n1}R^{14}$, $-SO_{v}NR^{11}R^{12}$, $-NHNR^{11}R^{12}$, $-ONR^{11}R^{12}$, $-NHC=(O)NHNR^{11}R^{12}$, $-NHC=(O)NR^{11}R^{12}$, $-N(O)_{m1}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C=(O)R^{13}$, $-NR^{11}C(O)OR^{13}$, $-NR^{11}R^{13}$, $-CHX^a{}_2$, $-CH_2X^a$, $-OCX^a{}_3$, $-OCHX^a{}_2$, $-OCH_2X^a$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is independently hydrogen. In embodiments, $R^4$ is independently oxo. In embodiments, $R^4$ is independently halogen. In embodiments, $R^4$ is independently $-CX^a{}_3$. In embodiments, $R^4$ is independently $-CN$. In embodiments, $R^4$ is independently $-SO_nR^{14}$. In embodiments, $R^4$ is independently $-SO_{v1}NR^{11}R^{12}$. In embodiments, $R^4$ is independently $-NHNR^{11}R^{12}$. In embodiments, $R^4$ is independently $-ONR^{11}R^{12}$. In embodiments, $R^4$ is independently $-NHC=(O)NHNR^{11}R^{12}$. In embodiments, $R^4$ is independently $-NHC=(O)NR^{11}R^{12}$. In embodiments, $R^4$ is independently $-N(O)_{m1}$. In embodiments, $R^4$ is independently $-NR^{11}R^{12}$. In embodiments, $R^4$ is independently $-C(O)R^{13}$. In embodiments, $R^4$ is independently $-C(O)-OR^{13}$. In embodiments, $R^4$ is independently $-C(O)NR^{11}R^{12}$. In embodiments, $R^4$ is independently $-OR^{14}$. In embodiments, $R^4$ is independently $-NR^{11}SO_2R^{14}$. In embodiments, $R^4$ is independently $-NR^{11}C=(O)R^{13}$. In embodiments, $R^4$ is independently $-NR^{11}C(O)OR^{13}$. In embodiments, $R^4$ is independently $-NR^{11}OR^{13}$. In embodiments, $R^4$ is independently $-CHX^a{}_2$. In embodiments, $R^4$ is independently $-CH_2X^a$. In embodiments, $R^4$ is independently $-OCX^a{}_3$. In embodiments, $R^4$ is independently $-OCHX^a{}_2$.

In embodiments, $R^4$ is independently substituted or unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently substituted or unsubstituted heterocycloalkyl. In embodiments, $R^4$ is independently substituted or unsubstituted aryl. In embodiments, $R^4$ is independently substituted or unsubstituted heteroaryl. In embodiments, $R^4$ is independently substituted alkyl. In embodiments, $R^4$ is independently substituted heteroalkyl. In embodiments, $R^4$ is independently substituted cycloalkyl. In embodiments, $R^4$ is independently substituted heterocycloalkyl. In embodiments, $R^4$ is substituted independently aryl. In embodiments, $R^4$ is independently substituted heteroaryl. In embodiments, $R^4$ is independently unsubstituted alkyl. In embodiments, $R^4$ is independently unsubstituted heteroalkyl. In embodiments, $R^4$ is independently unsubstituted cycloalkyl. In embodiments, $R^4$ is independently unsubstituted heterocycloalkyl. In embodiments, $R^4$ is independently unsubstituted aryl. In embodiments, $R^4$ is independently unsubstituted heteroaryl.

In embodiments, $R^4$ is independently hydrogen, halogen, $-CF_3$, $-CN$, $-N_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $-OCF_3$, $-OCHF_2$, $-OCH_2F$, substituted or unsubstituted ($C_1$-$C_5$) alkyl, or substituted or unsubstituted 2 to 5 membered heteroalkyl. In embodiments, $R^4$ is independently halogen, $-CF_3$, $-CN$, $-N_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $-OCF_3$, $-OCHF_2$, $-OCH_2F$, substituted or unsubstituted ($C_1$-$C_5$) alkyl, or substituted or unsubstituted 2 to 5 membered heteroalkyl. In embodiments, $R^4$ is methyl.

In embodiments, $R^4$ is independently halogen, $-CF_3$, $-CN$, $-N_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-CHF_2$, $-CH_2F$, $-OCF_3$, $-OCHF_2$, $-OCH_2F$, substituted or unsubstituted ($C_1$-$C_5$) alkyl, or substituted or unsubstituted 2 to 5 membered heteroalkyl. In embodiments, $R^4$ is independently halogen. In embodiments, $R^4$ is independently $-CF_3$. In embodiments, $R^4$ is independently $-CN$. In embodiments, $R^4$ is independently $-OH$. In embodiments, $R^4$ is independently $-NH_2$. In embodiments, $R^4$ is independently $-COOH$. In embodiments, $R^4$ is independently $-CONH_2$. In embodiments, $R^4$ is independently $-NO_2$. In embodiments, $R^4$ is independently $-SH$. In embodiments, $R^4$ is independently $-SO_3H$. In embodiments, $R^4$ is independently $-SO_4H$. In embodiments, $R^4$ is independently $-SO_2NH_2$. In embodiments, $R^4$ is independently $-NHNH_2$. In embodiments, $R^4$ is independently $-ONH_2$. In embodiments, $R^4$ is independently $-NHC=(O)NHNH_2$. In embodiments, $R^4$ is independently $-NHC=(O)NH_2$. In embodiments, $R^4$ is independently $-NHSO_2H$. In embodiments, $R^4$ is independently $-NHC=(O)H$. In embodiments, $R^4$ is independently $-NHC(O)OH$. In embodiments, $R^4$ is independently $-NHOH$. In embodiments, $R^4$ is independently $-CHF_2$. In embodiments, $R^4$ is independently $-CH_2F$. In embodiments, $R^4$ is independently $-OCF_3$. In embodiments, $R^4$ is independently $-OCHF_2$. In embodiments, $R^4$ is independently $-OCH_2F$.

In embodiments, $R^4$ is independently substituted or unsubstituted ($C_1$-$C_5$) alkyl. In embodiments, $R^4$ is independently substituted or unsubstituted 2 to 5 membered heteroalkyl. In embodiments, $R^4$ is independently substituted ($C_1$-$C_5$) alkyl. In embodiments, $R^4$ is independently substituted 2 to 5 membered heteroalkyl. In embodiments, $R^4$ is independently unsubstituted ($C_1$-$C_5$) alkyl. In embodiments, $R^4$ is independently unsubstituted 2 to 5 membered heteroalkyl. In embodiments, $R^4$ is independently substituted or unsubstituted butyl. In embodiments, $R^4$ is independently substituted or unsubstituted butoxy. In embodiments, $R^4$ is independently substituted butyl. In embodiments, $R^4$ is independently substituted butoxy. In embodiments, $R^4$ is independently unsubstituted butyl. In embodiments, $R^4$ is independently unsubstituted butoxy. In embodiments, $R^4$ is independently substituted or unsubstituted propyl. In embodiments, $R^4$ is independently substituted or unsubstituted propoxy. In embodiments, $R^4$ is independently substituted propyl. In embodiments, $R^4$ is independently substituted propoxy. In embodiments, $R^4$ is independently unsubstituted propyl. In embodiments, $R^4$ is independently unsubstituted propoxy. In embodiments, $R^4$ is independently substituted or unsubstituted ethyl. In embodiments, $R^4$ is independently substituted or unsubstituted ethoxy. In embodiments, $R^4$ is independently substituted ethyl. In embodiments, $R^4$ is independently substituted ethoxy. In embodiments, $R^4$ is independently unsubstituted ethyl. In embodiments, $R^4$ is independently unsubstituted ethoxy. In embodiments, $R^4$ is independently substituted or unsubstituted methyl. In embodiments, $R^4$ is independently substituted or unsubstituted methoxy. In embodiments, $R^4$ is independently substituted methyl. In embodiments, $R^4$ is independently substituted methoxy. In embodiments, $R^4$ is independently unsubstituted methyl. In embodiments, $R^4$ is independently unsubstituted methoxy. In embodiments, $R^4$ is independently hydrogen. In embodiments, $R^4$ is independently unsubstituted methoxy. In embodiments, $R^4$ is independently halogen. In embodiments, $R^4$ is F.

In embodiments, two adjacent $R^4$ substituents are joined to form a substituted or unsubstituted cycloalkyl. In embodiments, two adjacent $R^4$ substituents are joined to form a substituted or unsubstituted heterocycloalkyl. In embodiments, two adjacent $R^4$ substituents are joined to form a substituted or unsubstituted aryl. In embodiments, two adjacent $R^4$ substituents are joined to form a substituted or unsubstituted heteroaryl. In embodiments, two adjacent $R^4$ substituents are joined to form a substituted or unsubstituted $(C_3-C_6)$ cycloalkyl. In embodiments, two adjacent $R^4$ substituents are joined to form a substituted or unsubstituted 3 to 6 membered heterocycloalkyl. In embodiments, two adjacent $R^4$ substituents are joined to form a substituted or unsubstituted $(C_6-C_{10})$ aryl. In embodiments, two adjacent $R^4$ substituents are joined to form a substituted or unsubstituted 5 to 10 membered heteroaryl. In embodiments, two adjacent $R^4$ substituents are joined to form a substituted (e.g., substituted with a substituent group, a size-limited substituent group, or lower substituent group) or unsubstituted $(C_3-C_6)$ cycloalkyl. In embodiments, two adjacent $R^4$ substituents are joined to form a substituted (e.g., substituted with a substituent group, a size-limited substituent group, or lower substituent group) or unsubstituted 3 to 6 membered heterocycloalkyl. In embodiments, two adjacent $R^4$ substituents are joined to form a substituted (e.g., substituted with a substituent group, a size-limited substituent group, or lower substituent group) or unsubstituted $(C_6-C_{10})$ aryl. In embodiments, two adjacent $R^3$ substituents are joined to form a substituted (e.g., substituted with a substituent group, a size-limited substituent group, or lower substituent group) or unsubstituted 5 to 10 membered heteroaryl. In embodiments, two adjacent $R^4$ substituents are joined to form a substituted or unsubstituted phenyl. In embodiments, two adjacent $R^4$ substituents are joined to form a substituted or unsubstituted 5 to 9 membered heteroaryl. In embodiments, two adjacent $R^4$ substituents are joined to form a substituted or unsubstituted naphthyl. In embodiments, two adjacent $R^4$ substituents are joined to form a substituted or unsubstituted 5 to 6 membered heteroaryl. In embodiments, two adjacent $R^4$ substituents are joined to form a substituted cycloalkyl. In embodiments, two adjacent $R^4$ substituents are joined to form a substituted heterocycloalkyl. In embodiments, two adjacent $R^4$ substituents are joined to form a substituted aryl. In embodiments, two adjacent $R^4$ substituents are joined to form a substituted heteroaryl. In embodiments, two adjacent $R^4$ substituents are joined to form a substituted $(C_3-C_6)$ cycloalkyl. In embodiments, two adjacent $R^4$ substituents are joined to form a substituted 3 to 6 membered heterocycloalkyl. In embodiments, two adjacent $R^4$ substituents are joined to form a substituted $(C_6-C_{10})$ aryl. In embodiments, two adjacent $R^4$ substituents are joined to form a substituted 5 to 10 membered heteroaryl. In embodiments, two adjacent $R^4$ substituents are joined to form a substituted phenyl. In embodiments, two adjacent $R^4$ substituents are joined to form a substituted 5 to 9 membered heteroaryl. In embodiments, two adjacent $R^4$ substituents are joined to form a substituted naphthyl. In embodiments, two adjacent $R^4$ substituents are joined to form a substituted 5 to 6 membered heteroaryl. In embodiments, two adjacent $R^4$ substituents are joined to form an unsubstituted cycloalkyl. In embodiments, two adjacent $R^4$ substituents are joined to form an unsubstituted heterocycloalkyl. In embodiments, two adjacent $R^4$ substituents are joined to form an unsubstituted aryl. In embodiments, two adjacent $R^4$ substituents are joined to form an unsubstituted heteroaryl. In embodiments, two adjacent $R^4$ substituents are joined to form an unsubstituted $(C_3-C_6)$ cycloalkyl. In embodiments, two adjacent $R^4$ substituents are joined to form an unsubstituted 3 to 6 membered heterocycloalkyl. In embodiments, two adjacent $R^4$ substituents are joined to form an unsubstituted $(C_6-C_{10})$ aryl. In embodiments, two adjacent $R^4$ substituents are joined to form an unsubstituted 5 to 10 membered heteroaryl. In embodiments, two adjacent $R^4$ substituents are joined to form an unsubstituted phenyl. In embodiments, two adjacent $R^4$ substituents are joined to form an unsubstituted 5 to 9 membered heteroaryl. In embodiments, two adjacent $R^4$ substituents are joined to form an unsubstituted naphthyl. In embodiments, two adjacent $R^4$ substituents are joined to form an unsubstituted 5 to 6 membered heteroaryl.

$R^{11}$, $R^{12}$, $R^{13}$, and $R^{14}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; m1 and v1 are independently 1 or 2; n1 is independently an integer from 0 to 4; $X^a$ is independently —Cl, —Br, —I, or —F.

Each $R^{11}$ and $R^{12}$ substituents bonded to the same nitrogen atom may be joined to form a substituted or unsubstituted heterocycloalkyl or substituted or unsubstituted heteroaryl. Each $R^{11}$ and $R^{12}$ substituents bonded to the same nitrogen atom may be joined to form an unsubstituted heterocycloalkyl or unsubstituted heteroaryl. Each $R^{11}$ and $R^{12}$ substituents bonded to the same nitrogen atom may be joined to form a substituted or unsubstituted 4 to 6 membered heterocycloalkyl or substituted or unsubstituted 5 to 6 membered heteroaryl. Each $R^{11}$ and $R^{12}$ substituents bonded to the same nitrogen atom may be joined to form an unsubstituted 4 to 6 membered heterocycloalkyl or unsubstituted 5 to 6 membered heteroaryl. In embodiments, each $R^{11}$ and $R^{12}$ substituents bonded to the same nitrogen atom may be joined to form a substituted (e.g., substituted with a substituent group, a size-limited substituent group, or lower substituent group) or unsubstituted 4 to 6 membered heterocycloalkyl or substituted (e.g., substituted with a substituent group, a size-limited substituent group, or lower substituent group) or unsubstituted 5 to 6 membered heteroaryl. In embodiments, each $R^{11}$ and $R^{12}$ substituents bonded to the same nitrogen atom may be joined to form a substituted (e.g., substituted with a substituent group, a size-limited substituent group, or lower substituent group) or unsubstituted 4 to 6 membered heterocycloalkyl. In embodiments, each $R^{11}$ and $R^{12}$ substituents bonded to the same nitrogen atom may be joined to form a substituted (e.g., substituted with a substituent group, a size-limited substituent group, or lower substituent group) or unsubstituted 5 to 6 membered heteroaryl.

In embodiments, $R^{11}$ is independently hydrogen, oxo, halogen, $-CX^{11}_3$, $-CHX^{11}_2$, $-CH_2X^{11}$, $-OCX^{11}_3$, $-OCHX^{11}_2$, $-OCH_2X^{11}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl. In embodiments, $R^{11}$ is independently oxo, halogen, $-CX^{11}_3$, $-CHX^{11}_2$, $-CH_2X^{11}$, $-OCX^{11}_3$, $-OCHX^{11}_2$, $-OCH_2X^{11}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl. In embodiments, $R^{11}$ is independently oxo, halogen, $-CX^{11}_3$, $-CHX^{11}_2$, $-CH_2X^{11}$, $-OCX^{11}_3$, $-OCHX^{11}_2$, $-OCH_2X^{11}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{11}$ is independently halogen. In embodiments, $X^{11}$ is independently $-F$ or $-Cl$.

$R^{60}$ is independently oxo, halogen, $-CX^{60}_3$, $-CHX^{60}_2$, $-CH_2X^{60}$, $-OCHX^{60}_2$, $-OCX^{60}_3$, $-OCH_2X^{60}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl. In embodiments, $R^{60}$ is independently oxo, halogen, $-CX^{60}_3$, $-CHX^{60}_2$, $-CH_2X^{60}$, $-OCHX^{60}_2$, $-OCX^{60}_3$, $-OCH_2X^{60}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{60}$ is independently halogen. In embodiments, $X^{60}$ is independently $-F$ or $-Cl$.

$R^{61}$ is independently oxo, halogen, $-CX^{61}_3$, $-CHX^{61}_2$, $-CH_2X^{61}$, $-OCX^{61}_3$, $-OCHX^{61}_2$, $-OCH_2X^{61}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl. In embodiments, $R^{61}$ is independently oxo, halogen, $-CX^{61}_3$, $-CHX^{61}_2$, $-CH_2X^{61}$, $-OCX^{61}_3$, $-OCHX^{61}_2$, $-OCH_2X^{61}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{61}$ is independently halogen. In embodiments, $X^{61}$ is independently $-F$ or $-Cl$.

In embodiments, $R^{12}$ is independently hydrogen, oxo, halogen, $-CX^{12}_3$, $-CHX^{12}_2$, $-CH_2X^{12}$, $-OCX^{12}_3$, $-OCHX^{12}_2$, $-OCH_2X^{12}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl. In embodiments, $R^{12}$ is independently oxo, halogen, $-CX^{12}_3$, $-CHX^{12}_2$, $-CH_2X^{12}$, $-OCX^{12}_3$, $-OCHX^{12}_2$, $-OCH_2X^{12}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl. In embodiments, $R^{12}$ is independently oxo, halogen, $-CX^{12}_3$, $-CHX^{12}_2$, $-CH_2X^{12}$, $-OCX^{12}_3$, $-OCHX^{12}_2$, $-OCH_2X^{12}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{12}$ is independently halogen. In embodiments, $X^{12}$ is independently $-F$ or $-Cl$.

$R^{63}$ is independently oxo, halogen, $-CX^{63}_3$, $-CHX^{63}_2$, $-CH_2X^{63}$, $-OCHX^{63}_2$, $-OCX^{63}_3$, $-OCH_2X^{63}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl. In embodiments, $R^{63}$ is independently oxo, halogen, $-CX^{63}_3$, $-CHX^{63}_2$, $-CH_2X^{63}$, $-OCHX^{63}_2$, $-OCX^{63}_3$, $-OCH_2X^{63}$, $-CN$, $-N_3$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl. $X^{63}$ is independently halogen. In embodiments, $X^{63}$ is independently —F or —Cl.

$R^{64}$ is independently oxo, halogen, —$CX^{64}_3$, —$CHX^{64}_2$, —$CH_2X^{64}$, —$OCX^{64}_3$, —$OCHX^{64}_2$, —$OCH_2X^{64}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl. In embodiments, $R^{64}$ is independently oxo, halogen, —$CX^{64}_3$, —$CHX^{64}_2$, —$CH_2X^{64}$, —$OCX^{64}_3$, —$OCHX^{64}_2$, —$OCH_2X^{64}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{64}$ is independently halogen. In embodiments, $X^{64}$ is independently —F or —Cl.

In embodiments, $R^{13}$ is independently hydrogen, oxo, halogen, —$CX^{13}_3$, —$CHX^{13}_2$, —$CH_2X^{13}$, —$OCX^{13}_3$, —$OCHX^{13}_2$, —$OCH_2X^{13}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{13}_3$, —$OCHX^{13}_2$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl. In embodiments, $R^{13}$ is independently oxo, halogen, —$CX^{13}_3$, —$CHX^{13}_2$, —$CH_2X^{13}$, —$OCX^{13}_3$, —$OCHX^{13}_2$, —$OCH_2X^{13}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{13}_3$, —$OCHX^{13}_2$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl. In embodiments, $R^{13}$ is independently oxo, halogen, —$CX^{13}_3$, —$CHX^{13}_2$, —$CH_2X^{13}$, —$OCX^{13}_3$, —$OCHX^{13}_2$, —$OCH_2X^{13}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{13}_3$, —$OCHX^{13}_2$, unsubstituted alkyl, unsubstituted heteroalkyl, unsubstituted cycloalkyl, unsubstituted heterocycloalkyl, unsubstituted aryl, or unsubstituted heteroaryl. $X^{13}$ is independently halogen. In embodiments, $X^{13}$ is independently —F or —Cl.

$R^{66}$ is independently oxo, halogen, —$CX^{66}_3$, —$CHX^{66}_2$, —$CH_2X^{66}$, —$OCX^{66}_3$, —$OCHX^{66}_2$, —$OCH_2X^{66}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl. In embodiments, $R^{66}$ is independently oxo, halogen, —$CX^{66}_3$, —$CHX^{66}_2$, —$CH_2X^{66}$, —$OCX^{66}_3$, —$OCHX^{66}_2$, —$OCH_2X^{66}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{66}$ is independently halogen. In embodiments, $X^{66}$ is independently —F or —Cl.

$R^{67}$ is independently oxo, halogen, —$CX^{67}_3$, —$CHX^{67}_2$, —$CH_2X^{67}$, —$OCX^{67}_3$, —$OCHX^{67}_2$, —$OCH_2X^{67}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{68}$-substituted or unsubstituted alkyl, $R^{68}$-substituted or unsubstituted heteroalkyl, $R^{68}$-substituted or unsubstituted cycloalkyl, $R^{68}$-substituted or unsubstituted heterocycloalkyl, $R^{68}$-substituted or unsubstituted aryl, or $R^{68}$-substituted or unsubstituted heteroaryl. In embodiments, $R^{67}$ is independently oxo, halogen, —$CX^{67}_3$, —$CHX^{67}_2$, —$CH_2X^{67}$, —$OCX^{67}_3$, —$OCHX^{67}_2$, —$OCH_2X^{67}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{67}$ is independently halogen. In embodiments, $X^{67}$ is independently —F or —Cl.

In embodiments, $R^{14}$ is independently hydrogen, oxo, halogen, —$CX^{14}_3$, —$CHX^{14}_2$, —$CH_2X^{14}$, —$OCX^{14}_3$, —$OCHX^{14}_2$, —$OCH_2X^{14}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl. In embodiments, $R^{14}$ is independently oxo, halogen, —$CX^{14}_3$, —$CHX^{14}_2$, —$CH_2X^{14}$, —$OCX^{14}_3$, —$OCHX^{14}_2$, —$OCH_2X^{14}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl. In embodiments, $R^{14}$ is independently oxo, halogen, —$CX^{14}_3$, —$CHX^{14}_2$, —$CH_2X^{14}$, —$OCX^{14}_3$, —$OCHX^{14}_2$, —$OCH_2X^{14}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{14}$ is independently halogen. In embodiments, $X^{14}$ is independently —F or —Cl.

$R^{69}$ is independently oxo, halogen, —$CX^{69}_3$, —$CHX^{69}_2$, —$CH_2X^{69}$, —$OCX^{69}_3$, —$OCHX^{69}_2$, —$OCH_2X^{69}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl. In embodiments, $R^{69}$ is independently oxo, halogen, —$CX^{69}_3$, —$CHX^{69}_2$, —$CH_2X^{69}$, —$OCX^{69}_3$, —$OCHX^{69}_2$, —$OCH_2X^{69}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{69}$ is independently halogen. In embodiments, $X^{69}$ is independently —F or —Cl.

$R^{70}$ is independently oxo, halogen, —$CX^{70}_3$, —$CHX^{70}_2$, —$CH_2X^{70}$, —$OCX^{70}_3$, —$OCHX^{70}_2$, —$OCH_2X^{70}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl. In embodiments, $R^{70}$ is independently oxo, halogen, —$CX^{70}_3$, —$CHX^{70}_2$, —$CH_2X^{70}$, —$OCX^{70}_3$, —$OCHX^{70}_2$, —$OCH_2X^{70}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{70}$ is independently halogen. In embodiments, $X^{70}$ is independently —F or —Cl.

Each $R^7$, $R^8$, $R^9$, $R^{10}$, $R^{11}$, $R^{12}$, $R^{13}$, and $R^{14}$ may independently be hydrogen, halogen, —$CF_3$, —$CHF_2$, —$CH_2F$, —$OCF_3$, —$OCHF_2$, —$OCH_2F$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each $R^7$, $R^8$, $R^9$, $R^{10}$, $R^{11}$, $R^{12}$, $R^{13}$, and $R^{14}$ may independently be hydrogen, unsubstituted alkyl, unsubstituted heteroalkyl, unsubstituted cycloalkyl, unsubstituted heterocycloalkyl, unsubstituted aryl, or unsubstituted heteroaryl. Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

Each $R^7$, $R^8$, $R^9$, $R^{10}$, $R^{11}$, $R^{12}$, $R^{13}$, and $R^{14}$ may independently be hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$ aryl, or substituted or unsubstituted 5 to 6 membered heteroaryl. Each $R^7$, $R^8$, $R^9$, $R^{10}$, $R^{11}$, $R^{12}$, $R^{13}$, and $R^{14}$ may independently be hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl.

In embodiments, $R^5$ is hydrogen. In embodiments, $R^5$ is —$CF_3$. In embodiments, $R^5$ is —CN. In embodiments, $R^5$ is —COOH. In embodiments, $R^5$ is —$CONH_2$. In embodiments, $R^5$ is —$CHF_2$. In embodiments, $R^5$ is —$CH_2F$. In embodiments, $R^5$ is substituted or unsubstituted ($C_1$-$C_5$) alkyl or substituted or unsubstituted 2 to 5 membered heteroalkyl. $R^5$ is substituted or unsubstituted ($C_1$-$C_5$) alkyl. $R^5$ is unsubstituted ($C_1$-$C_5$) alkyl. $R^5$ is unsubstituted ($C_1$-$C_3$) alkyl. $R^5$ is unsubstituted methyl. In embodiments, $R^5$ is hydrogen. In embodiments, $R^5$ is propenyl. In embodiments, $R^5$ is ethenyl.

In embodiments, $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl. In embodiments, $R^5$ is hydrogen. In embodiments, $R^5$ is an unsubstituted methyl. In embodiments, $R^5$ is an unsubstituted ethyl. In embodiments, $R^5$ is an unsubstituted isopropyl. In embodiments, $R^5$ is an unsubstituted propyl. In embodiments, $R^5$ is an unsubstituted t-butyl. In embodiments, $R^5$ is an unsubstituted ethenyl. In embodiments, $R^5$ is an unsubstituted propenyl.

In embodiments, $R^5$ is independently hydrogen, oxo, halogen, —$CX^{53}$, —$CHX^{52}$, —$CH_2X^5$, —$OCX^{53}$, —$OCHX^{52}$, —$OCH_2X^5$, —CN, —$N_3$, —OH, —$NH_2$, —COO H, —$CONH_2$, —$NO_2$, —SH, —$SO_2Cl$, —$SO_3H$, —$SO_4H$, —$SO_2NH_2$, —$NHNH_2$, —$ONH_2$, —NHC=(O) $NHNH_2$, —NHC=(O)$NH_2$, —$NHSO_2H$, —NHC=(O)H, —NHC(O)—OH, —NHOH, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl. In embodiments, $R^5$ is independently oxo, halogen, —$CX^{53}$, —$CHX^5_2$, —$CH_2X^5$, —$OCX^{53}$, —$OCHX^5_2$, —$OCH_2X^5$, —CN, —$N_3$, —OH, —$NH_2$, —COO H, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl. In embodiments, $R^5$ is independently oxo, halogen, —$CX^{53}$, —$CHX^{52}$, —$CH_2X^5$, —$OCX^{53}$, —$OCHX^{52}$, —$OCH_2X^5$, —CN, —$N_3$, —OH, —$NH_2$, —COO H, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^5$ is independently halogen. In embodiments, X$^5$ is independently —F or —Cl.

R$^{42}$ is independently oxo, halogen, —CX$^{42}_3$, —CHX$^{42}_2$, —CH$_2$X$^{42}$, —OCHX$^{42}_2$, —OCX$^{42}_3$, —OCH$_2$X$^{42}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl, or R$^{43}$-substituted or unsubstituted heteroaryl. R$^{42}$ is independently oxo, halogen, —CX$^{42}_3$, —CHX$^{42}_2$, —CH$_2$X$^{42}$, —OCHX$^{42}_2$, —OCX$^{42}_3$, —OCH$_2$X$^{42}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. In embodiments, X$^{42}$ is independently halogen. In embodiments, X$^{42}$ is independently —F or —Cl.

R$^{43}$ is independently oxo, halogen, —CX$^{43}_3$, —CHX$^{43}_2$, —CH$_2$X$^{43}$, —OCX$^{43}_3$, —OCHX$^{43}_2$, —OCH$_2$X$^{43}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl. In embodiments, R$^{43}$ is independently oxo, halogen, —CX$^{43}_3$, —CHX$^{43}_2$, —CH$_2$X$^{43}$, —OCX$^{43}_3$, —OCHX$^{43}_2$, —OCH$_2$X$^{43}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^{43}$ is independently halogen. In embodiments, X$^{43}$ is independently —F or —Cl.

In embodiments, R$^6$ is hydrogen. In embodiments, R$^6$ is —CF$_3$. In embodiments, R$^6$ is —CN. In embodiments, R$^6$ is —COOH. In embodiments, R$^6$ is —CONH$_2$. In embodiments, R$^6$ is —CHF$_2$. In embodiments, R$^6$ is —CH$_2$F. In embodiments, R$^6$ is substituted or unsubstituted (C$_1$-C$_5$) alkyl, or substituted or unsubstituted 2 to 5 membered heteroalkyl.

In embodiments, R$^6$ is hydrogen. In embodiments, R$^6$ is substituted or unsubstituted (C$_1$-C$_5$) alkyl or substituted or unsubstituted 2 to 5 membered heteroalkyl. In embodiments, R$^6$ is substituted or unsubstituted (C$_1$-C$_5$) alkyl. In embodiments, R$^6$ is unsubstituted (C$_1$-C$_5$) alkyl. In embodiments, R$^6$ is unsubstituted (C$_1$-C$_3$) alkyl. In embodiments, R$^6$ is unsubstituted methyl.

In embodiments, R$^6$ is independently hydrogen, oxo, halogen, —CX$^{63}_3$, —CHX$^{62}_2$, —CH$_2$X$^6$, —OCX$^{63}_3$, —OCHX$^{62}_2$, —OCH$_2$X$^6$, —CN, —N$_3$, —OH, —NH$_2$, —COO H, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=(O)H, —NHC(O)—OH, —NHOH, R$^{45}$-substituted or unsubstituted alkyl, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl. In embodiments, R$^6$ is independently oxo, halogen, —CX$^{63}_3$, —CHX$^{62}_2$, —CH$_2$X$^6$, —OCX$^{63}_3$, —OCHX$^{62}_2$, —OCH$_2$X$^6$, —CN, —N$_3$, —OH, —NH$_2$, —COO H, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{45}$-substituted or unsubstituted alkyl, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl. In embodiments, R$^6$ is independently oxo, halogen, —CX$^{63}_3$, —CHX$^{62}_2$, —CH$_2$X$^6$, —OCX$^{63}_3$, —OCHX$^{62}_2$, —OCH$_2$X$^6$, —CN, —N$_3$, —OH, —NH$_2$, —COO H, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^6$ is independently halogen. In embodiments, X$^6$ is independently —F or —Cl.

R$^{45}$ is independently oxo, halogen, —CX$^{45}_3$, —CHX$^{45}_2$, —CH$_2$X$^{45}$, —OCX$^{45}_3$, —OCHX$^{45}_2$, —OCH$_2$X$^{45}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl. In embodiments, R$^{45}$ is independently oxo, halogen, —CX$^{45}_3$, —CHX$^{45}_2$, —CH$_2$X$^{45}$, —OCX$^{45}_3$, —OCHX$^{45}_2$, —OCH$_2$X$^{45}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. X$^{45}$ is independently halogen. In embodiments, X$^{45}$ is independently —F or —Cl.

R$^{46}$ is independently oxo, halogen, —CX$^{46}_3$, —CHX$^{46}_2$, —CH$_2$X$^{46}$, —OCX$^{46}_3$, —OCHX$^{46}_2$, —OCH$_2$X$^{46}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl. In embodiments R$^{46}$ is independently oxo, halogen, —CX$^{46}_3$, —CHX$^{46}_2$, —CH$_2$X$^{46}$, —OCX$^{46}_3$, —OCHX$^{46}_2$, —OCH$_2$X$^{46}$, —CN, —N$_3$, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{46}$ is independently halogen. In embodiments, $X^{46}$ is independently —F or —Cl.

In embodiments, $L^2$ is a substituted or unsubstituted $(C_1-C_5)$ alkylene, or substituted or unsubstituted 2 to 5 membered heteroalkylene. In embodiments, $L^2$ is a bond. In embodiments, $L^2$ is substituted or unsubstituted $(C_1-C_5)$ alkylene. In embodiments, $L^2$ is substituted or unsubstituted 2 to 5 membered heteroalkylene.

In embodiments, $L^2$ is substituted or unsubstituted $(C_1-C_3)$ alkylene, or substituted or unsubstituted 2 to 5 membered heteroalkylene. In embodiments, $L^2$ is substituted or unsubstituted $(C_1-C_3)$ alkylene. In embodiments, $L^2$ is substituted or unsubstituted 2 to 3 membered heteroalkylene.

In embodiments, $L^2$ is a bond. In embodiments, $L^2$ is substituted or unsubstituted 2 to 5 membered heteroalkylene. In embodiments, $L^2$ is unsubstituted 2 to 5 membered heteroalkylene. In embodiments, $L^2$ is substituted or unsubstituted $(C_1-C_5)$ alkylene. In embodiments, $L^2$ is substituted or unsubstituted $(C_2-C_5)$ alkylene. In embodiments, $L^2$ is unsubstituted $(C_1-C_5)$ alkylene. In embodiments, $L^2$ is unsubstituted $(C_1-C_4)$ alkylene. In embodiments, $L^2$ is unsubstituted $(C_1-C_3)$ alkylene. In embodiments, $L^2$ is unsubstituted $(C_1-C_2)$ alkylene. In embodiments, $L^2$ is unsubstituted $C_2$ alkylene.

In embodiments, $L^2$ is a bond, substituted or unsubstituted $(C_1-C_5)$ alkylene, or substituted or unsubstituted 2 to 5 membered heteroalkylene. In embodiments, $L^2$ is a bond, substituted or unsubstituted $(C_2-C_5)$ alkylene, or substituted or unsubstituted 2 to 5 membered heteroalkylene.

In embodiments, $-L^3-L^2-$ has the formula:

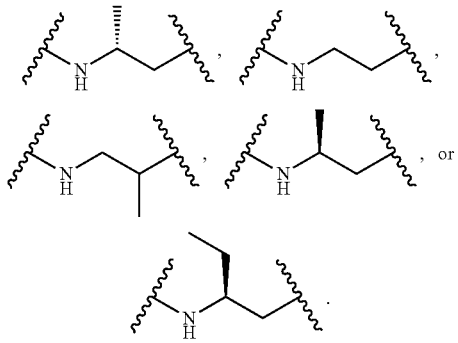

In embodiments, $-L^3-L^2-$ has the formula:

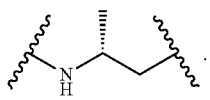

In embodiments, $-L^3-L^2-$ has the formula:

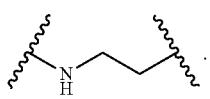

In embodiments, $-L^3-L^2-$ has the formula:

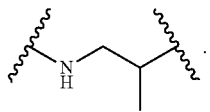 [SMILES: *NCC(*)C]

In embodiments, $-L^3-L^2-$ has the formula:

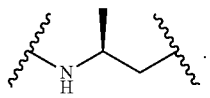 [SMILES: *C[C@H](C)N*]

In embodiments, $-L^3-L^2-$ has the formula:

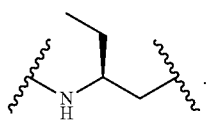 [SMILES: *C[C@H](CC)N*]

In embodiments, $L^2$ is a bond, $R^{99}$-substituted or unsubstituted alkylene, or $R^{99}$-substituted or unsubstituted heteroalkylene.

$R^{99}$ is independently oxo, halogen, —$CX^{99}_3$, —$CHX^{99}_2$, —$CH_2X^{99}$, —$OCHX^{99}_2$, —$OCX^{99}_3$, —$OCHX^{99}_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{100}$-substituted or unsubstituted alkyl, $R^{100}$-substituted or unsubstituted heteroalkyl, $R^{100}$-substituted or unsubstituted cycloalkyl, $R^{100}$-substituted or unsubstituted heterocycloalkyl, $R^{100}$-substituted or unsubstituted aryl, or $R^{100}$-substituted or unsubstituted heteroaryl. In embodiments, $R^{99}$ is independently oxo, halogen, —$CX^{99}_3$, —$CHX^{99}_2$, —$CH_2X^{99}$, —$OCHX^{99}_2$, —$OCX^{99}_3$, —$OCHX^{99}_2$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{99}$ is independently halogen. In embodiments, $X^{99}$ is independently —F or —Cl.

$R^{100}$ is independently oxo, halogen, —$CX^{100}_3$, —$CHX^{100}_2$, —$CH_2X^{100}$, —$OCX^{100}_3$, —$OCHX^{100}_2$, —$OCH_2X^{100}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{101}$-substituted or unsubstituted alkyl, $R^{101}$-substituted or unsubstituted heteroalkyl, $R^{101}$-substituted or unsubstituted cycloalkyl, $R^{101}$-substituted or unsubstituted heterocycloalkyl, $R^{101}$-substituted or unsubstituted aryl, or $R^{101}$-substituted or unsubstituted heteroaryl. In embodiments, $R^{100}$ is independently oxo, halogen, —$CX^{100}_3$, —$CHX^{100}_2$, —$CH_2X^{100}$, —$OCX^{100}_3$, —$OCHX^{100}_2$, —$OCH_2X^{100}$, —CN, —$N_3$, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl. $X^{100}$ is independently halogen. In embodiments, $X^{100}$ is independently —F or —Cl.

In embodiments, $L^3$ is —N($R^6$)—. In embodiments, $L^3$ is —N(CH$_3$)—. In embodiments, $L^3$ is a bond. In embodiments, $L^3$ is —CH($R^6$)—. In embodiments, $L^3$ is —O—. In embodiments, $L^3$ is —CH$_2$—. In embodiments, $L^3$ is —NH—. In embodiments, $L^3$ is —O— or —N($R^6$)—.

Ring A is a monocyclic cycloalkyl, monocyclic heterocycloalkyl, fused ring aryl, or fused ring heteroaryl. It is understood that when $R^3$ is hydrogen, Ring A is considered unsubstituted. It is understood that when $R^3$ is not hydrogen, Ring A is considered substituted (e.g., $R^3$-substituted).

In embodiments, Ring A is substituted or unsubstituted monocyclic cycloalkyl (e.g., $C_3$-$C_8$ cycloalkyl, $C_3$-$C_6$ cycloalkyl, or $C_5$-$C_6$ cycloalkyl). In embodiments, Ring A is substituted or unsubstituted $C_3$-$C_8$ monocyclic cycloalkyl. In embodiments, Ring A is substituted or unsubstituted $C_3$-$C_6$ monocyclic cycloalkyl. In embodiments, Ring A is substituted or unsubstituted $C_5$-$C_6$ monocyclic cycloalkyl. In embodiments, Ring A is substituted or unsubstituted $C_6$ monocyclic cycloalkyl. In embodiments, Ring A is substituted or unsubstituted $C_5$ monocyclic cycloalkyl.

In embodiments, Ring A is substituted or unsubstituted monocyclic heterocycloalkyl (e.g., 3 to 8 membered heterocycloalkyl, 3 to 6 membered heterocycloalkyl, or 5 to 6 membered heterocycloalkyl). In embodiments, Ring A is substituted monocyclic heterocycloalkyl (e.g., 3 to 8 membered heterocycloalkyl, 3 to 6 membered heterocycloalkyl, or 5 to 6 membered heterocycloalkyl). In embodiments, Ring A is an unsubstituted monocyclic heterocycloalkyl (e.g., 3 to 8 membered heterocycloalkyl, 3 to 6 membered heterocycloalkyl, or 5 to 6 membered heterocycloalkyl). In embodiments, Ring A is aziridinyl, oziranyl, thiiranyl, azetidinyl, 1,2-dihydroazotyl, oxetanyl, 2H-oxetyl, thietanyl, 2H-thietyl, pyrrolidinyl, 2,5-dihydro-1H-pyrrolyl, 4,5-dihydro-1H-imidazolyl, imidazolinyl, pyrazolinyl, tetrahydrofuranyl, thiolanyl, piperidinyl, piperazinyl, 2H-pyranyl, morpholinyl, 1,4-dioxanyl, tetrahydro-2H-pyranyl, thianyl, or dithianyl.

In embodiments, Ring A is indolyl, benzimidazolyl, indazolyl, benzotriazolyl, pyrrolopyrimidinyl, purinyl, indolizinyl, pyrrolopyriazinyl, pyrrolopyriminyl, imidazopyridazinyl, imidazopyridinyl, imidazopyrimidinyl, cinnolinyl, quinazolinyl, quinoxalinyl, phthalazinyl, pyridopyrazinyl, pteridinyl, pyrazolopyridinyl, quinolinyl, isoquinolinyl, naphthyridinyl, or carbazolyl. In embodiments, Ring A is benzoxazolyl or dibenzofuranyl. In embodiments, Ring A is benzothiophenyl or dibenzothiophenyl.

In embodiments, Ring A is naphthyl. In embodiments, Ring A has the formula:

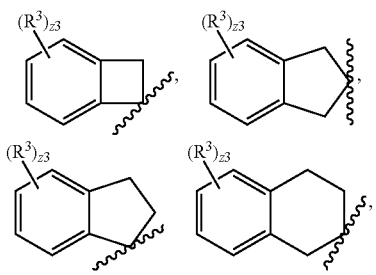

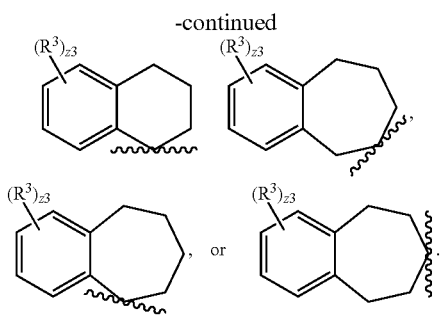

In embodiments, Ring B is independently substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, Ring B is substituted or unsubstituted ($C_3$-$C_{10}$) cycloalkyl, substituted or unsubstituted 3 to 10 membered heterocycloalkyl, substituted or unsubstituted ($C_6$-$C_{10}$) aryl, or substituted or unsubstituted 5 to 10 membered heteroaryl.

In embodiments, Ring B is $R^4$-substituted or unsubstituted ($C_3$-$C_{10}$) cycloalkyl, $R^4$-substituted or unsubstituted 5 to 10 membered heterocycloalkyl, $R^4$-substituted or unsubstituted ($C_6$-$C_{10}$) aryl, or $R^4$-substituted or unsubstituted 5 to 10 membered heteroaryl.

In embodiments, Ring B is $R^4$-substituted or unsubstituted thienyl, $R^4$-substituted or unsubstituted phenyl, $R^4$-substituted or unsubstituted benzothienyl, $R^4$-substituted or unsubstituted naphthyl, $R^4$-substituted or unsubstituted benzofuranyl, $R^4$-substituted or unsubstituted furanyl, $R^4$-substituted or unsubstituted pyrrolyl, or $R^4$-substituted or unsubstituted 2,3-dihydro-1H-indenyl. In embodiments, Ring B is unsubstituted thienyl. In embodiments, Ring B is unsubstituted phenyl. In embodiments, Ring B is unsubstituted benzothienyl. In embodiments, Ring B is para-methyl substituted phenyl. In embodiments, Ring B is unsubstituted naphthyl. In embodiments, Ring B is unsubstituted 2,3-dihydro-1H-indenyl.

In embodiments, Ring B is substituted or unsubstituted cycloalkyl. In embodiments, Ring B is substituted or unsubstituted heterocycloalkyl. In embodiments, Ring B is substituted or unsubstituted aryl. In embodiments, Ring B is substituted or unsubstituted heteroaryl. In embodiments, Ring B is substituted or unsubstituted ($C_3$-$C_{10}$) cycloalkyl, substituted or unsubstituted 3 to 10 membered heterocycloalkyl, substituted or unsubstituted ($C_6$-$C_{10}$) aryl, or substituted or unsubstituted 5 to 10 membered heteroaryl. In embodiments, Ring B is substituted or unsubstituted ($C_3$-$C_{10}$) cycloalkyl. In embodiments, Ring B is substituted or unsubstituted 3 to 10 membered heterocycloalkyl. In embodiments, Ring B is substituted or unsubstituted ($C_6$-$C_{10}$) aryl. In embodiments, Ring B is substituted or unsubstituted 5 to 10 membered heteroaryl. In embodiments, Ring B is substituted or unsubstituted ($C_3$-$C_6$) cycloalkyl. In embodiments, Ring B is substituted or unsubstituted 3 to 6 membered heterocycloalkyl. In embodiments, Ring B is substituted or unsubstituted phenyl. In embodiments, Ring B is substituted or unsubstituted naphthyl. In embodiments, Ring B is substituted or unsubstituted 5 to 9 membered heteroaryl. In embodiments, Ring B is substituted or unsubstituted 5 to 6 membered heteroaryl. In embodiments, Ring B is an unsubstituted 5 to 6 membered heteroaryl. In embodiments, Ring B is substituted or unsubstituted 5 membered heteroaryl. In embodiments, Ring B is a substituted 5 membered heteroaryl. In embodiments, Ring B is an unsubstituted 5 membered heteroaryl.

In embodiments, Ring B is $R^4$-substituted or unsubstituted ($C_3$-$C_{10}$) cycloalkyl, $R^4$-substituted or unsubstituted 5 to 10 membered heterocycloalkyl, $R^4$-substituted or unsubstituted ($C_6$-$C_{10}$) aryl, or $R^4$-substituted or unsubstituted 5 to 10 membered heteroaryl. In embodiments, Ring B is $R^4$-substituted or unsubstituted ($C_3$-$C_{10}$) cycloalkyl or $R^4$-substituted or unsubstituted 5 to 10 membered heterocycloalkyl. In embodiments, Ring B is $R^4$-substituted or unsubstituted ($C_3$-$C_{10}$) cycloalkyl. In embodiments, Ring B is $R^4$-substituted or unsubstituted 3 to 10 membered heterocycloalkyl. In embodiments, Ring B is $R^4$-substituted or unsubstituted ($C_6$-$C_{10}$) aryl. In embodiments, Ring B is $R^4$-substituted or unsubstituted 5 to 10 membered heteroaryl. In embodiments, Ring B is $R^4$-substituted or unsubstituted ($C_3$-$C_6$) cycloalkyl. In embodiments, Ring B is $R^4$-substituted or unsubstituted 3 to 6 membered heterocycloalkyl. In embodiments, Ring B is $R^4$-substituted or unsubstituted phenyl. In embodiments, Ring B is $R^4$-substituted or unsubstituted naphthyl. In embodiments, Ring B is $R^4$-substituted or unsubstituted 5 to 9 membered heteroaryl. In embodiments, Ring B is $R^4$-substituted or unsubstituted 5 to 6 membered heteroaryl. In embodiments, Ring B is $R^4$-substituted or unsubstituted thienyl. In embodiments, Ring B is $R^4$-substituted or unsubstituted phenyl. In embodiments, Ring B is $R^4$-substituted or unsubstituted benzothienyl. In embodiments, Ring B is $R^4$-substituted or unsubstituted naphthyl. In embodiments, Ring B is $R^4$-substituted or unsubstituted benzofuranyl. In embodiments, Ring B is $R^4$-substituted or unsubstituted furanyl. In embodiments, Ring B is $R^4$-substituted or unsubstituted pyrrolyl. In embodiments, Ring B is $R^4$-substituted or unsubstituted 2,3-dihydro-1H-indenyl.

In embodiments, Ring B is substituted cycloalkyl. In embodiments, Ring B is substituted heterocycloalkyl. In embodiments, Ring B is substituted aryl. In embodiments, Ring B is substituted heteroaryl. In embodiments, Ring B is substituted ($C_3$-$C_{10}$) cycloalkyl, substituted 3 to 10 membered heterocycloalkyl, substituted ($C_6$-$C_{10}$) aryl, or substituted 5 to 10 membered heteroaryl. In embodiments, Ring B is substituted ($C_3$-$C_{10}$) cycloalkyl. In embodiments, Ring B is substituted 3 to 10 membered heterocycloalkyl. In embodiments, Ring B is substituted ($C_6$-$C_{10}$) aryl. In embodiments, Ring B is substituted 5 to 10 membered heteroaryl. In embodiments, Ring B is substituted ($C_3$-$C_6$) cycloalkyl. In embodiments, Ring B is substituted 3 to 6 membered heterocycloalkyl. In embodiments, Ring B is substituted phenyl. In embodiments, Ring B is substituted naphthyl. In embodiments, Ring B is substituted 5 to 9 membered heteroaryl. In embodiments, Ring B is substituted 5 to 6 membered heteroaryl. In embodiments, Ring B is $R^4$-substituted ($C_3$-$C_{10}$) cycloalkyl, $R^4$-substituted 5 to 10 membered heterocycloalkyl, $R^4$-substituted ($C_6$-$C_{10}$) aryl, or $R^4$-substituted 5 to 10 membered heteroaryl. In embodiments, Ring B is $R^4$-substituted ($C_3$-$C_{10}$) cycloalkyl or $R^4$-substituted 5 to 10 membered heterocycloalkyl. In embodiments, Ring B is $R^4$-substituted ($C_3$-$C_{10}$) cycloalkyl. In embodiments, Ring B is $R^4$-substituted 3 to 10 membered heterocycloalkyl. In embodiments, Ring B is $R^4$-substituted ($C_6$-$C_{10}$) aryl. In embodiments, Ring B is $R^4$-substituted 5 to 10 membered heteroaryl. In embodiments, Ring B is $R^4$-substituted ($C_3$-$C_6$) cycloalkyl. In embodiments, Ring B is $R^4$-substituted 3 to 6 membered heterocycloalkyl. In embodiments, Ring B is $R^4$-substituted phenyl. In embodiments, Ring B is $R^4$-substituted naphthyl. In embodiments, Ring B is $R^4$-substituted 5 to 9 membered heteroaryl. In embodiments, Ring B is $R^4$-substituted 5 to 6 membered heteroaryl. In embodiments, Ring B is $R^4$-substituted thienyl. In embodiments, Ring B is $R^4$-substituted phenyl. In embodiments, Ring B is $R^4$-substituted benzothienyl. In embodiments, Ring B is $R^4$-substituted naphthyl. In embodiments, Ring B is $R^4$-substituted benzofuranyl. In embodiments, Ring B is $R^4$-substituted furanyl. In embodiments, Ring B is $R^4$-substituted pyrrolyl. In embodiments, Ring B is $R^4$-substituted 2,3-dihydro-1H-indenyl.

In embodiments, Ring B is unsubstituted cycloalkyl. In embodiments, Ring B is unsubstituted heterocycloalkyl. In embodiments, Ring B is unsubstituted aryl. In embodiments, Ring B is unsubstituted heteroaryl. In embodiments, Ring B is unsubstituted ($C_3$-$C_{10}$) cycloalkyl, unsubstituted 3 to 10 membered heterocycloalkyl, unsubstituted ($C_6$-$C_{10}$) aryl, or unsubstituted 5 to 10 membered heteroaryl. In embodiments, Ring B is unsubstituted ($C_3$-$C_{10}$) cycloalkyl. In embodiments, Ring B is unsubstituted 3 to 10 membered heterocycloalkyl. In embodiments, Ring B is unsubstituted ($C_6$-$C_{10}$) aryl. In embodiments, Ring B is unsubstituted 5 to 10 membered heteroaryl. In embodiments, Ring B is unsubstituted ($C_3$-$C_6$) cycloalkyl. In embodiments, Ring B is unsubstituted 3 to 6 membered heterocycloalkyl. In embodiments, Ring B is unsubstituted phenyl. In embodiments, Ring B is unsubstituted naphthyl. In embodiments, Ring B is unsubstituted 5 to 9 membered heteroaryl. In embodiments, Ring B is unsubstituted 5 to 6 membered heteroaryl. In embodiments, Ring B is unsubstituted ($C_3$-$C_{10}$) cycloalkyl, unsubstituted 5 to 10 membered heterocycloalkyl, unsubstituted ($C_6$-$C_{10}$) aryl, or unsubstituted 5 to 10 membered heteroaryl. In embodiments, Ring B is unsubstituted ($C_3$-$C_{10}$) cycloalkyl or unsubstituted 5 to 10 membered heterocycloalkyl. In embodiments, Ring B is unsubstituted ($C_3$-$C_{10}$) cycloalkyl. In embodiments, Ring B is unsubstituted 3 to 10 membered heterocycloalkyl. In embodiments, Ring B is unsubstituted ($C_6$-$C_{10}$) aryl. In embodiments, Ring B is unsubstituted 5 to 10 membered heteroaryl. In embodiments, Ring B is unsubstituted ($C_3$-$C_6$) cycloalkyl. In embodiments, Ring B is unsubstituted 3 to 6 membered heterocycloalkyl. In embodiments, Ring B is unsubstituted phenyl. In embodiments, Ring B is unsubstituted naphthyl. In embodiments, Ring B is unsubstituted 5 to 9 membered heteroaryl. In embodiments, Ring B is unsubstituted 5 to 6 membered heteroaryl. In embodiments, Ring B is unsubstituted thienyl. In embodiments, Ring B is unsubstituted phenyl. In embodiments, Ring B is unsubstituted benzothienyl. In embodiments, Ring B is unsubstituted naphthyl. In embodiments, Ring B is unsubstituted benzofuranyl. In embodiments, Ring B is unsubstituted furanyl. In embodiments, Ring B is unsubstituted pyrrolyl. In embodiments, Ring B is unsubstituted 2,3-dihydro-1H-indenyl. In embodiments, Ring B is unsubstituted phenyl. In embodiments, Ring B is In embodiments, Ring B is

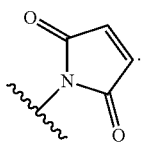 [SMILES: *N1C(=O)C=CC1=O]

In embodiments, Ring B is

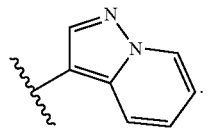 [SMILES: *c1cnn2ccccc12]

In embodiments, Ring B is

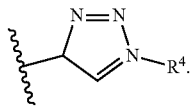

Ring B may be substituted with one $R^4$. Ring B may be substituted with two optionally different $R^4$ substituents. Ring B may be substituted with three optionally different $R^4$ substituents. Ring B may be substituted with four optionally different $R^4$ substituents. Ring B may be substituted with five optionally different $R^4$ substituents. Ring B may be substituted with six optionally different $R^4$ substituents. Ring B may be substituted with seven optionally different $R^4$ substituents. Ring B may be substituted with eight optionally different $R^4$ substituents. Ring B may be substituted with nine optionally different $R^4$ substituents. Ring B may be substituted with ten optionally different $R^4$ substituents.

In embodiments, Ring C is a substituted or unsubstituted $C_4$-$C_{10}$ cycloalkylene, substituted or unsubstituted 4 to 10 membered heterocycloalkylene, substituted or unsubstituted $C_6$-$C_{10}$ arylene, or substituted or unsubstituted 5 to 10 membered heteroarylene.

In embodiments, Ring C is substituted or unsubstituted ($C_6$-$C_{10}$) arylene or substituted or unsubstituted 5 to 10 membered heteroarylene. Ring C may be substituted or unsubstituted ($C_6$-$C_{10}$) arylene. Ring C may be substituted or unsubstituted phenylene. Ring C may be substituted or unsubstituted napthylene. Ring C may be substituted or unsubstituted 5 to 10 membered heteroarylene. Ring C may be substituted or unsubstituted 5 to 6 membered heteroarylene. Ring C may be substituted or unsubstituted thienylene. Ring C may be substituted or unsubstituted furanylene. Ring C may be substituted or unsubstituted pyrrolylene. Ring C may be substituted or unsubstituted imidazolylene. Ring C may be substituted or unsubstituted pyrazolylene. Ring C may be substituted or unsubstituted oxazolylene. Ring C may be substituted or unsubstituted isoxazolylene. Ring C may be substituted or unsubstituted thaizolylene. Ring C may be substituted or unsubstituted pyridinylene. Ring C may be substituted or unsubstituted pyridylene. Ring C may be substituted or unsubstituted pyrazinylene. Ring C may be substituted or unsubstituted pyrimidinylene. Ring C may be substituted or unsubstituted pyridazinylene. Ring C may be substituted or unsubstituted 1,2,3-triazinylene. Ring C may be substituted or unsubstituted 1,2,4-triazinylene. Ring C may be substituted or unsubstituted 1,3,5-triazinylene. In embodiments, Ring C is substituted ($C_6$-$C_{10}$) arylene or substituted 5 to 10 membered heteroarylene. Ring C may be substituted ($C_6$-$C_{10}$) arylene. Ring C may be substituted phenylene. Ring C may be substituted napthylene. Ring C may be substituted 5 to 10 membered heteroarylene. Ring C may be substituted 5 to 6 membered heteroarylene. Ring C may be substituted thienylene. Ring C may be substituted furanylene. Ring C may be substituted pyrrolylene. Ring C may be substituted imidazolylene. Ring C may be substituted pyrazolylene. Ring C may be substituted oxazolylene. Ring C may be substituted isoxazolylene. Ring C may be substituted thaizolylene. Ring C may be substituted pyridinylene. Ring C may be substituted pyridylene. Ring C may be substituted pyrazinylene. Ring C may be substituted pyrimidinylene. Ring C may be substituted pyridazinylene. Ring C may be substituted 1,2,3-triazinylene. Ring C may be substituted 1,2,4-triazinylene. Ring C may be substituted 1,3,5-triazinylene. In embodiments, Ring C is unsubstituted ($C_6$-$C_{10}$) arylene or unsubstituted 5 to 10 membered heteroarylene. Ring C may be unsubstituted ($C_6$-$C_{10}$) arylene. Ring C may be unsubstituted phenylene. Ring C may be unsubstituted napthylene. Ring C may be unsubstituted 5 to 10 membered heteroarylene. Ring C may be unsubstituted 5 to 6 membered heteroarylene.

Ring C may be unsubstituted thienylene. Ring C may be unsubstituted furanylene. Ring C may be unsubstituted pyrrolylene. Ring C may be unsubstituted imidazolylene. Ring C may be unsubstituted pyrazolylene. Ring C may be unsubstituted oxazolylene. Ring C may be unsubstituted isoxazolylene. Ring C may be unsubstituted thaizolylene. Ring C may be unsubstituted pyridinylene. Ring C may be unsubstituted pyridylene. Ring C may be unsubstituted pyrazinylene. Ring C may be unsubstituted pyrimidinylene. Ring C may be unsubstituted pyridazinylene. Ring C may be unsubstituted 1,2,3-triazinylene. Ring C may be unsubstituted 1,2,4-triazinylene. Ring C may be unsubstituted 1,3,5-triazinylene.

In embodiments, Ring C is substituted (e.g., substituted with substituent group(s), size-limited substituent group(s), or lower substituent group(s)) or unsubstituted ($C_6$-$C_{10}$) arylene or substituted (e.g., substituted with substituent group(s), size-limited substituent group(s), or lower substituent group(s)) or unsubstituted 5 to 10 membered heteroarylene. Ring C may be substituted (e.g., substituted with substituent group(s), size-limited substituent group(s), or lower substituent group(s)) or unsubstituted ($C_6$-$C_{10}$) arylene. Ring C may be substituted (e.g., substituted with substituent group(s), size-limited substituent group(s), or lower substituent group(s)) or unsubstituted phenylene. Ring C may be substituted (e.g., substituted with substituent group(s), size-limited substituent group(s), or lower substituent group(s)) or unsubstituted napthylene. Ring C may be substituted (e.g., substituted with substituent group(s), size-limited substituent group(s), or lower substituent group(s)) or unsubstituted 5 to 10 membered heteroarylene. Ring C may be substituted (e.g., substituted with substituent group(s), size-limited substituent group(s), or lower substituent group(s)) or unsubstituted 5 to 6 membered heteroarylene. Ring C may be substituted (e.g., substituted with substituent group(s), size-limited substituent group(s), or lower substituent group(s)) or unsubstituted thienylene. Ring C may be substituted (e.g., substituted with substituent group(s), size-limited substituent group(s), or lower substituent group(s)) or unsubstituted furanylene. Ring C may be substituted (e.g., substituted with substituent group(s), size-limited substituent group(s), or lower substituent group(s)) or unsubstituted pyrrolylene. Ring C may be substituted (e.g., substituted with substituent group(s), size-limited substituent group(s), or lower substituent group(s)) or unsubstituted imidazolylene. Ring C may be substituted (e.g., substituted with substituent group(s), size-limited substituent group(s), or lower substituent group(s)) or unsubstituted pyrazolylene. Ring C may be substituted (e.g., substituted with substituent group(s), size-limited substituent group(s), or lower substituent group(s)) or unsubstituted oxazolylene. Ring C may be substituted (e.g., substituted with substituent group(s), size-limited substituent group(s), or lower substituent group(s)) or unsubstituted isoxazolylene. Ring C may be substituted (e.g., substituted with substituent group(s), size-limited substituent group(s), or lower substituent group(s)) or unsubstituted thaizolylene. Ring C may be substituted (e.g., substituted with substituent group(s), size-limited substituent group(s), or lower substituent group(s)) or unsubstituted pyridinylene. Ring C may be substituted (e.g., substituted with substituent group(s), size-limited substituent group(s), or lower substituent group(s)) or unsubstituted pyridylene. Ring C may be substituted (e.g., substituted with substituent group(s), size-limited substituent group(s), or lower substituent group(s)) or unsubstituted pyrazinylene. Ring C may be substituted (e.g., substituted with substituent group(s), size-limited substituent group(s), or lower substituent group(s)) or unsubstituted pyrimidinylene. Ring C may be substituted (e.g., substituted with substituent group(s), size-limited substituent group(s), or lower substituent group(s)) or unsubstituted pyridazinylene. Ring C may be substituted (e.g., substituted with substituent group(s), size-limited substituent group(s), or lower substituent group(s)) or unsubstituted 1,2,3-triazinylene. Ring C may be substituted (e.g., substituted with substituent group(s), size-limited substituent group(s), or lower substituent group(s)) or unsubstituted 1,2,4-triazinylene. Ring C may be substituted (e.g., substituted with substituent group(s), size-limited substituent group(s), or lower substituent group(s)) or unsubstituted 1,3,5-triazinylene. In embodiments, Ring C is substituted (e.g., substituted with substituent group(s), size-limited substituent group(s), or lower substituent group(s)) ($C_6$-$C_{10}$) arylene or substituted (e.g., substituted with substituent group(s), size-limited substituent group(s), or lower substituent group(s)) 5 to 10 membered heteroarylene. Ring C may be substituted (e.g., substituted with substituent group(s), size-limited substituent group(s), or lower substituent group(s)) ($C_6$-$C_{10}$) arylene. Ring C may be substituted (e.g., substituted with substituent group(s), size-limited substituent group(s), or lower substituent group(s)) phenylene. Ring C may be substituted (e.g., substituted with substituent group(s), size-limited substituent group(s), or lower substituent group(s)) napthylene. Ring C may be substituted (e.g., substituted with substituent group(s), size-limited substituent group(s), or lower substituent group(s)) 5 to 10 membered heteroarylene. Ring C may be substituted (e.g., substituted with substituent group(s), size-limited substituent group(s), or lower substituent group(s)) 5 to 6 membered heteroarylene. Ring C may be substituted (e.g., substituted with substituent group(s), size-limited substituent group(s), or lower substituent group(s)) thienylene. Ring C may be substituted (e.g., substituted with substituent group(s), size-limited substituent group(s), or lower substituent group(s)) furanylene. Ring C may be substituted (e.g., substituted with substituent group(s), size-limited substituent group(s), or lower substituent group(s)) pyrrolylene. Ring C may be substituted (e.g., substituted with substituent group(s), size-limited substituent group(s), or lower substituent group(s)) imidazolylene. Ring C may be substituted (e.g., substituted with substituent group(s), size-limited substituent group(s), or lower substituent group(s)) pyrazolylene. Ring C may be substituted (e.g., substituted with substituent group(s), size-limited substituent group(s), or lower substituent group(s)) oxazolylene. Ring C may be substituted (e.g., substituted with substituent group(s), size-limited substituent group(s), or lower substituent group(s)) isoxazolylene. Ring C may be substituted (e.g., substituted with substituent group(s), size-limited substituent group(s), or lower substituent group(s)) thaizolylene. Ring C may be substituted (e.g., substituted with substituent group(s), size-limited substituent group(s), or lower substituent group(s)) pyridinylene. Ring C may be substituted (e.g., substituted with substituent group(s), size-limited substituent group(s), or lower substituent group(s)) pyridylene. Ring C may be substituted (e.g., substituted with substituent group(s), size-limited substituent group(s), or lower substituent group(s)) pyrazinylene. Ring C may be substituted (e.g., substituted with substituent group(s), size-limited substituent group(s), or lower substituent group(s)) pyrimidinylene. Ring C may be substituted (e.g., substituted with substituent group(s), size-limited substituent group(s), or lower substituent group(s)) pyridazinylene. Ring C may be substituted (e.g., substituted with substituent group(s), size-limited substituent group(s), or lower substituent group(s)) 1,2,3-triazinylene. Ring C may be substituted (e.g., substituted with substituent group(s), size-limited substituent group(s), or lower substituent group(s)) 1,2,4-triazinylene. Ring C may be substituted (e.g., substituted with substituent group(s), size-limited substituent group(s), or lower substituent group(s)) 1,3,5-triazinylene. In embodiments, Ring C is substituted with oxo. Ring C may be oxo substituted pyrimidinylene. In embodiments, Ring C is substituted with oxo. Ring C may be oxo substituted 1,4-dihydropyrimidinylene. Ring C may be oxo substituted cyclobutenylene.

In embodiments, Ring C has the formula:

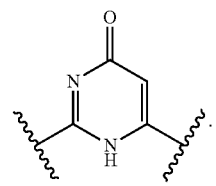 [SMILES: *c1cc(=O)nc(*)[nH]1]

In embodiments, Ring C has the formula:

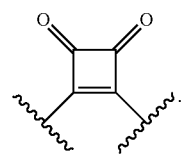 [SMILES: *c1c(*)c(=O)c1=O]

In embodiments, Ring C is a substituted or unsubstituted $C_4$-$C_{10}$ cycloalkylene. In embodiments, Ring C is a substituted or unsubstituted 4 to 10-membered heterocycloalkylene. In embodiments, Ring C is a substituted or unsubstituted $C_6$-$C_{10}$ arylene. In embodiments, Ring C is a substituted or unsubstituted 5 to 10-membered heteroarylene. In embodiments, Ring C is a substituted or unsubstituted $C_4$-$C_{10}$ cycloalkenylene. In embodiments, Ring C is a substituted or unsubstituted $C_4$ cycloalkenylene. In embodiments, Ring C is an oxo substituted $C_4$ cycloalkenylene. In embodiments, Ring C is a substituted or unsubstituted 5 to 6 membered heteroarylene. In embodiments, Ring C is a substituted pyrimidinylene. Ring C may be substituted pyrimidinylene.

Ring C may be substituted with one substituent group, size-limited substituent group, or lower substituent group. Ring C may be substituted with two optionally different groups selected from substituent groups, size-limited substituent groups, and lower substituent groups. Ring C may be substituted with three optionally different groups selected from substituent groups, size-limited substituent groups, or lower substituent groups. Ring C may be substituted with four optionally different groups selected from substituent groups, size-limited substituent groups, and lower substituent groups. Ring C may be substituted with five optionally different groups selected from substituent groups, size-limited substituent groups, and lower substituent groups. Ring C may be substituted with six optionally different groups selected from substituent groups, size-limited substituent groups, and lower substituent groups. Ring C may be substituted with seven optionally different groups selected from substituent groups, size-limited substituent groups, and lower substituent groups. Ring C may be substituted with eight optionally different groups selected from substituent groups, size-limited substituent groups, and lower substituent groups. Ring C may be substituted with nine optionally different groups selected from substituent groups, size-limited substituent groups, and lower substituent groups. Ring C may be substituted with ten optionally different groups selected from substituent groups, size-limited substituent groups, and lower substituent groups.

$R^{32}$, $R^{35}$, $R^{38}$, $R^{41}$, $R^{44}$, $R^{47}$, $R^{50}$, $R^{53}$, $R^{56}$, $R^{59}$, $R^{62}$, $R^{65}$, $R^{68}$, $R^{71}$, and $R^{101}$ are independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{31}$, $R^{34}$, $R^{37}$, $R^{40}$, $R^{43}$, $R^{46}$, $R^{49}$, $R^{52}$, $R^{55}$, $R^{58}$, $R^{61}$, $R^{64}$, $R^{67}$, $R^{70}$ and $R^{100}$ are independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

The symbol n is independently an integer from 0 to 2. X is independently —Cl, —Br, —I, or —F. In embodiments, X is —Cl. In embodiments, X is —Br. In embodiments, X is —I. In embodiments, X is —F. In embodiments, $X^a$ is —Cl. In embodiments, $X^a$ is —Br. In embodiments, $X^a$ is —I. In embodiments, $X^a$ is —F.

Each n1 may independently be 0. Each n1 may independently be 1. Each n1 may independently be 2. Each n1 may independently be 3. Each n1 may independently be 4. Each n may independently be 0. Each n may independently be 1. Each n may independently be 2. Each n may independently be 3. Each n may independently be 4. Each v1 may independently be 0. Each v1 may independently be 1. Each v1 may independently be 2. Each v1 may independently be 3. Each v1 may independently be 4. Each v may independently be 0. Each v may independently be 1. Each v may independently be 2. Each v may independently be 3. Each v2 may independently be 4. Each m1 may independently be 1. Each m1 may independently be 2. Each m may independently be 1. Each m may independently be 2.

In embodiments, z3 is 1. In embodiments, z3 is 2. In embodiments, z3 is 3. In embodiments, z3 is 4. In embodiments, z3 is 5. In embodiments, z3 is 6. In embodiments, z3 is 7. In embodiments, z3 is 8. In embodiments, z3 is 9. In embodiments, z3 is 10. In embodiments, z3 is an integer from 1 to 5. In embodiments, z3 is an integer from 1 to 2.

The symbol z4 is an integer from 0 to 10. In embodiments, z4 is 0. When z4 is 0, it is understood Ring B is unsubstituted (e.g., an unsubstituted aryl). In embodiments, z4 is 1. In embodiments, z4 is 2. In embodiments, z4 is 3. In embodiments, z4 is 4. In embodiments, z4 is 5. In embodiments, z4 is 6. In embodiments, z4 is 7. In embodiments, z4 is 8. In embodiments, z4 is 9. In embodiments, z4 is 10.

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer.

In embodiments, the compound described herein is capable of crossing the blood brain barrier. In embodiments, the compound described herein is a partial agonist of the OR. In embodiments, the compound described herein is a partial agonist of the OR. In embodiments, the compound described herein is a partial antagonist of the OR. Partial agonism is a common term of art, as described in Calvey et. al (Principles and Practice of Pharmacology for Anaesthetists p. 62 (2009)).

In some embodiments, the compound is any one of the compounds described herein (e.g., in an aspect, embodiment, claim, figure, table, or example).

In some embodiments, a compound as described herein may include multiple instances of $R^7$, $R^8$, $R^9$, $R^{10}$, $R^{11}$, $R^{12}$, $R^{13}$, $R^{14}$, $X^a$, $X$, m1, n1, v1, m, n, v, $R^3$, $R^4$, and/or other variables. In such embodiments, each variable may optional be different and be appropriately labeled to distinguish each group for greater clarity. For example, where each $R^7$, $R^8$, $R^9$, $R^{10}$, $R^{11}$, $R^{12}$, $R^{13}$, $R^{14}$, $X^a$, $X$, m1, n1, v, m, n, v, $R^3$, and/or $R^4$, is different, they may be referred to, for example, as $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$, $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$, $R^{10.1}$, $R^{10.2}$, $R^{10.3}$, $R^{10.4}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$, $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$, $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$, $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$, $X^{a1}$, $X^{a2}$, $X^{a3}$, $X^{a4}$, $X^{a5}$, $X^{a6}$, $X^{a7}$, $X^{a8}$, $X^{a9}$, $X^{a10}$, $X^{a11}$, $X^{a12}$, $X^{a13}$, $X^{a14}$, $X^{a15}$, $X^{a16}$, $X^{a17}$, $X^{a18}$, $X^{a19}$, $X^{a20}$, $X^{a21}$, $X^{a22}$, $X^{a23}$, $X^{a24}$, $X^{a25}$, $X^{a26}$, $X^{a27}$, $X^{a28}$, $X^{a29}$, $X^{a30}$, $X^{a31}$, $X^{a32}$, $X^{a33}$, $X^{a34}$, $X^{a35}$, $X^{a36}$, $X^{a37}$, $X^{a38}$, $X^{a39}$, $X^{a40}$, $X^{a41}$, $X^{a42}$, $X\text{---}^1$, $X\text{---}^2$, $X\text{---}^3$, $X\text{---}^4$, $X\text{---}^5$, $X\text{---}^6$, $X\text{---}^7$, $X\text{---}^8$, $X\text{---}^9$, $X\text{---}^{10}$, $X\text{---}^{11}$, $X\text{---}^{12}$, $X\text{---}^{13}$, $X\text{---}^{14}$, $X\text{---}^{15}$, $X\text{---}^{16}$, $X\text{---}^{17}$, $X\text{---}^{18}$, $X\text{---}^{19}$, $X\text{---}^{20}$, $X\text{---}^{21}$, $X\text{---}^{22}$, $X\text{---}^{23}$, $X\text{---}^{24}$, $X\text{---}^{25}$, $X\text{---}^{26}$, $X\text{---}^{27}$, $X\text{---}^{28}$, $X\text{---}^{29}$, $X\text{---}^{30}$, $X\text{---}^{31}$, $X\text{---}^{32}$, $X\text{---}^{33}$, $X\text{---}^{34}$, $X\text{---}^{35}$, $X\text{---}^{36}$, $X\text{---}^{37}$, $X\text{---}^{38}$, $X\text{---}^{39}$, $X\text{---}^{40}$, $X\text{---}^{41}$, $X\text{---}^{42}$, $m1^1$, $m1^2$, $m1^3$, $m1^4$, $m1^5$, $n1^1$, $n1^2$, $n1^3$, $n1^4$, $n1^5$, $n^1$, $n^2$, $n^3$, $n^4$, $n^5$, $v^1$, $v1^2$, $v1^3$, $v1^4$, $v1^5$, $v^1$, $v^2$, $v^3$, $v^4$, $v^5$, $R^{3.1}$, $R^{3.2}$, $R^{3.3}$, $R^{3.4}$, $R^{3.5}$, $R^{3.6}$, $R^{3.7}$, $R^{3.8}$, $R^{3.9}$, $R^{3.10}$, $R^{3.11}$, $R^{3.12}$, $R^{3.13}$, $R^{3.14}$, $R^{3.15}$, $R^{3.16}$, $R^{3.17}$, $R^{3.18}$, $R^{3.19}$, $R^{3.20}$, $R^{3.21}$, $R^{3.22}$, $R^{3.23}$, $R^{3.24}$, $R^{3.25}$, $R^{3.26}$, $R^{3.27}$, $R^{3.28}$, $R^{3.29}$, $R^{3.30}$, $R^{3.31}$, $R^{3.32}$, $R^{3.33}$, $R^{3.34}$, $R^{3.35}$, $R^{3.36}$, $R^{3.37}$, $R^{3.38}$, $R^{3.39}$, $R^{3.40}$, $R^{3.41}$, $R^{3.42}$, $R^{4.1}$, $R^{4.2}$, $R^{4.3}$, $R^{4.4}$, $R^{4.5}$, $R^{4.6}$, $R^{4.7}$, $R^{4.8}$, $R^{4.9}$, $R^{4.10}$, $R^{4.11}$, $R^{4.12}$, $R^{4.13}$, $R^{4.14}$, $R^{4.15}$, $R^{4.16}$, $R^{4.17}$, $R^{4.18}$, $R^{4.19}$, $R^{4.20}$, $R^{4.21}$, $R^{4.22}$, $R^{4.23}$, $R^{4.24}$, $R^{4.25}$, $R^{4.26}$, $R^{4.27}$, $R^{4.28}$, $R^{4.29}$, $R^{4.30}$, $R^{4.31}$, $R^{4.32}$, $R^{4.33}$, $R^{4.34}$, $R^{4.35}$, $R^{4.36}$, $R^{4.37}$, $R^{4.38}$, $R^{4.39}$, $R^{4.40}$, $R^{4.41}$, $R^{4.42}$, respectively, wherein the definition of $R^7$ is assumed by $R^{7.1}$, $R^{7.2}$, $R^{7.3}$, $R^{7.4}$, $R^{7.5}$, $R^{7.6}$, $R^{7.7}$, $R^{7.8}$, $R^{7.9}$, $R^{7.10}$, $R^{7.11}$, $R^{7.12}$, $R^{7.13}$, $R^{7.14}$, $R^{7.15}$, $R^{7.16}$, $R^{7.17}$, $R^{7.18}$, $R^{7.19}$, $R^{7.20}$, $R^{7.21}$, $R^{7.22}$, $R^{7.23}$, $R^{7.24}$, $R^{7.25}$, $R^{7.26}$, $R^{7.27}$, $R^{7.28}$, $R^{7.29}$, $R^{7.30}$, $R^{7.31}$, $R^{7.32}$, $R^{7.33}$, $R^{7.34}$, $R^{7.35}$, $R^{7.36}$, $R^{7.37}$, $R^{7.38}$, $R^{7.39}$, $R^{7.40}$, $R^{7.41}$, $R^{7.42}$; $R^8$ is assumed by $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$; $R^9$ is assumed by $R^{9.1}$, $R^{9.2}$, $R^{9.3}$, $R^{9.4}$, $R^{9.5}$, $R^{9.6}$, $R^{9.7}$, $R^{9.8}$, $R^{9.9}$, $R^{9.10}$, $R^{9.11}$, $R^{9.12}$, $R^{9.13}$, $R^{9.14}$, $R^{9.15}$, $R^{9.16}$, $R^{9.17}$, $R^{9.18}$, $R^{9.19}$, $R^{9.20}$, $R^{9.21}$, $R^{9.22}$, $R^{9.23}$, $R^{9.24}$, $R^{9.25}$, $R^{9.26}$, $R^{9.27}$, $R^{9.28}$, $R^{9.29}$, $R^{9.30}$, $R^{9.31}$, $R^{9.32}$, $R^{9.33}$, $R^{9.34}$, $R^{9.35}$, $R^{9.36}$, $R^{9.37}$, $R^{9.38}$, $R^{9.39}$, $R^{9.40}$, $R^{9.41}$, $R^{9.42}$; $R^{10}$ is assumed by $R^{10.1}$, $R^{10.2}$, $R^{10.3}$, $R^{10.4}$, $R^{10.5}$, $R^{10.6}$, $R^{10.7}$, $R^{10.8}$, $R^{10.9}$, $R^{10.10}$, $R^{10.11}$, $R^{10.12}$, $R^{10.13}$, $R^{10.14}$, $R^{10.15}$, $R^{10.16}$, $R^{10.17}$, $R^{10.18}$, $R^{10.19}$, $R^{10.20}$, $R^{10.21}$, $R^{10.22}$, $R^{10.23}$, $R^{10.24}$, $R^{10.25}$, $R^{10.26}$, $R^{10.27}$, $R^{10.28}$, $R^{10.29}$, $R^{10.30}$, $R^{10.31}$, $R^{10.32}$, $R^{10.33}$, $R^{10.34}$, $R^{10.35}$, $R^{10.36}$, $R^{10.37}$, $R^{10.38}$, $R^{10.39}$, $R^{10.40}$, $R^{10.41}$, $R^{10.42}$; $R^{11}$ is assumed by $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$; $R^{12}$ is assumed by $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$; $R^{13}$ is assumed by $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$; $R^{14}$ is assumed by $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$; $X^a$ is assumed by $X^{a1}$, $X^{a2}$, $X^{a3}$, $X^{a4}$, $X^{a5}$, $X^{a6}$, $X^{a7}$, $X^{a8}$, $X^{a9}$, $X^{a10}$, $X^{a11}$, $X^{a12}$, $X^{a13}$, $X^{a14}$, $X^{a15}$, $X^{a16}$, $X^{a17}$, $X^{a18}$, $X^{a19}$, $X^{a20}$, $X^{a21}$, $X^{a22}$, $X^{a23}$, $X^{a24}$, $X^{a25}$, $X^{a26}$, $X^{a27}$, $X^{a28}$, $X^{a29}$, $X^{a30}$, $X^{a31}$, $X^{a32}$, $X^{a33}$, $X^{a34}$, $X^{a35}$, $X^{a36}$, $X^{a37}$, $X^{a38}$, $X^{a39}$, $X^{a40}$, $X^{a41}$, $X^{a42}$; $X$ is assumed by $X\text{---}^1$, $X\text{---}^2$, $X\text{---}^3$, $X\text{---}^4$, $X\text{---}^5$, $X\text{---}^6$, $X\text{---}^7$, $X\text{---}^8$, $X\text{---}^9$, $X\text{---}^{10}$, $X\text{---}^{11}$, $X\text{---}^{12}$, $X\text{---}^{13}$, $X\text{---}^{14}$, $X\text{---}^{15}$, $X\text{---}^{16}$, $X\text{---}^{17}$, $X\text{---}^{18}$, $X\text{---}^{19}$, $X\text{---}^{20}$, $X\text{---}^{21}$, $X\text{---}^2_{2}$, $X\text{---}^2_{3}$, $X\text{---}^{24}$, $X\text{---}^{25}$, $X\text{---}^{26}$, $X\text{---}^{27}$, $X\text{---}^{28}$, $X\text{---}^{29}$, $X\text{---}^{30}$, $X\text{---}^{31}$, $X\text{---}^3_{2}$, $X\text{---}^3_{3}$, $X\text{---}^{34}$, $X\text{---}^{35}$, $X\text{---}^{36}$, $X\text{---}^{37}$, $X\text{---}^{38}$, $X\text{---}^{39}$, $X\text{---}^{40}$, $X\text{---}^{41}$, $X\text{---}^{42}$; m1 is assumed by $m1^1$, $m1^2$, $m1^3$, $m1^4$, $m1^5$; n1 is assumed by $n1^1$, $n1^2$, $n1^3$, $n1^4$, $n1^5$; v1 is assumed by $v1^1$, $v1^2$, $v1^3$, $v1^4$, $v1^5$; m is assumed by $m^1$, $m^2$, $m^3$, $m^4$, m5; n is assumed by $n^1$, $n^2$, $n^3$, $n^4$, $n^5$; v is assumed by $v^1$, $v^2$, $v^3$, $v^4$, $v^5$; $R^3$ is assumed by $R^{3.1}$, $R^{3.2}$, $R^{3.3}$, $R^{3.4}$, $R^{3.5}$, $R^{3.6}$, $R^{3.7}$, $R^{3.8}$, $R^{3.9}$, $R^{3.10}$, $R^{3.11}$, $R^{3.12}$, $R^{3.13}$, $R^{3.14}$, $R^{3.15}$, $R^{3.16}$, $R^{3.17}$, $R^{3.18}$, $R^{3.19}$, $R^{3.20}$, $R^{3.21}$, $R^{3.22}$, $R^{3.23}$, $R^{3.24}$, $R^{3.25}$, $R^{3.26}$, $R^{3.27}$, $R^{3.28}$, $R^{3.29}$, $R^{3.30}$, $R^{3.31}$, $R^{3.32}$, $R^{3.33}$, $R^{3.34}$, $R^{3.35}$, $R^{3.36}$, $R^{3.37}$, $R^{3.38}$, $R^{3.39}$, $R^{3.40}$, $R^{3.41}$, $R^{3.42}$; and/or $R^4$ is assumed by $R^{4.1}$, $R^{4.2}$, $R^{4.3}$, $R^{4.4}$, $R^{4.5}$, $R^{4.6}$, $R^{4.7}$, $R^{4.8}$, $R^{4.9}$, $R^{4.10}$, $R^{4.11}$, $R^{4.12}$, $R^{4.13}$, $R^{4.14}$, $R^{4.15}$, $R^{4.16}$, $R^{4.17}$, $R^{4.18}$, $R^{4.19}$, $R^{4.20}$, $R^{4.21}$, $R^{4.22}$, $R^{4.23}$, $R^{4.24}$, $R^{4.25}$, $R^{4.26}$, $R^{4.27}$, $R^{4.28}$, $R^{4.29}$, $R^{4.30}$, $R^{4.31}$, $R^{4.32}$, $R^{4.33}$, $R^{4.34}$, $R^{4.35}$, $R^{4.36}$, $R^{4.37}$, $R^{4.38}$, $R^{4.39}$, $R^{4.40}$, $R^{4.41}$, $R^{4.42}$ The variables used within a definition of $R^7$, $R^8$, $R^9$, $R^{10}$, $R^{11}$, $R^{12}$, $R^{13}$, $R^{14}$, $X^a$, $X$, m1, n1, v1, m, n, v, $R^3$, $R^4$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

In embodiments, the compound comprises a higher binding affinity for the mu opioid receptor than for the kappa opioid receptor. In embodiments, the compound comprises a greater than 10-fold higher binding affinity for the mu opioid receptor than for the kappa opioid receptor. In embodiments, the compound comprises a greater than 100-fold higher binding affinity for the mu opioid receptor than for the kappa opioid receptor. In embodiments, the compound comprises a higher binding affinity for the mu opioid receptor than for the delta opioid receptor. In embodiments, the compound comprises a greater than 10-fold higher binding affinity for the mu opioid receptor than for the delta opioid receptor. In embodiments, the compound comprises a greater than 100-fold higher binding affinity for the mu opioid receptor than for the delta opioid receptor. In embodiments, the compound comprises a higher binding affinity for the mu opioid receptor than for the nociceptin receptor. In embodiments, the compound comprises a greater than 10-fold higher binding affinity for the mu opioid receptor than for the nociceptin receptor. In embodiments, the compound comprises a greater than 100-fold higher binding affinity for the mu opioid receptor than for the nociceptin receptor.

In embodiments, the compound comprises a greater than 10-fold, 20-fold, 30-fold, 40-fold, 50-fold, 100-fold, 500-fold, or 1000-fold higher binding affinity for the mu opioid receptor than for the kappa opioid receptor. In embodiments, the compound comprises a greater than 10-fold, 20-fold, 30-fold, 40-fold, 50-fold, 100-fold, 500-fold, or 1000-fold higher binding affinity for the mu opioid receptor than for the delta opioid receptor. In embodiments, the compound comprises a greater than 10-fold, 20-fold, 30-fold, 40-fold, 50-fold, 100-fold, 500-fold, or 1000-fold higher binding affinity for the mu opioid receptor than for the nociceptin receptor.

In embodiments, the compound comprises a lower addiction potential than medically used opioids. In embodiments, the compound comprises a lower addiction potential than medically used opiates. In embodiments, the compound comprises a lower addiction potential than morphine. In embodiments, the compound comprises a lower addiction potential than fentanyl. In embodiments, the compound comprises a lower addiction potential than heroin. In embodiments, the compound comprises a lower addiction potential than hydrocodone. In embodiments, the compound comprises a lower addiction potential than oxycodone. In embodiments, the compound comprises a lower addiction potential than morphine derivatives. In embodiments, the compound comprises a lower addiction potential than medically used morphine derivatives. In embodiments, the compound comprises a lower addiction potential than codeine. In embodiments, the compound comprises a lower addiction potential than methadone. In embodiments, the compound comprises a lower addiction potential than hydromorphone. In embodiments, the lowered addiction potential of the compound compared to the opioid is 10-fold. In embodiments, the lowered addiction potential of the compound compared to the opioid is 100-fold. In embodiments, the lowered addiction potential of the compound compared to the opioid is for an identical amount of the compound and the opioid. In embodiments, the lowered addiction potential of the compound compared to the opioid is for an identical level of pain relief.

In embodiments, the compound has the formula:

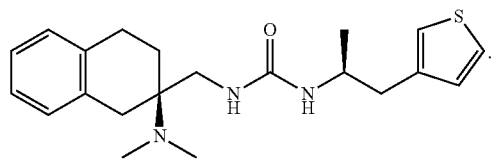 [SMILES: C[C@@H](Cc1ccsc1)NC(=O)NC[C@@]1(N(C)C)CCc2ccccc2C1]

In embodiments, the compound has the formula:

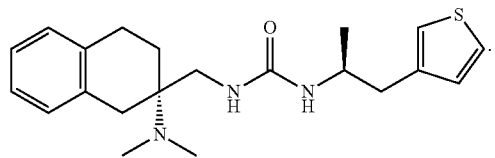 [SMILES: C[C@@H](Cc1ccsc1)NC(=O)NC[C@]1(N(C)C)CCc2ccccc2C1]

In embodiments, the compound has the formula:

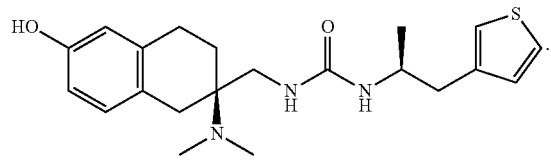 [SMILES: C[C@@H](Cc1ccsc1)NC(=O)NC[C@@]1(N(C)C)CCc2cc(O)ccc2C1]

In embodiments, the compound has the formula:

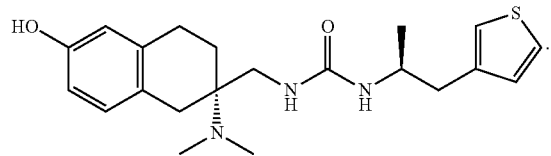 [SMILES: C[C@@H](Cc1ccsc1)NC(=O)NC[C@]1(N(C)C)CCc2cc(O)ccc2C1]

In embodiments, the compound has the formula:

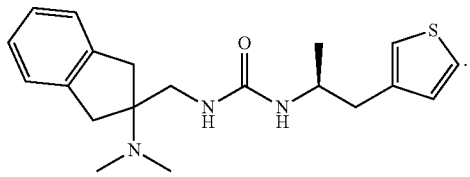 [SMILES: C[C@@H](Cc1ccsc1)NC(=O)NCC1(N(C)C)Cc2ccccc2C1]

In embodiments, the compound has the formula:

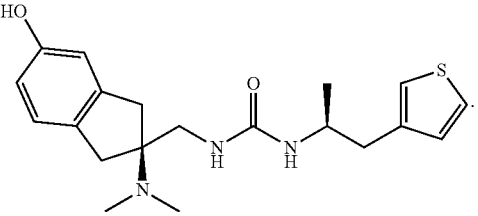 [SMILES: C[C@@H](Cc1ccsc1)NC(=O)NC[C@]1(N(C)C)Cc2ccc(O)cc2C1]

In embodiments, the compound has the formula:

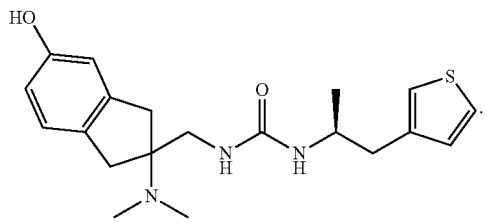 [SMILES: C[C@@H](Cc1ccsc1)NC(=O)NCC1(N(C)C)Cc2ccc(O)cc2C1]

In embodiments, the compound has the formula:

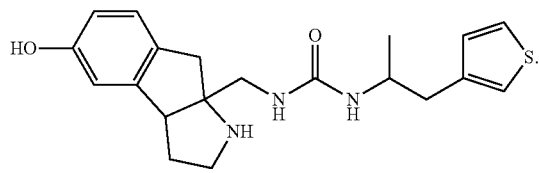 [SMILES: CC(Cc1ccsc1)NC(=O)NCC12Cc3ccc(O)cc3C1CCN2]

In embodiments, the compound has the formula:

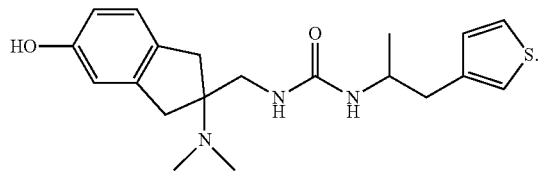 [SMILES: CC(Cc1ccsc1)NC(=O)NCC1(N(C)C)Cc2ccc(O)cc2C1]

In embodiments, the compound has the formula:

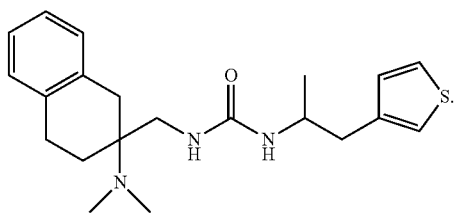 [SMILES: CC(Cc1ccsc1)NC(=O)NCC1(N(C)C)CCc2ccccc2C1]

In embodiments, the compound has the formula:

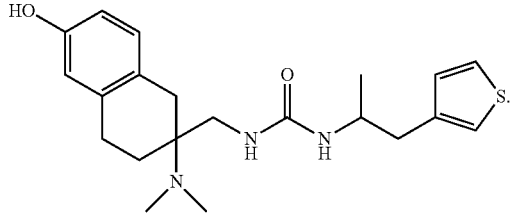 [SMILES: CC(Cc1ccsc1)NC(=O)NCC1(N(C)C)CCc2cc(O)ccc2C1]

In embodiments, the compound has the formula:

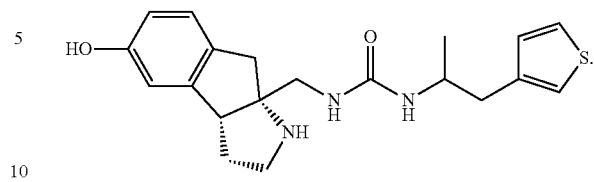

In embodiments, the compound has the formula:

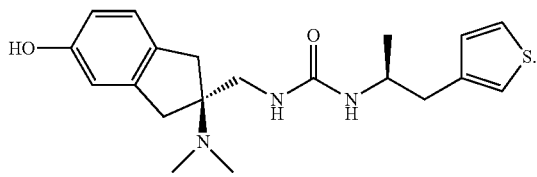 [SMILES: C[C@@H](Cc1ccsc1)NC(=O)NC[C@@]1(N(C)C)Cc2ccc(O)cc2C1]

In embodiments, the compound has the formula:

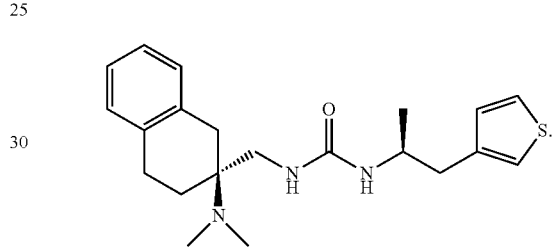

In embodiments, the compound has the formula:

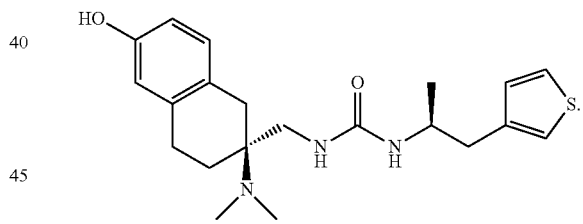

In embodiments, the compound has the formula:

DD 262 P1/P2

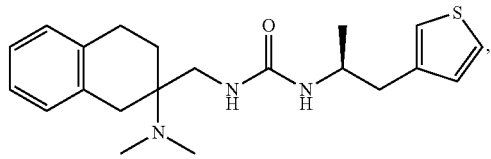

DD 272A/B

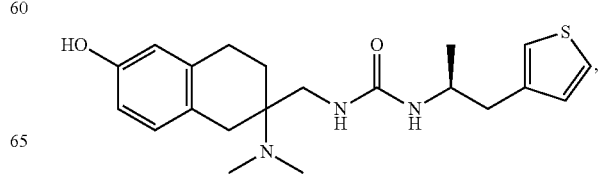

-continued
DD 277
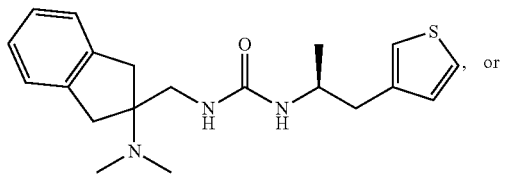, or
DD 297A/B
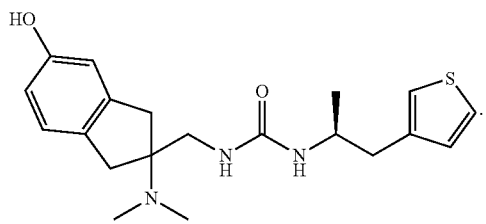.
The letter code, e.g., 'A' or 'B' or 'P1' or 'P2', as used herein corresponds to a particular stereochemistry, e.g.,
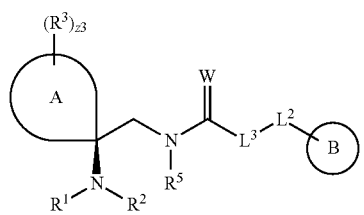
may refer to 'A' and
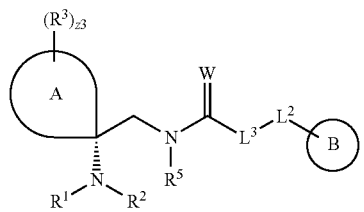
may refer to 'B'. Alternatively,
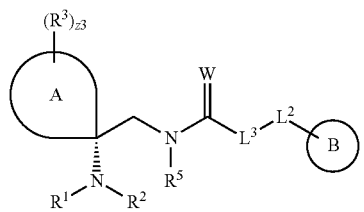
may refer to 'A' and
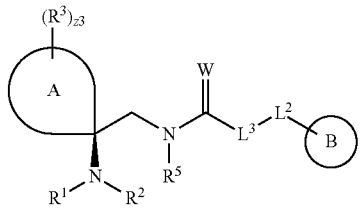
may refer to 'B'.
In embodiments, the compound has the formula:
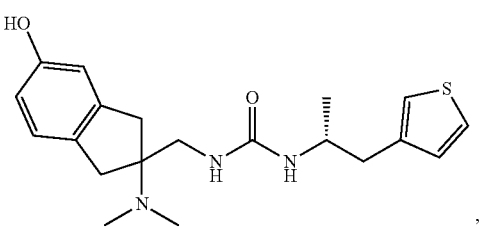,
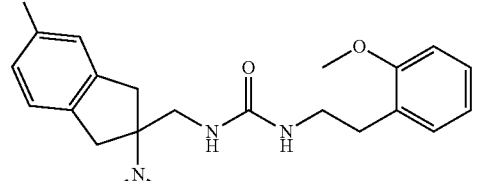,
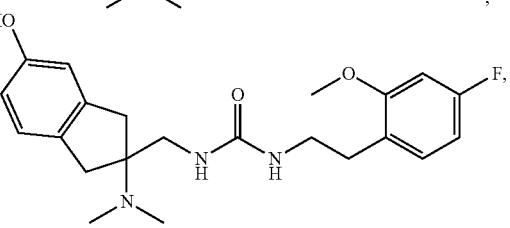,
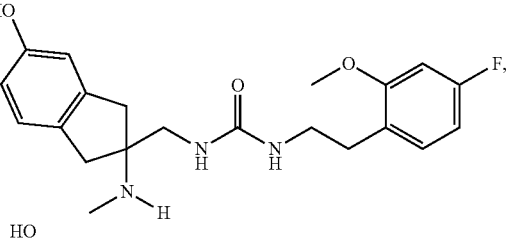,
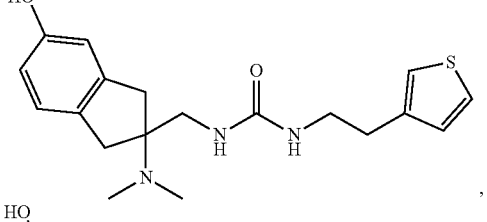,
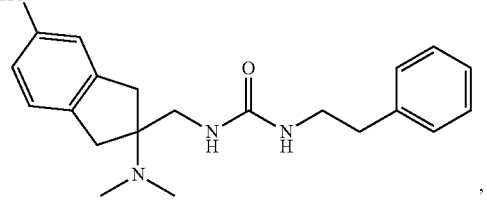,

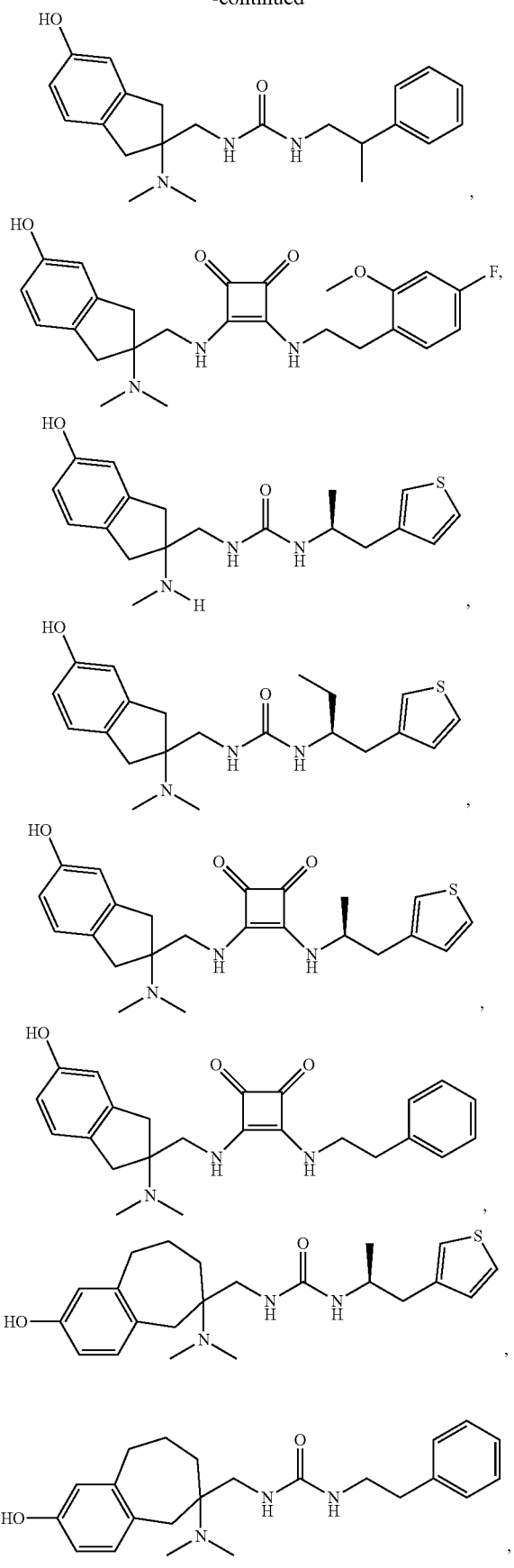

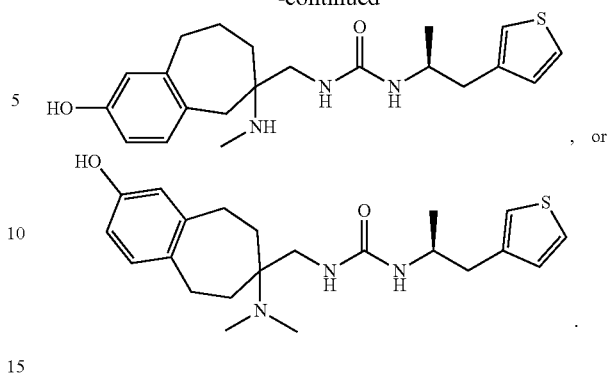

, or

In embodiments, the compound does not have the formula:

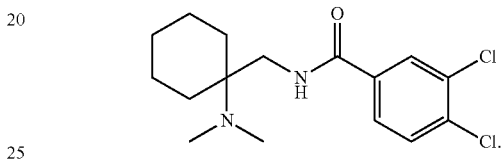

In embodiments, the compound does not have the formula:

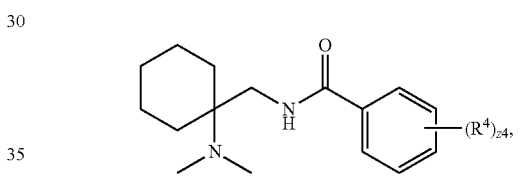

wherein $R^4$ and z4 are as described herein. In embodiments, $R^4$ is not halogen. In embodiments, z4 is 0 or 1.

In embodiments, the compound does not have the formula:

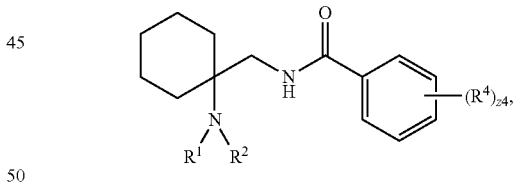

wherein $R^1$, $R^2$, $R^4$, and z4 are as described herein. In embodiments, $R^3$ is not hydrogen. In embodiments, Ring A is not an unsubstituted cyclohexyl. In embodiments, Ring B is not a dichloro-substituted phenyl. In embodiments, Ring B is not a substituted phenyl.

In embodiments, $L^2$ is not a bond. In embodiments, $L^3$ is not a bond. In embodiments, when $L^2$ is a bond, $L^3$ is not a bond. In embodiments, when $L^3$ is a bond, $L^2$ is not a bond.

III. Pharmaceutical Compositions

In an aspect is provided a pharmaceutical composition including a compound described herein (including in embodiments, examples, figures, or tables) and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent (e.g., an additional pain reliever, anti-fibrotic agent, anti-inflammatory agent).

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

IV. Methods of Treatment

In an aspect is provided a method of treating pain in a subject in need of the treatment, the method including administering an effective amount of a compound described herein (including in embodiments, examples, figures, or tables). In an aspect is provided a method of treating pain in a subject in need of the treatment, the method including administering to the subject an effective amount of a compound described herein (including in embodiments, examples, figures, or tables). In embodiments, the compound has the formula:

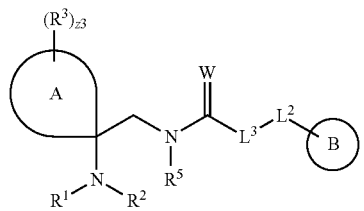

wherein, W is O or S; Ring A is a monocyclic cycloalkyl, monocyclic heterocycloalkyl, fused ring aryl, or fused ring heteroaryl; Ring B is independently substituted or unsubstituted cycloalkyl, substituted or unsubstituted heterocycloalkyl, substituted or unsubstituted aryl, or substituted or unsubstituted heteroaryl; $L^2$ is a bond, substituted or unsubstituted ($C_1$-$C_5$) alkylene, or substituted or unsubstituted 2 to 5 membered heteroalkylene; $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OC_2HF$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^1$ and $R^2$ may optionally be joined to form a substituted or unsubstituted 3 to 6 membered heterocycloalkyl or substituted or unsubstituted 5 to 6 membered heteroaryl; $R^1$ and $R^3$ may optionally be joined to form a substituted or unsubstituted 3 to 6 membered heterocycloalkyl or substituted or unsubstituted 5 to 6 membered heteroaryl; $R^2$ and $R^3$ may optionally be joined to form a substituted or unsubstituted 3 to 6 membered heterocycloalkyl or substituted or unsubstituted 5 to 6 membered heteroaryl; $L^3$ is a bond, —O—, —N($R^6$)—, or —$CH_2$—; $R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; $R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, the compound has the formula:

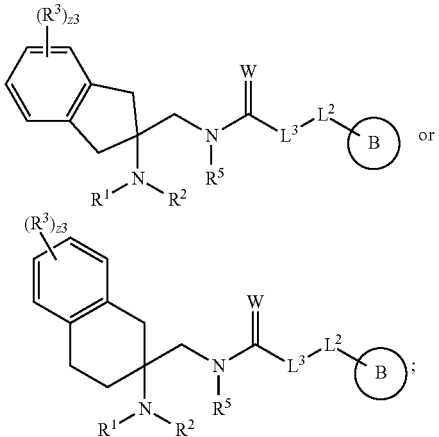

wherein, Ring B is independently substituted or unsubstituted cycloalkyl, substituted or unsubstituted heterocycloalkyl, substituted or unsubstituted aryl, or substituted or unsubstituted heteroaryl; $L^2$ is substituted or unsubstituted ($C_2$-$C_5$) alkylene, or substituted or unsubstituted 2 to 5 membered heteroalkylene; $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —CX₃, —CN, —N₃, —SO$_n$R¹⁰, —SO$_v$NR⁷R⁸, —NHNR⁷R⁸, —ONR⁷R⁸, —NHC=(O)NHNR⁷R⁸, —NHC=(O)NR⁷R⁸, —N(O)$_m$, —NR⁷R⁸, —C(O)R⁹, —C(O)—OR⁹, —C(O)NR⁷R⁸, —OR¹⁰, —NR⁷SO₂R¹⁰, —NR⁷C=(O)R⁹, —NR⁷C(O)OR⁹, —NR⁷OR⁹, —CHX₂, —CH₂X, —OCX₃, —OCHX₂, —OCH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R³ substituents may optionally be joined to form a substituted or unsubstituted cycloalkyl, substituted or unsubstituted heterocycloalkyl, substituted or unsubstituted aryl, or substituted or unsubstituted heteroaryl; R⁷, R⁸, R⁹, and R¹⁰ are independently hydrogen, halogen, —CF₃, —CN, —N₃, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, —OCF₃, —OCHF₂, —OCH₂F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁷ and R⁸ substituents bonded to the same nitrogen atom may optionally be joined to form a substituted or unsubstituted heterocycloalkyl or substituted or unsubstituted heteroaryl; R¹ and R² may optionally be joined to form a substituted or unsubstituted 3 to 6 membered heterocycloalkyl or substituted or unsubstituted 5 to 6 membered heteroaryl; R¹ and R³ may optionally be joined to form a substituted or unsubstituted 3 to 6 membered heterocycloalkyl or substituted or unsubstituted 5 to 6 membered heteroaryl; R² and R³ may optionally be joined to form a substituted or unsubstituted 3 to 6 membered heterocycloalkyl or substituted or unsubstituted 5 to 6 membered heteroaryl; L³ is —O— or —N(R⁶)—; R⁵ is hydrogen, —CF₃, —CN, —COOH, —CONH₂, —CHF₂, —CH₂F, substituted or unsubstituted (C₁-C₅) alkyl, or substituted or unsubstituted 2 to 5 membered heteroalkyl; R⁶ is hydrogen, —CF₃, —CN, —COOH, —CONH₂, —CHF₂, —CH₂F, substituted or unsubstituted (C₁-C₅) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, the compound has the formula:

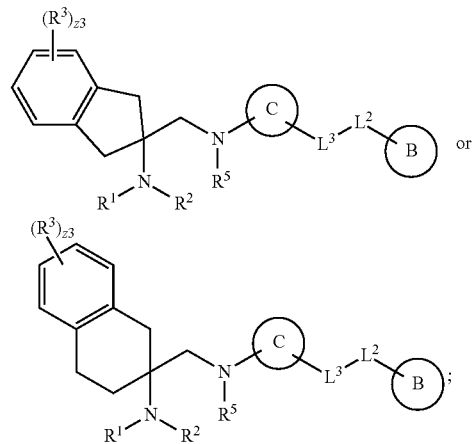

wherein, Ring B is independently substituted or unsubstituted cycloalkyl, substituted or unsubstituted heterocycloalkyl, substituted or unsubstituted aryl, or substituted or unsubstituted heteroaryl; Ring C is substituted or unsubstituted cycloalkylene, substituted or unsubstituted heterocycloalkylene, substituted or unsubstituted arylene, or substituted or unsubstituted heteroarylene; L² is substituted or unsubstituted (C₂-C₅) alkylene, or substituted or unsubstituted 2 to 5 membered heteroalkylene; R¹ and R² are independently hydrogen, halogen, —CF₃, —CN, —N₃, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, —OCF₃, —OCHF₂, —OCH₂F, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; R³ is independently hydrogen, halogen, —CX₃, —CN, —N₃, —SO$_n$R¹⁰, —SO$_v$NR⁷R⁸, —NHNR⁷R⁸, —ONR⁷R⁸, —NHC=(O)NHNR⁷R⁸, —NHC=(O)NR⁷R⁸, —N(O)$_m$, —NR⁷R⁸, —C(O)R⁹, —C(O)—OR⁹, —C(O)NR⁷R⁸, —OR¹⁰, —NR⁷SO₂R¹⁰, —NR⁷C=(O)R⁹, —NR⁷C(O)OR⁹, —NR⁷OR⁹, —CHX₂, —CH₂X, —OCX₃, —OCHX₂, —OCH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R³ substituents may optionally be joined to form a substituted or unsubstituted cycloalkyl, substituted or unsubstituted heterocycloalkyl, substituted or unsubstituted aryl, or substituted or unsubstituted heteroaryl; R⁷, R⁸, R⁹, and R¹⁰ are independently hydrogen, halogen, —CF₃, —CN, —N₃, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)OH, —NHOH, —CHF₂, —CH₂F, —OCF₃, —OCHF₂, —OCH₂F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁷ and R⁸ substituents bonded to the same nitrogen atom may optionally be joined to form a substituted or unsubstituted heterocycloalkyl or substituted or unsubstituted heteroaryl; R¹ and R² may optionally be joined to form a substituted or unsubstituted 3 to 6 membered heterocycloalkyl or substituted or unsubstituted 5 to 6 membered heteroaryl; R¹ and R³ may optionally be joined to form a substituted or unsubstituted 3 to 6 membered heterocycloalkyl or substituted or unsubstituted 5 to 6 membered heteroaryl; R² and R³ may optionally be joined to form a substituted or unsubstituted 3 to 6 membered heterocycloalkyl or substituted or unsubstituted 5 to 6 membered heteroaryl; L³ is —O— or —N(R⁶)—; R⁵ is hydrogen, —CF₃, —CN, —COOH, —CONH₂, —CHF₂, —CH₂F, substituted or unsubstituted (C₁-C₅) alkyl, or substituted or unsubstituted 2 to 5 membered heteroalkyl; R⁶ is hydrogen, —CF₃, —CN, —COOH, —CONH₂, —CHF₂, —CH₂F, substituted or unsubstituted (C₁-C₅) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

An appropriate or effective amount is an amount sufficient to provide the desired therapeutic effect (e.g., treat or alleviate pain or treat or reduce inflammation). Compounds of the invention may be used in combination with other compounds of the invention or with other drugs that may also be useful in the treatment, prevention, or the suppression of pain. In embodiments, the pain is associated with pulmonary edema, kidney stones, minor injuries, wound healing, skin wound healing, vaginitis, candidiasis, lumbar spondylanhrosis, lumbar spondylarthrosis, vascular diseases, migraine headaches, sinus headaches, tension headaches, dental pain, periarteritis *nodosa*, thyroiditis, aplastic anemia, Hodgkin's disease, sclerodoma, rheumatic fever, type I diabetes, type II diabetes, myasthenia gravis, multiple sclerosis, sarcoidosis, nephrotic syndrome, Behcet's syndrome, polymyositis, gingivitis, hypersensitivity, swelling occurring after injury, or myocardial ischemia, or osteoarthritis. In embodiments, the pain is post surgical pain. In embodiments, the compounds described herein are used to treat moderate or severe acute pain. In embodiments, the pain is paroxysmal spontaneous pain, steady pain, allodynia associated with postherpetic neuralgia. In embodiments, the pain is cancer-related pain.

In embodiments, the pain is associated with invasive procedures (e.g., lumbar puncture, biopsy, surgical intervention). In embodiments, the pain is associated with mechanical or metabolic injury to the nervous system, tumor infiltration of nerves or nerve roots, or exposure to chemotherapeutic agents or radiation therapy.

In embodiments, the pain is acute pain (e.g., post-surgical pain). In embodiments, the pain is chronic pain. In embodiments, chronic pain is pain that has persisted for at least 1 month. In embodiments, chronic pain is pain that has persisted for at least 2 months. In embodiments, chronic pain is pain that has persisted for at least 3 months. In embodiments, chronic pain is pain that has persisted for at least 4 months. In embodiments, chronic pain is pain that has persisted for at least 5 months. In embodiments, chronic pain is pain that has persisted for at least 6 months. In embodiments, the method does not include an increased risk of respiratory depression. In embodiments, the method does not include respiratory depression. In embodiments, the method does not include an increased risk of constipation. In embodiments, the method does not include constipation. In embodiments, the pain is affective pain. Affective pain may be assessed using an objective psychophysiological measure, subjective ratings, (e.g., the eye-blink component of the startle reflex), or methods known in the art (e.g., methods described herein). In embodiments, an increased risk indicates an elevated probability of experiencing a symptom (e.g., constipation, respiratory depression). In embodiments, an increased risk is 1%, 2%, 3%, 4%, 5%, 10%, 15%, 25%, 30%, 35%, 40%, 50%, 60%, 70%, 80%, 90%, 100%, 200%, 300%, 400%, 500%, or 1000%. In embodiments, an increased risk is about 1%, 2%, 3%, 4%, 5%, 10%, 15%, 25%, 30%, 35%, 40%, 50%, 60%, 70%, 80%, 90%, 100%, 200%, 300%, 400%, 500%, or about 1000%.

In an aspect is provided a method of treating opioid overdose in a subject in need of the treatment, the method including administering an effective amount of a compound described herein (including in embodiments, examples, figures, or tables). In an aspect is provided a method of treating opioid overdose in a subject in need of the treatment, the method including administering to the subject an effective amount of a compound described herein (including in embodiments, examples, figures, or tables).

In an aspect is provided a method of treating addiction in a subject in need of the treatment, the method including administering an effective amount of a compound described herein (including in embodiments, examples, figures, or tables). In an aspect is provided a method of treating addiction in a subject in need of the treatment, the method including administering to the subject an effective amount of a compound described herein (including in embodiments, examples, figures, or tables).

In embodiments, the addiction is opioid addiction. In embodiments, the addiction is heroin addiction. In embodiments, the addiction is oxycodone addiction. In embodiments, the addiction is morphine addiction. In embodiments, the addiction is fentanyl addiction. In embodiments, the addiction is codeine addiction. In embodiments, the addiction is nicotine addiction. In embodiments, the method does not include an increased risk of respiratory depression. In embodiments, the method does not include respiratory depression. In embodiments, the method does not include an increased risk of constipation. In embodiments, the method does not include constipation.

In an aspect is provided a method of treating a psychiatric disorder in a subject in need of the treatment, the method including administering an effective amount of a compound described herein (including in embodiments, examples, figures, or tables). In an aspect is provided a method of treating a psychiatric disorder in a subject in need of the treatment, the method including administering to the subject an effective amount of a compound described herein (including in embodiments, examples, figures, or tables).

In embodiments, the psychiatric disorder is depression. In embodiments, the psychiatric disorder is anxiety. In embodiments, the method does not include an increased risk of respiratory depression. In embodiments, the method does not include respiratory depression. In embodiments, the method does not include an increased risk of constipation. In embodiments, the method does not include constipation.

In an aspect is provided a method of treating drug poisoning in a subject in need of the treatment, the method including administering an effective amount of a compound described herein (including in embodiments, examples, figures, or tables). In an aspect is provided a method of treating drug poisoning in a subject in need of the treatment, the method including administering to the subject an effective amount of a compound described herein (including in embodiments, examples, figures, or tables).

In embodiments, the drug is an opioid. In embodiments, the drug is an opiate. In embodiments, the drug is heroin. In embodiments, the drug is fentanyl. In embodiments, the drug is morphine. In embodiments, the drug is oxycodone.

In an aspect is provided a compound, (e.g., a compound described herein) for use as a medicament for the treatment of pain in a subject in need thereof.

In an aspect is provided a compound, (e.g., a compound described herein) for use as a medicament for the treatment of opioid overdose in a subject in need thereof.

In an aspect is provided a compound, (e.g., a compound described herein) for use as a medicament for the treatment of addiction in a subject in need thereof.

In an aspect is provided a compound, (e.g., a compound described herein) for use as a medicament for the treatment of psychiatric disorder in a subject in need thereof.

The compounds of the invention (i.e. compounds described herein, including in embodiments, examples, figures, tables) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation or anti-cancer agents).

V. Methods of Modulating Activity

In an aspect is provided a method of modulating the activity of an opioid receptor protein, the method including contacting the opioid receptor protein with an effective amount of a compound described herein (including in embodiments, examples, figures, or tables).

In embodiments, the compound has the formula:

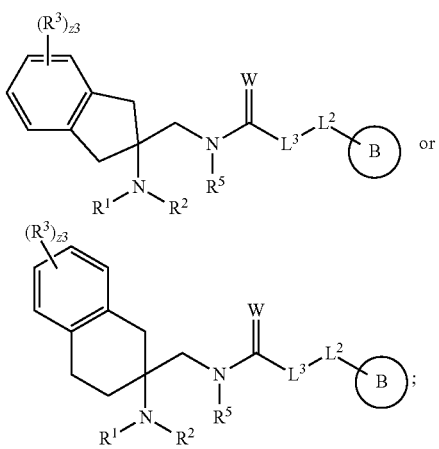

wherein, Ring B is independently substituted or unsubstituted cycloalkyl, substituted or unsubstituted heterocycloalkyl, substituted or unsubstituted aryl, or substituted or unsubstituted heteroaryl; $L^2$ is substituted or unsubstituted $(C_2-C_5)$ alkylene, or substituted or unsubstituted 2 to 5 membered heteroalkylene; $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^1$ and $R^2$ may optionally be joined to form a substituted or unsubstituted 3 to 6 membered heterocycloalkyl or substituted or unsubstituted 5 to 6 membered heteroaryl; $R^1$ and $R^3$ may optionally be joined to form a substituted or unsubstituted 3 to 6 membered heterocycloalkyl or substituted or unsubstituted 5 to 6 membered heteroaryl; $R^2$ and $R^3$ may optionally be joined to form a substituted or unsubstituted 3 to 6 membered heterocycloalkyl or substituted or unsubstituted 5 to 6 membered heteroaryl; $L^3$ is —O— or —N($R^6$)—; $R^5$ is hydrogen, —$CF_3$, —CN, —COOH, —$CONH_2$, —$CHF_2$, —$CH_2F$, substituted or unsubstituted $(C_1-C_5)$ alkyl, or substituted or unsubstituted 2 to 5 membered heteroalkyl; $R^6$ is hydrogen, —$CF_3$, —CN, —COOH, —$CONH_2$, —$CHF_2$, —$CH_2F$, substituted or unsubstituted $(C_1-C_5)$ alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, the compound has the formula:

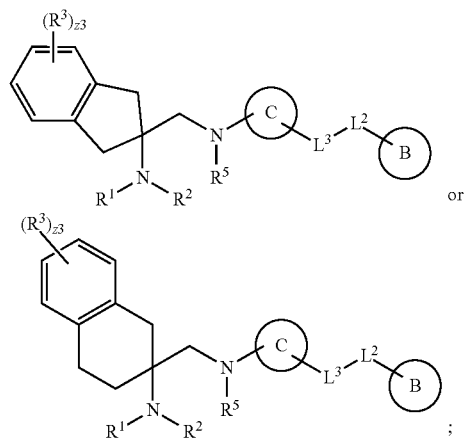

wherein, Ring B is independently substituted or unsubstituted cycloalkyl, substituted or unsubstituted heterocycloalkyl, substituted or unsubstituted aryl, or substituted or unsubstituted heteroaryl; Ring C is substituted or unsubstituted cycloalkylene, substituted or unsubstituted heterocycloalkylene, substituted or unsubstituted arylene, or substituted or unsubstituted heteroarylene; $L^2$ is substituted or unsubstituted $(C_2-C_5)$ alkylene, or substituted or unsubstituted 2 to 5 membered heteroalkylene; $R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl; $R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —OR$^{10}$, —NR$^7$SO$_2$R$^{10}$, —NR$^7$C=(O)R$^9$, —NR$^7$C(O)OR$^9$, —NR$^7$OR$^9$, —CHX$_2$, —CH$_2$X, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^3$ substituents may optionally be joined to form a substituted or unsubstituted cycloalkyl, substituted or unsubstituted heterocycloalkyl, substituted or unsubstituted aryl, or substituted or unsubstituted heteroaryl; R$^7$, R$^8$, R$^9$, and R$^{10}$ are independently hydrogen, halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^1$ and R$^2$ may optionally be joined to form a substituted or unsubstituted 3 to 6 membered heterocycloalkyl or substituted or unsubstituted 5 to 6 membered heteroaryl; R$^1$ and R$^3$ may optionally be joined to form a substituted or unsubstituted 3 to 6 membered heterocycloalkyl or substituted or unsubstituted 5 to 6 membered heteroaryl; R$^2$ and R$^3$ may optionally be joined to form a substituted or unsubstituted 3 to 6 membered heterocycloalkyl or substituted or unsubstituted 5 to 6 membered heteroaryl; L$^3$ is —O— or —N(R$^6$)—; R$^5$ is hydrogen, —CF$_3$, —CN, —COOH, —CONH$_2$, —CHF$_2$, —CH$_2$F, substituted or unsubstituted (C$_1$-C$_5$) alkyl, or substituted or unsubstituted 2 to 5 membered heteroalkyl; R$^6$ is hydrogen, —CF$_3$, —CN, —COOH, —CONH$_2$, —CHF$_2$, —CH$_2$F, substituted or unsubstituted (C$_1$-C$_5$) alkyl, or substituted or unsubstituted 2 to 5 membered heteroalkyl; z3 is an integer from to 1 to 10; m and v are independently 1 or 2; n is independently an integer from 0 to 4; and X is independently —Cl, —Br, —I, or —F.

In embodiments, modulating is activating. In embodiments, activating includes a change of 10%, 20%, 30%, 40%, 50%, 60%, 70%, 80%, 90% or greater as compared to a control level. In embodiments, modulating is inhibiting. In embodiments, inhibiting includes a change of 10%, 20%, 30%, 40%, 50%, 60%, 70%, 80%, 90% or greater as compared to a control level can include complete elimination.

In embodiments, the opioid receptor is a human mu opioid receptor.

In embodiments, the method does not include modulating arrestin function. In embodiments, the method does not include increasing arrestin function. In embodiments, the method does not include activating arrestin. In embodiments, the method does not include modulating the activity of a human kappa opioid receptor. In embodiments, the method does not include modulating the activity of a human delta opioid receptor. In embodiments, the method does not include modulating the activity of a human nociceptin receptor.

In embodiments, the method includes modulating human mu opioid receptor function at least 2-fold more than modulating arrestin function. In embodiments, the method includes modulating mu opioid receptor function at least 2-fold more than modulating human kappa opioid receptor function. In embodiments, the method includes modulating mu opioid receptor function at least 2-fold more than modulating human delta opioid receptor function. In embodiments, the method includes modulating mu opioid receptor function at least 2-fold more than modulating human nociceptin receptor function.

In embodiments, the method includes modulating human mu opioid receptor function at least 5-fold more than modulating arrestin function. In embodiments, the method includes modulating mu opioid receptor function at least 5-fold more than modulating human kappa opioid receptor function. In embodiments, the method includes modulating mu opioid receptor function at least 5-fold more than modulating human delta opioid receptor function. In embodiments, the method includes modulating mu opioid receptor function at least 5-fold more than modulating human nociceptin receptor function.

In embodiments, the method includes modulating human mu opioid receptor function at least 10-fold more than modulating arrestin function. In embodiments, the method includes modulating mu opioid receptor function at least 10-fold more than modulating human kappa opioid receptor function. In embodiments, the method includes modulating mu opioid receptor function at least 10-fold more than modulating human delta opioid receptor function. In embodiments, the method includes modulating mu opioid receptor function at least 10-fold more than modulating human nociceptin receptor function.

In embodiments, the method includes modulating human mu opioid receptor function at least 100-fold more than modulating arrestin function. In embodiments, the method includes modulating mu opioid receptor function at least 100-fold more than modulating human kappa opioid receptor function. In embodiments, the method includes modulating mu opioid receptor function at least 100-fold more than modulating human delta opioid receptor function. In embodiments, the method includes modulating mu opioid receptor function at least 100-fold more than modulating human nociceptin receptor function.

In embodiments, the method includes modulating human mu opioid receptor function at least 1000-fold more than modulating arrestin function. In embodiments, the method includes modulating mu opioid receptor function at least 1000-fold more than modulating human kappa opioid receptor function. In embodiments, the method includes modulating mu opioid receptor function at least 1000-fold more than modulating human delta opioid receptor function. In embodiments, the method includes modulating mu opioid receptor function at least 1000-fold more than modulating human nociceptin receptor function.

In embodiments, the method includes modulating human mu opioid receptor function at least 10000-fold more than modulating arrestin function. In embodiments, the method includes modulating mu opioid receptor function at least 10000-fold more than modulating human kappa opioid receptor function. In embodiments, the method includes modulating mu opioid receptor function at least 10000-fold more than modulating human delta opioid receptor function. In embodiments, the method includes modulating mu opioid receptor function at least 10000-fold more than modulating human nociceptin receptor function.

In embodiments, the method includes modulating human mu opioid receptor G protein-mediated function at least 2-fold more than modulating arrestin function. In embodiments, the method includes modulating mu opioid receptor G protein-mediated function at least 2-fold more than modulating human kappa opioid receptor function. In embodiments, the method includes modulating mu opioid receptor G protein-mediated function at least 2-fold more than modulating human delta opioid receptor function. In embodiments, the method includes modulating mu opioid receptor G protein-mediated function at least 2-fold more than modulating human nociceptin receptor function.

In embodiments, the method includes modulating human mu opioid receptor G protein-mediated function at least 5-fold more than modulating arrestin function. In embodiments, the method includes modulating mu opioid receptor G protein-mediated function at least 5-fold more than modulating human kappa opioid receptor function. In embodiments, the method includes modulating mu opioid receptor G protein-mediated function at least 5-fold more than modulating human delta opioid receptor function. In embodiments, the method includes modulating mu opioid receptor G protein-mediated function at least 5-fold more than modulating human nociceptin receptor function.

In embodiments, the method includes modulating human mu opioid G protein-mediated receptor function at least 10-fold more than modulating arrestin function. In embodiments, the method includes modulating mu opioid receptor G protein-mediated function at least 10-fold more than modulating human kappa opioid receptor function. In embodiments, the method includes modulating mu opioid receptor G protein-mediated function at least 10-fold more than modulating human delta opioid receptor function. In embodiments, the method includes modulating mu opioid receptor G protein-mediated function at least 10-fold more than modulating human nociceptin receptor function.

In embodiments, the method includes modulating human mu opioid receptor G protein-mediated function at least 100-fold more than modulating arrestin function. In embodiments, the method includes modulating mu opioid receptor G protein-mediated function at least 100-fold more than modulating human kappa opioid receptor function. In embodiments, the method includes modulating mu opioid receptor G protein-mediated function at least 100-fold more than modulating human delta opioid receptor function. In embodiments, the method includes modulating mu opioid receptor G protein-mediated function at least 100-fold more than modulating human nociceptin receptor function.

In embodiments, the method includes modulating human mu opioid receptor G protein-mediated function at least 1000-fold more than modulating arrestin function. In embodiments, the method includes modulating mu opioid receptor G protein-mediated function at least 1000-fold more than modulating human kappa opioid receptor function. In embodiments, the method includes modulating mu opioid receptor G protein-mediated function at least 1000-fold more than modulating human delta opioid receptor function. In embodiments, the method includes modulating mu opioid receptor G protein-mediated function at least 1000-fold more than modulating human nociceptin receptor function.

In embodiments, the method includes modulating human mu opioid receptor G protein-mediated function at least 10000-fold more than modulating arrestin function. In embodiments, the method includes modulating mu opioid receptor G protein-mediated function at least 10000-fold more than modulating human kappa opioid receptor function. In embodiments, the method includes modulating mu opioid receptor G protein-mediated function at least 10000-fold more than modulating human delta opioid receptor function. In embodiments, the method includes modulating mu opioid receptor G protein-mediated function at least 10000-fold more than modulating human nociceptin receptor function.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Embodiments

Embodiment 1. A compound having the formula:

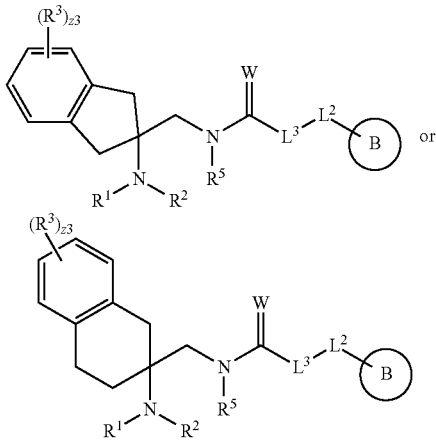

wherein,

Ring B is independently substituted or unsubstituted cycloalkyl, substituted or unsubstituted heterocycloalkyl, substituted or unsubstituted aryl, or substituted or unsubstituted heteroaryl;

$L^2$ is substituted or unsubstituted ($C_2$-$C_5$) alkylene, or substituted or unsubstituted 2 to 5 membered heteroalkylene;

$R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl;

$R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl;

two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl;

$R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ and $R^8$ substituents bonded to the same nitrogen atom may optionally be joined to form a substituted or unsubstituted heterocycloalkyl or substituted or unsubstituted heteroaryl;

$R^1$ and $R^2$ may optionally be joined to form a substituted or unsubstituted 3 to 6 membered heterocycloalkyl or substituted or unsubstituted 5 to 6 membered heteroaryl;

$R^1$ and $R^3$ may optionally be joined to form a substituted or unsubstituted 3 to 6 membered heterocycloalkyl or substituted or unsubstituted 5 to 6 membered heteroaryl;

$R^2$ and $R^3$ may optionally be joined to form a substituted or unsubstituted 3 to 6 membered heterocycloalkyl or substituted or unsubstituted 5 to 6 membered heteroaryl;

$L^3$ is —O— or —N($R^6$)—;

$R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl;

$R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl;

z3 is an integer from to 1 to 10;
m and v are independently 1 or 2;
n is independently an integer from 0 to 4; and
X is independently —Cl, —Br, —I, or —F.

Embodiment 2. A compound having the formula:

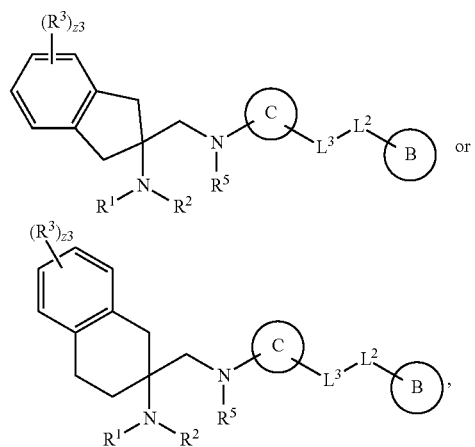

wherein,
Ring B is independently substituted or unsubstituted cycloalkyl, substituted or unsubstituted heterocycloalkyl, substituted or unsubstituted aryl, or substituted or unsubstituted heteroaryl;

Ring C is substituted or unsubstituted cycloalkylene, substituted or unsubstituted heterocycloalkylene, substituted or unsubstituted arylene, or substituted or unsubstituted heteroarylene;

$L^2$ is substituted or unsubstituted ($C_2$-$C_5$) alkylene, or substituted or unsubstituted 2 to 5 membered heteroalkylene;

$R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, or substituted or unsubstituted heterocycloalkyl, substituted or unsubstituted aryl, or substituted or unsubstituted heteroaryl;

$R^3$ is independently hydrogen, halogen, —$CX_3$, —CN, —$N_3$, —$SO_nR^{10}$, —$SO_vNR^7R^8$, —$NHNR^7R^8$, —$ONR^7R^8$, —NHC=(O)$NHNR^7R^8$, —NHC=(O)$NR^7R^8$, —N(O)$_m$, —$NR^7R^8$, —C(O)$R^9$, —C(O)—$OR^9$, —C(O)$NR^7R^8$, —$OR^{10}$, —$NR^7SO_2R^{10}$, —$NR^7C$=(O)$R^9$, —$NR^7C(O)OR^9$, —$NR^7OR^9$, —$CHX_2$, —$CH_2X$, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl;

$R^7$, $R^8$, $R^9$, and $R^{10}$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ and $R^8$ substituents bonded to the same nitrogen atom may optionally be joined to form a substituted or unsubstituted heterocycloalkyl or substituted or unsubstituted heteroaryl;

$R^1$ and $R^2$ may optionally be joined to form a substituted or unsubstituted 3 to 6 membered heterocycloalkyl or substituted or unsubstituted 5 to 6 membered heteroaryl;

$R^1$ and $R^3$ may optionally be joined to form a substituted or unsubstituted 3 to 6 membered heterocycloalkyl or substituted or unsubstituted 5 to 6 membered heteroaryl;

$R^2$ and $R^3$ may optionally be joined to form a substituted or unsubstituted 3 to 6 membered heterocycloalkyl or substituted or unsubstituted 5 to 6 membered heteroaryl;

$L^3$ is —O— or —N($R^6$)—;

$R^5$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl;

$R^6$ is hydrogen, —$CF_3$, —CN, —COOH, —$CONH_2$, —$CHF_2$, —$CH_2F$, substituted or unsubstituted ($C_1$-$C_5$) alkyl, or substituted or unsubstituted 2 to 5 membered heteroalkyl;

z3 is an integer from to 1 to 10;
m and v are independently 1 or 2;

n is independently an integer from 0 to 4; and
X is independently —Cl, —Br, —I, or —F.

Embodiment 3. The compound of claim 1, having the formula:

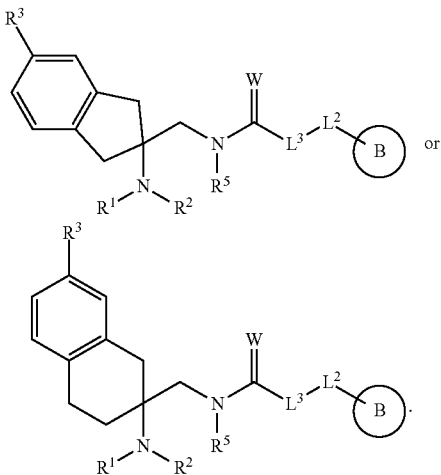

or

Embodiment 4. The compound of any one of embodiments 1 to 3, wherein $R^3$ is independently halogen, —NHNR$^7$R$^8$, —ONR$^7$R$^8$, —NHC=(O)NHNR$^7$R$^8$, —NHC=(O)NR$^7$R$^8$, —N(O)$_m$, —NR$^7$R$^8$, —C(O)R$^9$, —C(O)—OR$^9$, —C(O)NR$^7$R$^8$, —OR$^{10}$, —NR$^7$C=(O)R$^9$, —NR$^7$C(O)OR$^9$, or —NR$^7$OR$^9$.

Embodiment 5. The compound of any one of embodiments 1 to 3, wherein $R^3$ is independently halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted (C$_1$-C$_5$) alkyl, or substituted or unsubstituted 2 to 5 membered heteroalkyl.

Embodiment 6. The compound of any one of embodiments 1 to 3, wherein $R^3$ is independently halogen, —CF$_3$, —OH, —NH$_2$, —COOH, —CONH$_2$, —NHC=(O)NHNH$_2$, —NHC=(O)NH$_2$, —NHC=(O)H, —NHC(O)OH, or —NHOH.

Embodiment 7. The compound of any one of embodiments 1 to 3, wherein $R^3$ is independently —OH.

Embodiment 8. The compound of any one of embodiments 1 to 2, wherein $R^1$ and $R^3$ may optionally be joined to form a substituted or unsubstituted 3 to 6 membered heterocycloalkyl; or
$R^2$ and $R^3$ may optionally be joined to form a substituted or unsubstituted 3 to 6 membered heterocycloalkyl.

Embodiment 9. The compound of any one of embodiments 1 to 8, wherein Ring B is substituted or unsubstituted (C$_3$-C$_{10}$) cycloalkyl, substituted or unsubstituted 3 to 10 membered heterocycloalkyl, substituted or unsubstituted (C$_6$-C$_{10}$) aryl, or substituted or unsubstituted 5 to 10 membered heteroaryl.

Embodiment 10. The compound of embodiment 9, wherein Ring B is $R^4$-substituted or unsubstituted (C$_3$-C$_{10}$) cycloalkyl, $R^4$-substituted or unsubstituted 5 to 10 membered heterocycloalkyl, $R^4$-substituted or unsubstituted (C$_6$-C$_{10}$) aryl, or $R^4$-substituted or unsubstituted 5 to 10 membered heteroaryl;

$R^4$ is independently oxo, halogen, —CX$^a$$_3$, —CN, —N$_3$, —SO$_{n1}$R$^{14}$, —SO$_v$NR$^{11}$R$^{12}$, —NHNR$^{11}$R$^{12}$, —ONR$^{11}$R$^{12}$, —NHC=(O)NHNR$^{11}$R$^{12}$, —NHC=(O)NR$^{11}$R$^{12}$, —N(O)$_{m1}$, —NR$^{11}$R$^{12}$, —C(O)R$^{13}$, —C(O)—OR$^{13}$, —C(O)NR$^{11}$R$^{12}$, —OR$^{14}$, —NR$^{11}$SO$_2$R$^{14}$, —NR$^{11}$C=(O) R$^{13}$, —NR$^{11}$C(O)OR$^{13}$, —NR$^{11}$OR$^{13}$, —CHX$^a$$_2$, —CH$_2$X$^a$, —OCX$^a$$_3$, —OCHX$^a$$_2$, —OCH$_2$X$^a$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^4$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{11}$, $R^{12}$, $R^{13}$, and $R^{14}$ are independently hydrogen, halogen, —CF$_3$, —CN, —N$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ and $R^{12}$ substituents bonded to the same nitrogen atom may optionally be joined to form a substituted or unsubstituted heterocycloalkyl or substituted or unsubstituted heteroaryl;

m1 and v1 are independently 1 or 2;
n1 is independently an integer from 0 to 4; and
$X^a$ is independently —Cl, —Br, —I, or —F.

Embodiment 11. The compound of embodiment 9, wherein Ring B is $R^4$-substituted or unsubstituted thienyl, $R^4$-substituted or unsubstituted phenyl, $R^4$-substituted or unsubstituted benzothienyl, $R^4$-substituted or unsubstituted naphthyl, $R^4$-substituted or unsubstituted benzofuranyl, $R^4$-substituted or unsubstituted furanyl, $R^4$-substituted or unsubstituted pyrrolyl, or $R^4$-substituted or unsubstituted 2,3-dihydro-1H-indenyl.

Embodiment 12. The compound of any one of embodiments 1 to 11, wherein
Ring B is unsubstituted thienyl;
Ring B is unsubstituted phenyl;
Ring B is unsubstituted benzothienyl;
Ring B is para-methyl substituted phenyl;
Ring B is unsubstituted naphthyl; or
Ring B is unsubstituted 2,3-dihydro-1H-indenyl.

Embodiment 13. The compound of any one of embodiments 1 to 11, wherein Ring B is unsubstituted phenyl.

Embodiment 14. The compound of any one of embodiments 1 to 11, wherein Ring B is an unsubstituted 3-thienyl.

Embodiment 15. The compound of any one of embodiments 1 to 7, or 9 to 14, wherein $R^1$ is substituted or unsubstituted (C$_1$-C$_{12}$) alkyl.

Embodiment 16. The compound of any one of embodiments 1 to 7, or 9 to 14, wherein $R^1$ is substituted (C$_1$-C$_{12}$) alkyl, substituted with a substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

Embodiment 17. The compound of any one of embodiments 1 to 7, or 9 to 14, wherein $R^1$ is unsubstituted $(C_1-C_2)$ alkyl.

Embodiment 18. The compound of any one of embodiments 1 to 7, or 9 to 14, wherein $R^1$ is independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted $(C_1-C_5)$ alkyl, substituted or unsubstituted 2 to 5 membered heteroalkyl, substituted or unsubstituted $(C_3-C_6)$ cycloalkyl, or substituted or unsubstituted 3 to 6 membered heterocycloalkyl.

Embodiment 19. The compound of any one of embodiments 1 to 7, or 9 to 18, wherein $R^2$ is substituted or unsubstituted $(C_1-C_{12})$ alkyl.

Embodiment 20. The compound of any one of embodiments 1 to 7, or 9 to 18, wherein $R^2$ is substituted $(C_1-C_{12})$ alkyl, substituted with a substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

Embodiment 21. The compound of any one of embodiments 1 to 7, or 9 to 18, wherein $R^2$ is unsubstituted $(C_1-C_2)$ alkyl.

Embodiment 22. The compound of any one of embodiments 1 to 7, or 9 to 18, wherein $R^2$ is independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted $(C_1-C_5)$ alkyl, substituted or unsubstituted 2 to 5 membered heteroalkyl, substituted or unsubstituted $(C_3-C_6)$ cycloalkyl, or substituted or unsubstituted 3 to 6 membered heterocycloalkyl.

Embodiment 23. The compound of any one of embodiments 1 to 7, wherein $R^1$ and $R^2$ are unsubstituted methyl.

Embodiment 24. The compound of any one of embodiments 1 to 7, wherein $R^1$ and $R^2$ are joined to form a substituted or unsubstituted 3 to 6 membered heterocycloalkyl or substituted or unsubstituted 5 to 6 membered heteroaryl.

Embodiment 25. The compound of any one of embodiments 1 to 24, wherein $R^5$ is hydrogen, substituted or unsubstituted $(C_1-C_5)$ alkyl or substituted or unsubstituted 2 to 5 membered heteroalkyl.

Embodiment 26. The compound of any one of embodiments 1, 3 to 25, wherein W is O.

Embodiment 27. The compound of any one of embodiments 1 to 26, wherein $L^3$ is —$N(R^6)$—.

Embodiment 28. The compound of embodiment 27, wherein $R^6$ is hydrogen, substituted or unsubstituted $(C_1-C_5)$ alkyl or substituted or unsubstituted 2 to 5 membered heteroalkyl.

Embodiment 29. The compound of any one of embodiments 1 to 28, wherein $L^2$ is substituted or unsubstituted $(C_1-C_3)$ alkylene, or substituted or unsubstituted 2 to 5 membered heteroalkylene.

Embodiment 30. The compound of embodiment 1, having the formula:

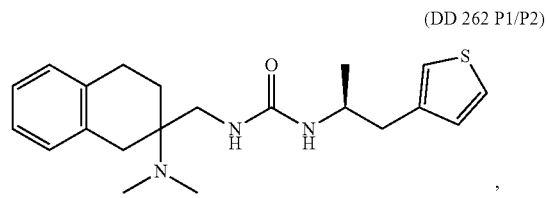
(DD 262 P1/P2)

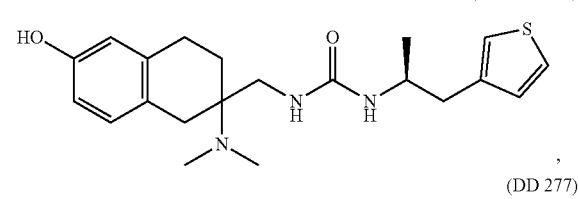
(DD 272 A/B)

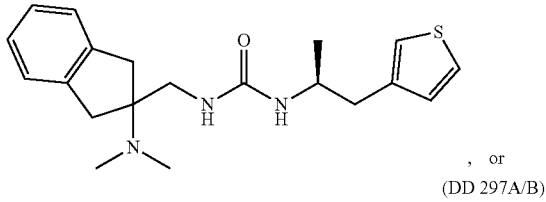
(DD 277)

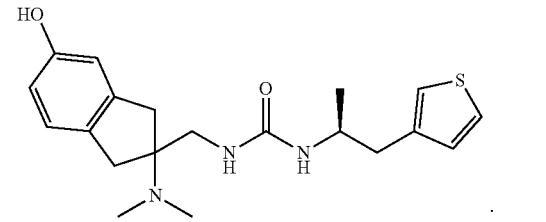
(DD 297A/B)

Embodiment 31. The compound of embodiment 1, having the formula:

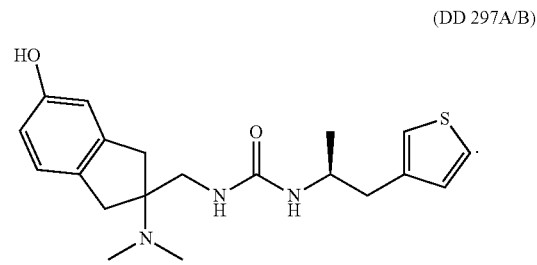 [SMILES: C[C@@H](Cc1ccsc1)NC(=O)NCC1(N(C)C)Cc2ccc(O)cc2C1]
(DD 297A/B)

Embodiment 32. The compound of any one of embodiments 1 to 31, having a higher binding affinity for the mu opioid receptor than for the kappa opioid receptor.

Embodiment 33. The compound of any one of embodiments 1 to 31, having a higher binding affinity for the mu opioid receptor than for the delta opioid receptor.

Embodiment 34. The compound of any one of embodiments 1 to 31, having a higher binding affinity for the mu opioid receptor than for the nociceptin receptor.

Embodiment 35. The compound of any one of embodiments 1 to 31, having a lower addiction potential than other medically used opioids or opiates.

Embodiment 36. The compound of any one of embodiments 1 to 31, having a lower addiction potential than morphine, heroin, oxycodone, fentanyl, hydrocodone, hydromorphone, methadone, or oxymorphone.

Embodiment 37. A pharmaceutical composition comprising a pharmaceutically acceptable excipient and a compound of any one of embodiments 1 to 36.

Embodiment 38. A method of treating pain in a subject in need of said treatment, said method comprising administering an effective amount of a compound of any one of embodiments 1 to 36 to said subject.

Embodiment 39. The method of embodiment 38, wherein said method does not comprise an increased risk of respiratory depression or constipation.

Embodiment 40. A method of treating opioid overdose in a subject in need of said treatment, said method comprising administering an effective amount of a compound of any one of embodiments 1 to 36 to said subject.

Embodiment 41. A method of treating addiction in a subject in need of said treatment, said method comprising administering an effective amount of a compound of any one of embodiments 1 to 36 to said subject.

Embodiment 42. A method of treating a psychiatric disorder in a subject in need of said treatment, said method comprising administering an effective amount of a compound of any one of embodiments 1 to 36 to said subject.

Embodiment 43. A method of modulating the activity of an opioid receptor protein, said method comprising contacting said opioid receptor protein with an effective amount of a compound of any one of embodiments 1 to 36 Embodiment 44. The method of embodiment 43, wherein said method does not comprise modulating arrestin function.

EXAMPLES

Example 1

Structure-Based Discovery of Biased μ-Opioid Receptor Analgesics with Reduced Side Effects Opiate addiction, coupled with the potentially lethal side effects of opiates like respiratory depression, has driven optimization campaigns for safer and more effective analgesics since the 19$^{th}$ century. Although the natural products morphine and codeine, and the semi-synthetic drug heroin, were more reliably effective analgesics than raw opium, they retained its liabilities. The classification of opioid receptors into μ, δ, and K subtypes raised hopes that subtype-specific molecules would escape the liabilities of morphinan-based opiates. Despite the introduction of potent synthetic opioid agonists like methadone and fentanyl and the discovery of endogenous opioid peptides, analgesics without the drawbacks of classic opioids have remained elusive. Recent studies have suggested that opioid-induced analgesia results from μ-opioid receptor (μOR) signaling through the G protein $G_i$, while many side effects, including respiratory depression and constipation, may be conferred via β-arrestin pathway signaling. Agonists specific to the μOR and biased toward the $G_i$ signaling pathway are therefore sought both as therapeutic leads and as molecular probes to understand μOR signaling.

The determination of the crystal structures of the μ, δ, K, and nociceptin opioid receptors provided an opportunity to seek new μOR agonists via structure-based approaches. We thus targeted the μOR for structure-based docking, seeking ligands with new chemotypes. We reasoned that such new chemotypes might confer signaling properties with new biological effects.

TABLE 1

Activity data, reporting on the inhibitory constant for μ (MOR), δ (DOR), K (KOR) receptors.

| Compound | $K_i$ MOR (nM) | $K_i$ KOR (nM) | $K_i$ DOR (nM) |
| --- | --- | --- | --- |
| DD 262 P1 | 2600 | 2200 | 14000 |
| DD 262 P2 | 1300 | 1500 | 7400 |
| DD 272A | 140 | 100 | 1800 |
| DD 272B | 57 | 36 | 840 |
| DD 277 | 500 | 700 | 8400 |
| DD 297A | 5.9 | 6.5 | 68 |
| DD 297B | 190 | 260 | 2000 |

For DD 272A, MOR: cAMP BRET: $EC_{50}$: 136 nM; $E_{max}$: 108%. For DD 272B MOR: cAMP BRET: $EC_{50}$: 1.6 nM; $E_{max}$: 50%. For DD 297A, MOR: cAMP BRET: $EC_{50}$: 1.8 nM; $E_{max}$: 80%; MOR: Arrestin DiscoverX: no significant activity. For DD 297B, MOR: cAMP BRET: $EC_{50}$: 12.5 nM; $E_{max}$: 65%.

This study supports a structure-based approach for GPCR ligand discovery. These new chemotypes may stabilize receptor conformations not explored previously and thereby generate novel biological effects. With a novel chemotype in hand, the docked structure provides a straight-forward strategy for optimization.

Example 2

Synthesis Conditions 2-(Dimethylamino)-1,2,3,4-tetrahydronaphthalene-2-carbonitrile (DD260)

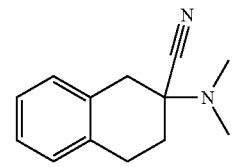

2-Tetralone (1 eq) was weighed into a microwave tube and 2M dimethylamine solution in THF (1.4 eq) was added. The solution was set under argon atmosphere immediately, the tube sealed and the mixture was stirred for 6 h at reflux temperature. The solvent was evaporated and the residue was resolved in TMSCN (2 eq). The mixture was stirred for 2 h at 100° C., allowed to cool to room temperature and the solvent was removed. The residue was used in the next step without further purification.

2-(Dimethylamino)-6-hydroxy-1,2,3,4-tetrahydronaphthalene-2-carbonitrile (DD270)

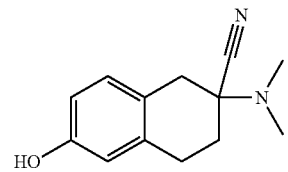 [SMILES: CN(C)C1(C#N)CCc2cc(O)ccc2C1]

DD270 was synthesized following the procedure of DD260 using 6-hydroxy-3,4-dihydronaphthalen-2(1H)-one as starting material.

2-(Dimethylamino)-2,3-dihydro-1H-indene-2-carbonitrile (DD268)

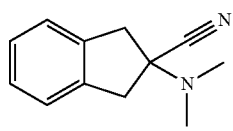

To a solution of indanone (1 eq) and TMSCN (1 eq) in Et$_2$O was added a catalytic amount of ZnI$_2$ and the mixture was stirred at room temperature for 15 minutes. Then a solution of 2M dimethylamine in THF (1.1 eq) was added dropwise. The reaction mixture was stirred at reflux temperature for 3 hours. The solvent was removed and the crude residue was used in the next step without further purification.

2-(Dimethylamino)-5-methoxy-2,3-dihydro-1H-indene-2-carbonitrile (DD279)

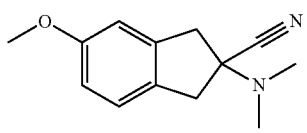 [SMILES: COc1ccc2c(c1)CC(C#N)(N(C)C)C2]

5-methoxy-1,3-dihydro-2H-inden-2-one (200.0 mg, 1 eq) was weighed into a microwave tube and 0.62 mL of 2M dimethylamine solution in THF (1 eq) were added. The solution was set under argon atmosphere immediately, the tube sealed and placed into a heat block, already maintaining a temperature of 100° C. After 3 minutes TMSCN (185.1 uL, 1.2 eq) was added carefully to the mixture and stirring at 100° C. was continued for further 2 minutes. Dichloromethane (20 mL) was added and the organic phase was washed with 10 mL brine. The organic layer was dried over Na$_2$SO$_4$, filtered and the solvent evaporated. The residue was used in the next step without further purification.

Method A: Reduction of nitrile to primary amine:

2-(Aminomethyl)-5-methoxy-N,N-dimethyl-2,3-dihydro-1H-inden-2-amine (DD281)

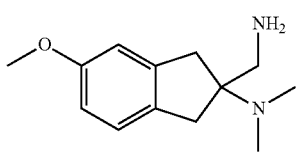

Crude DD279 (250.0 mg, 1 eq) was solved in 5 mL dry diethylether and stirred at 0° C. under argon atmosphere. 4M LiAlH$_4$ in diethylether (1.44 mL, 5 eq) was added dropwise. The reaction mixture was stirred at reflux temperature for 6 h. Then it was cooled down to 0° C. and quenched with 0.2 mL H$_2$O dest., 0.8 mL 1M NaOH solution and few drops of MeOH. The suspension was filtered over Celite mixed with MgSO$_4$ and washed thoroughly with EtOAc. The solvent was evaporated and the residue purified via flash column chromatography (DCM/MeOH/NH$_3$(aq) (9:1:0.1)) giving 67.0 mg of the desired compound (26% over 2 steps).

Compounds synthesized following method A:

2-(Aminomethyl)-N,N-dimethyl-1,2,3,4-tetrahydronaphthalen-2-amine (DD261)

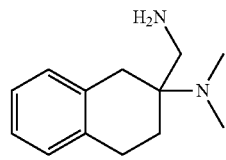

DD261 was synthesized following method A, except reaction mixture was stirred at room temperature for 6 hours. Yield: 8.0 mg (13%, over two steps).

6-(Aminomethyl)-6-(dimethylamino)-5,6,7,8-tetrahydronaphthalen-2-ol (DD271)

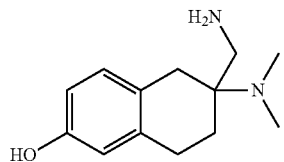 [SMILES: CN(C)C1(CN)CCc2cc(O)ccc2C1]

DD271 was synthesized following method, except reaction mixture was stirred at room temperature for 6 hours. Yield: 24.3 mg (18%, over two steps).

2-(aminomethyl)-N,N-dimethyl-2,3-dihydro-1H-inden-2-amine (DD269)

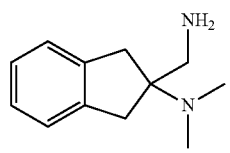

DD269 was synthesized following method A, except reaction mixture was stirred at room temperature for 6 hours. Yield: 65.0 mg (21%, over two steps).

Method B: Synthesis of urea compounds:

1-((2-(dimethylamino)-5-methoxy-2,3-dihydro-1H-inden-2-yl)methyl)-3-((S)-1-(thiophen-3-yl)propan-2-yl)urea (DD295)

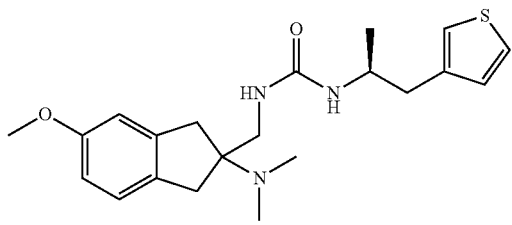 [SMILES: COc1ccc2c(c1)CC(CNC(=O)N[C@@H](C)Cc1ccsc1)(N(C)C)C2]

DD281 (22.0 mg, 1 eq) and triethylamine (11 uL, 0.8 eq) in a microwave tube, solved in DMF (0.6 mL) were stirred at room temperature. 4-nitrophenyl (S)-(1-(thiophen-3-yl)propan-2-yl)carbamate (45.9 mg, 1.5 eq) in 0.6 mL DMF was added, the tube sealed and the reaction mixture stirred for 3 h at room temperature. Then EtOAc (10 mL) was added and the organic phase was washed four times with 1N NaOH solution (aq.). The organic layer was dried over Na$_2$SO$_4$, filtered and the solvent was evaporated, giving 38.0 mg of DD295 (98%). No further purification was required.

Compounds synthesized following Method B:

(S)-1-((2-(dimethylamino)-2,3-dihydro-1H-inden-2-yl)methyl)-3-(1-(thiophen-3-yl)propan-2-yl)urea (DD277)

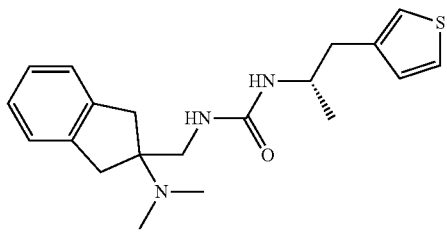

Yield: 12.0 mg (53%)

1-((2-(Dimethylamino)-1,2,3,4-tetrahydronaphthalen-2-yl)methyl)-3-((S)-1-(thiophen-3-yl)propan-2-yl)urea (DD262)

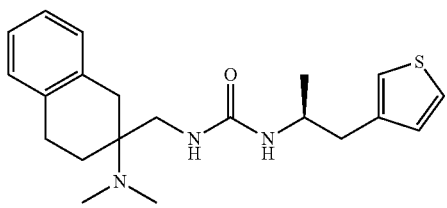 [SMILES: C[C@@H](Cc1ccsc1)NC(=O)NCC1(N(C)C)CCc2ccccc2C1]

Purification and separation of diastereomers was performed by preparative HPLC using RP-C18 column. Yield: 5.5 mg (76%)

1-((2-(Dimethylamino)-6-hydroxy-1,2,3,4-tetrahydronaphthalen-2-yl)methyl)-3-((S)-1-(thiophen-3-yl)propan-2-yl)urea (DD272)

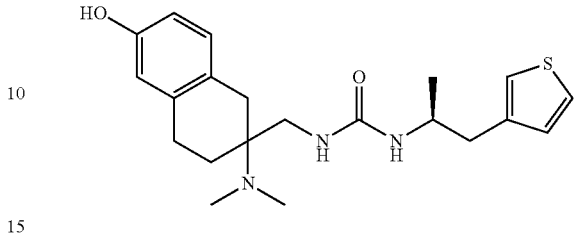

DD272 was synthesized following method B except using an adjusted workup procedure. The solution was diluted with isopropanol/EtOAc (1:3) and washed with a saturated aqueous solution of NaHCO$_3$. The organic layer was extracted with 0.1N HCl-solution and the aqueous extracts were adjusted to pH 9 with saturated aqueous NaHCO$_3$/Na$_2$CO$_3$ solution and finally extracted with EtOAc. The organic layers were dried (Na$_2$SO$_4$), filtered and concentrated under reduced pressure. The residue was purified by preparative HPLC giving the corresponding formate. Yield: 23.0 mg (65%).

Diastereomeres were separated via Chiralpak IC column, fluent: n-hexane/isopropanol (+0.1% ethylendiamine) 70:30, 17 min.

1-((2-(dimethylamino)-5-hydroxy-2,3-dihydro-1H-inden-2-yl)methyl)-3-((S)-1-(thiophen-3-yl)propan-2-yl)urea (DD297)

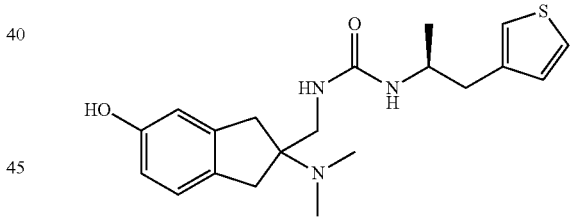

DD295 (35.0 mg, 1 eq) was solved in dry DCM (7 mL) and stirred at around −10° C. (acetone-ice-bath) under argon atmosphere. 0.81 mL of 1M BBr$_3$ solution in DCM (9 eq) was added dropwise and the mixture was allowed to warm up to room temperature. After 1 h of stirring the reaction was quenched with 3 mL MeOH (dry). The solvent was evaporated and the residue resolved in MeOH. This solvation-evaporation sequence was repeated three times with MeOH and one time with EtOH. Purification was performed via flash column chromatography (DCM/MeOH/NH$_3$(aq) 15:1:0.1) giving 31.0 mg (92%) of the diastereomeric mixture.

Diastereomeres were separated via Chiralpak IC column, fluent: n-hexane/isopropanol (+0.1% ethylendiamine) 80:20, 15 min.

Final purification of single diastereomers was performed by preparative HPLC (acetonitrile/H$_2$O (+0.1% formic acid)) giving 7.5 mg DD297A and 10.0 mg DD297B as their corresponding formates.

Example 3

Biological Activity

Gi/o Induced cAMP Inhibition

Determination of functional activity of selected embodiments was performed using a BRET-based cAMP accumulation assay. HEK-293T cells were transiently cotransfected with pcDNA3L-His-CAMYEL42 (ATCC via LCG Standards, Wesel, Germany) and with pcDNA of the human µOR at a cDNA ratio of 4:1 using Mirus TransIT-293 transfection reagent. After 24 hrs of transfection cells were seeded into white half-area 96-well plates at a density of 10000 cells/well and grown for further 24 hrs. On the day of measurement, medium was removed and replaced by Phosphate Buffered Saline (PBS) and cells were serum starved for 1 hr before treatment with ligands. Cells were preincubated with coelenterazine h (Progmega, Mannheim, Germany) for 5 min at a final concentration of 5 µM before adding forskolin (final concentration 10 µM) to start cAMP accumulation. Immediately after adding forskolin, a series of concentrations of test compounds were added to the cells. After incubating the microplates for 15 min at 37° C. BRET measurement was performed using a Clariostar plate reader (BMG LabTech, Ortenberg, Germany). Emission signals from *Renilla* Luciferase and YFP were measured simultaneously using a BRET filter set (475-30 nm/535-30 nm). Resulting BRET ratios (emission at 535-30 nm/emission at 475-30 nm) were calculated and transformed into dose/response curves. Curves were fitted by nonlinear regression using GraphPad Prism 6.0 (GraphPad, San Diego, Calif.) and subsequently normalized to basal BRET ratio obtained from dPBS (0%) and the maximum effect of morphine (100%) as a reference. Representative parameters for functional activation ($EC_{50}$ and $E_{max}$) are summarized in Table 2 and are the mean values derived from three to ten independent experiments each done in triplicate.

β-Arrestin Recruitment Assays

β-Arrestin recruitment was measured by using the PathHunter enzyme complementation assay (DiscoverX, Birmingham, U.K.) as described in the manufacturer's protocol. HEK-293 cells stably expressing the enzyme acceptor (EA) tagged β-arrestin-2 fusion protein were transiently transfected with the ProLink tagged MOR-PK1 construct employing Mirus TransIT-293 transfection reagent. After 24 h cells were transferred into white clear bottom 384-well plates (5000 cells/well) (Greiner Bio-One) and maintained for further 24 h at 37° C., 5% $CO_2$. Test compounds were incubated with the cells in a range from 0.01 nM to 1 µM dissolved in PBS for 90 min at 37° C. Arrestin recruitment was stopped by addition of detection mix for 60 min at room temperature. Chemiluminescence was determined using a Clariostar plate reader. Data analysis was done by nonlinear regression using the algorithms for log(agonist) vs. response of PRISM 6.0 (GraphPad, San Diego, Calif.). Raw data were normalized to basal (0%) and the maximum effect of DAMGO (100%). For testing the arrestin recruitment in the presence of GRK proteins cells were cotransfected with ProLink tagged MOR-PK1 and GRK2 at equal quantities. Representative parameters for functional activation ($EC_{50}$ and $E_{max}$) are summarized in Table 2 and are the mean values derived from two to four independent experiments each done in duplicate.

TABLE 2

| | MOR activation | | | | | |
|---|---|---|---|---|---|---|
| | cAMP accumulation | | β-arrestin recruitment | | β-arrestin recruitment (+GRK2) | |
| Compound | EC50 [nM] | Emax [%] | EC50 [nM] | Emax [%] | EC50 [nM] | Emax [%] |
| DAMGO | 0.54 | 103 | 1500 | 100 | 73 | 100 |
| morphine | 4.0 | 100 | nd | nd | nd | nd |
| DD272A | 24 | 75 | — | <3 | — | <3 |
| DD272B | 1.5 | 98 | — | <3 | 450 | 7 |
| DD297A | 1.2 | 80 | — | <3 | 42 | 13 |
| DD297B | 13 | 73 | — | <3 | 670 | 7 |

What is claimed is:

1. A compound having the formula:

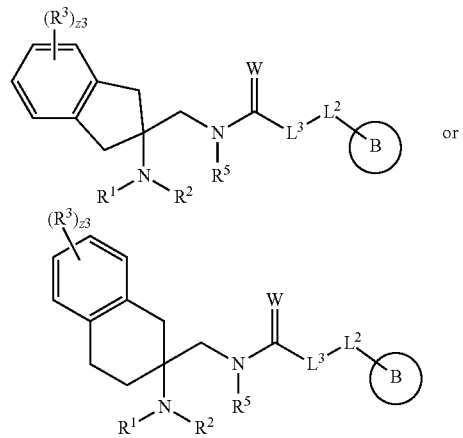

wherein,

W is O;

Ring B is independently a substituted or unsubstituted $C_6$-$C_{10}$ aryl, or substituted or unsubstituted 5 to 10 membered heteroaryl;

$L^2$ is a substituted or unsubstituted ($C_2$-$C_5$) alkylene, or substituted or unsubstituted 2 to 5 membered heteroalkylene;

$R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)OH, —NHOH, —CHF$_2$, —CH$_2$F, —OCF$_3$, —OCHF$_2$, —OCH$_2$F, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^3$ is independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; or two adjacent $R^3$ substituents may optionally be joined to form a substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

$R^{10}$ is hydrogen;

$R^1$ and $R^2$ may optionally be joined to form a substituted or unsubstituted 3 to 6 membered heterocycloalkyl or substituted or unsubstituted 5 to 6 membered heteroaryl;

$R^1$ and $R^3$ may optionally be joined to form a substituted or unsubstituted 3 to 6 membered heterocycloalkyl or substituted or unsubstituted 5 to 6 membered heteroaryl;

$R^2$ and $R^3$ may optionally be joined to form a substituted or unsubstituted 3 to 6 membered heterocycloalkyl or substituted or unsubstituted 5 to 6 membered heteroaryl;

$L^3$ is —N($R^6$)—;

$R^5$ is hydrogen, —$CF_3$, —CN, —COOH, —$CONH_2$, —$CHF_2$, —$CH_2F$, substituted or unsubstituted ($C_1$-$C_8$) alkyl, or substituted or unsubstituted 2 to 8 membered heteroalkyl;

$R^6$ is hydrogen, —$CF_3$, —CN, —COOH, —$CONH_2$, —$CHF_2$, —$CH_2F$, substituted or unsubstituted ($C_1$-$C_8$) alkyl, or substituted or unsubstituted 2 to 8 membered heteroalkyl; and z3 is an integer from to 1 to 10.

2. A compound having the formula:

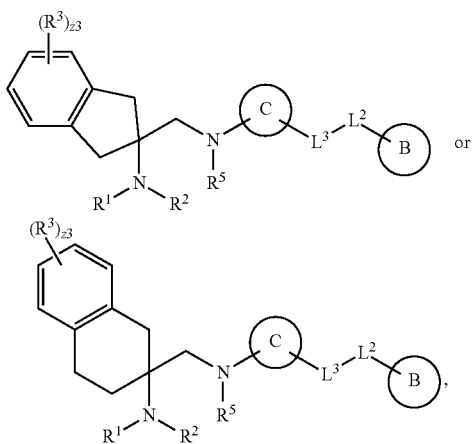

wherein:

Ring B is independently a substituted or unsubstituted $C_6$-$C_{10}$ aryl, or substituted or unsubstituted 5 to 10 membered heteroaryl;

Ring C is a substituted or unsubstituted $C_3$-$C_6$ arylene, or substituted or unsubstituted 3 to 6 membered heteroarylene;

$L^2$ is a substituted or unsubstituted ($C_2$-$C_5$) alkylene, or substituted or unsubstituted 2 to 5 membered heteroalkylene;

$R^1$ and $R^2$ are independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl;

—$OR^{10}$, $R^3$ is independently hydrogen, halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; or two adjacent $R^3$ substituents may optionally be joined to form a substituted or unsubstituted $C_3$-$C_8$ cycloalkyl, substituted or unsubstituted 3 to 8 membered heterocycloalkyl, substituted or unsubstituted$C_6$-$C_{10}$ aryl, or substituted or unsubstituted 5 to 10 membered heteroaryl;

$R^{10}$ is hydrogen;

$R^1$ and $R^2$ may optionally be joined to form a substituted or unsubstituted 3 to 6 membered heterocycloalkyl or substituted or unsubstituted 5 to 6 membered heteroaryl;

$R^1$ and $R^3$ may optionally be joined to form a substituted or unsubstituted 3 to 6 membered heterocycloalkyl or substituted or unsubstituted 5 to 6 membered heteroaryl;

$R^2$ and $R^3$ may optionally be joined to form a substituted or unsubstituted 3 to 6 membered heterocycloalkyl or substituted or unsubstituted 5 to 6 membered heteroaryl;

$L^3$ is —N($R^6$)—;

$R^5$ is hydrogen, —$CF_3$, —CN, —COOH, —$CONH_2$, —$CHF_2$, —$CH_2F$, substituted or unsubstituted ($C_1$-$C_8$) alkyl, or substituted or unsubstituted 2 to 8 membered heteroalkyl;

$R^6$ is hydrogen, —$CF_3$, —CN, —COOH, —$CONH_2$, —$CHF_2$, —$CH_2F$, substituted or unsubstituted ($C_1$-$C_8$) alkyl, or substituted or unsubstituted 2 to 8 membered heteroalkyl; and z3 is an integer from to 1 to 10.

3. The compound of claim 1, having the formula:

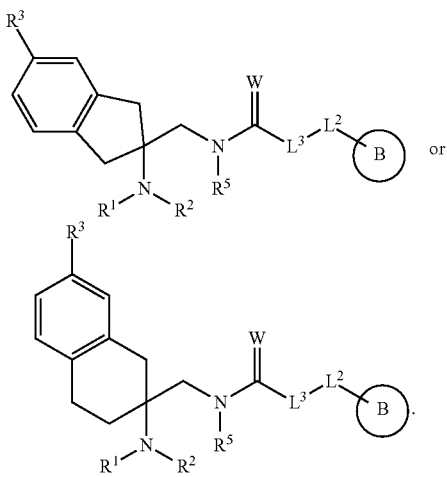

or

4. The compound of claim 1, wherein $R^3$ is —OH.

5. The compound of claim 1, wherein:

$R^1$ and $R^3$ may optionally be joined to form a substituted or unsubstituted 3 to 6 membered heterocycloalkyl; or $R^2$ and $R^3$ may optionally be joined to form a substituted or unsubstituted 3 to 6 membered heterocycloalkyl.

6. The compound of claim 1, wherein Ring B is unsubstituted phenyl or unsubstituted 3-thienyl.

7. The compound of claim 1, wherein $R^1$ and $R^2$ is substituted ($C_1$-$C_5$) alkyl, substituted with a substituted or unsubstituted phenyl, substituted or unsubstituted furanyl, substituted or unsubstituted pyridinyl, substituted or unsubstituted thiophenyl, substituted or unsubstituted pyrazolyl, substituted or unsubstituted imidazolyl, substituted or unsubstituted oxazolyl, substituted or unsubstituted isoxazolyl, substituted or unsubstituted thiazolyl, substituted or unsubstituted pyrrolyl, or substituted or unsubstituted thienyl.

8. The compound of claim 1, wherein $R^1$ and $R^2$ are unsubstituted methyl or wherein $R^1$ and $R^2$ are joined to form a substituted or unsubstituted 3 to 6 membered heterocycloalkyl or substituted or unsubstituted 5 to 6 membered heteroaryl.

9. The compound of claim 1, wherein $R^5$ is hydrogen, substituted or unsubstituted ($C_1$-$C_5$) alkyl or substituted or unsubstituted 2 to 5 membered heteroalkyl.

10. The compound of claim 1, wherein:

$R^6$ is hydrogen, substituted or unsubstituted ($C_1$-$C_5$) alkyl or substituted or unsubstituted 2 to 5 membered heteroalkyl.

11. The compound of claim 1, having the formula:

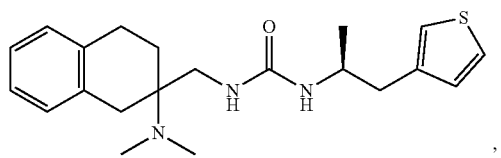

(DD 262 P1/P2)

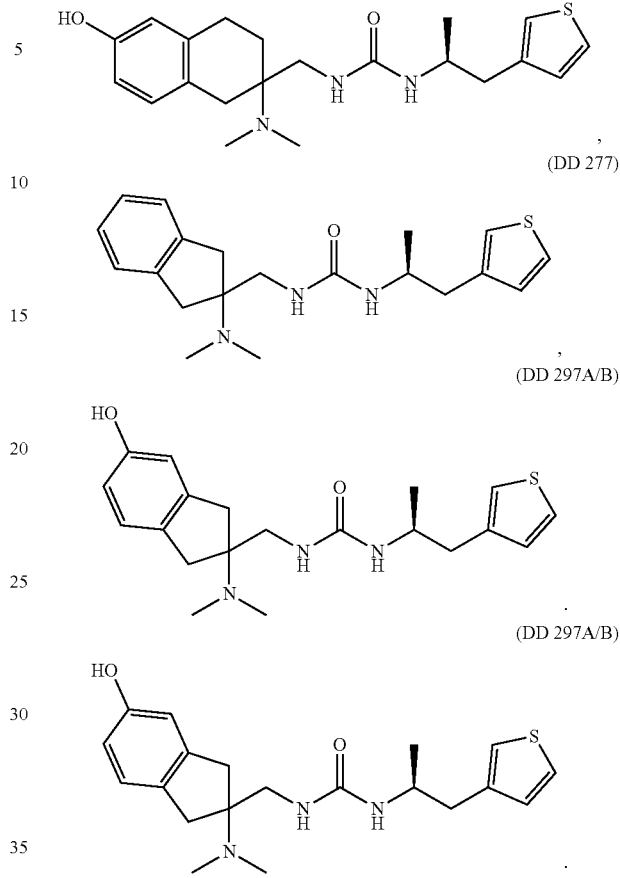

12. A pharmaceutical composition comprising a pharmaceutically acceptable excipient and a compound of claim 1.

13. A method of treating pain in a subject in need of said treatment, said method comprising administering an effective amount of a compound of claim 1 to said subject, wherein said method does not comprise an increased risk of respiratory depression or constipation.

14. The compound of claim 1, wherein $R^3$ is independently halogen, —$CF_3$, —CN, —$N_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$CHF_2$, —$CH_2F$, —$OCF_3$, —$OCHF_2$, —$OCH_2F$, substituted or unsubstituted ($C_1$-$C_5$) alkyl, or substituted or unsubstituted 2 to 5 membered heteroalkyl.

15. The compound of claim 1, wherein $R^3$ is independently halogen, —$CF_3$, —OH, —$NH_2$, —COOH, —$CONH_2$, —NHC=(O)$NHNH_2$, —NHC=(O)$NH_2$, —NHC=(O)H, —NHC(O)OH, or —NHOH.

16. The compound of claim 1, wherein:
Ring B is unsubstituted thienyl;
Ring B is unsubstituted phenyl;
Ring B is unsubstituted benzothienyl;
Ring B is para-methyl substituted phenyl;
Ring B is unsubstituted napththyl; or
Ring B is unsubstituted 2,3-dihydro-1H-indenyl.

17. The compound of claim 1, wherein $R^1$ is unsubstituted ($C_1$-$C_2$) alkyl.

18. The compound of claim 1, wherein $R^2$ is unsubstituted ($C_1$-$C_2$) alkyl.

19. The compound of claim 1, having the formula:
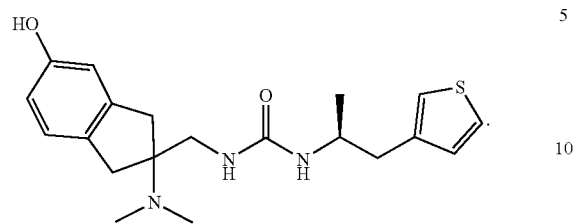
(DD 297A/B)
* * * * *